United States Patent
Schalk et al.

(10) Patent No.: US 10,752,922 B2
(45) Date of Patent: Aug. 25, 2020

(54) PRODUCTION OF MANOOL

(71) Applicant: FIRMENICH SA, Satigny (CH)

(72) Inventors: Michel Schalk, Geneva (CH); Laurent Daviet, Geneva (CH); Letizia Rocci, Geneva (CH); Daniel Solis Escalante, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/472,120

(22) PCT Filed: Dec. 18, 2017

(86) PCT No.: PCT/EP2017/083372
§ 371 (c)(1),
(2) Date: Jun. 20, 2019

(87) PCT Pub. No.: WO2018/114839
PCT Pub. Date: Jun. 28, 2018

(65) Prior Publication Data
US 2019/0352673 A1    Nov. 21, 2019

(30) Foreign Application Priority Data

Dec. 22, 2016    (EP) .................................... 16206349

(51) Int. Cl.
*C12N 9/88*        (2006.01)
*C12N 1/16*        (2006.01)
(Continued)

(52) U.S. Cl.
CPC .................. *C12P 7/02* (2013.01); *C12N 1/16* (2013.01); *C12N 1/20* (2013.01); *C12N 9/88* (2013.01);
(Continued)

(58) Field of Classification Search
None
See application file for complete search history.

(56) References Cited

U.S. PATENT DOCUMENTS 7,294,492 B2    11/2007   Choi et al.

FOREIGN PATENT DOCUMENTS

EP          0212254 A2    3/1987
WO       2009095366 A1    8/2009
(Continued)

OTHER PUBLICATIONS

Uni Prot Accession No. COSSW6_WHEAT, published May 26, 2009 (Year: 2009).*

(Continued)

*Primary Examiner* — Richard C Ekstrom
(74) *Attorney, Agent, or Firm* — Armstrong Teasdale LLP

(57) ABSTRACT

Described herein are methods of producing (+)-manool, the methods including: contacting geranylgeranyl diphosphate with a copalyl diphosphate (CPP) synthase to form a (9S, 10S)-copalyl diphosphate and contacting the CPP with a sclareol synthase enzyme to form (+)-manool and derivatives thereof. Also described herein are nucleic acids encoding CPP synthases and sclareol synthases for use in the methods. Further described herein are expression vectors and non-human host organisms and cells including nucleic acids encoding a CPP synthase and a sclareol synthase as described herein.

16 Claims, 8 Drawing Sheets

Specification includes a Sequence Listing.

(51) Int. Cl.
  *C12N 1/20* (2006.01)
  *C12N 15/70* (2006.01)
  *C12N 15/81* (2006.01)
  *C12P 7/02* (2006.01)

(52) U.S. Cl.
  CPC ............ *C12N 15/70* (2013.01); *C12N 15/81* (2013.01); *C12Y 505/01012* (2013.01)

(56) References Cited

FOREIGN PATENT DOCUMENTS

| WO | 2013064411 A1 | 5/2013 |
| WO | 2014022434 A1 | 2/2014 |
| WO | 2015113570 A1 | 8/2015 |
| WO | 2015197075 A1 | 12/2015 |

OTHER PUBLICATIONS

Guo et al., "Protein tolerance to random amino acid change", Proceedings of the National Academy of Sciences USA, vol. 101, No. 25, pp. 9205-9210, 2004 (Year: 2004).*

Uni Prot Accession No. A0A075FA51_MARVU, published Oct. 29, 2014 (Year: 2014).*

Uni Prot Accession No. W8QQT6_ROSOF, published May 14, 2014 (Year: 2014).*

International Search Report for International Application No. PCT/EP2017/083372, dated Jul. 30, 2018, 10 pages.

Griggs et al., "Regulated expression of the GAL4 activator gene in yeast provides a sensitive genetic switch for glucose repression", Proc Natl Acad Sci USA, Published Oct. 1991, vol. 88, pp. 8597-8601.

Kuijpers et al., "A versatile, efficient strategy for assembly of multi-fragment expression vectors in *Saccharomyces cerevisiae* using 60 bp synthetic recombination sequences", Microb Cell Fact., Published May 10, 2013, vol. 12, No. 47, 13 pages.

Stemmer, "DNA shuffling by random fragmentation and reassembly: in vitro recombination for molecular evolution", Proc Natl Acad Sci USA, Published Oct. 1994, vol. 91, pp. 10747-10751.

Tatusova et al., "BLAST 2 Sequences, a new tool for comparing protein and nucleotide sequences", FEMS Microbiol Lett., Published Aug. 1, 1999, vol. 177, No. 1, pp. 187-188.

Toyomasu et al., "Cloning and Characterization of cDNAs Encoding ent-Copalyl Diphosphate Synthases in Wheat: Insight into the Evolution of Rice Phytoalexin Biosynthetic Genes", Biosci. Biotechnol. Biochem., Published Mar. 7, 2009, vol. 73, No. 3, pp. 772-775.

Westfall et al., "Production of amorphadiene in yeast, and its conversion to dihydroartemisinic acid, precursor to the antimalarial agent artemisinin", Proc. Natl. Acad. Sci. U.S.A., vol. 109, pp. E111-E118.

Wu et al., "Functional characterization of wheat copalyl diphosphate synthases sheds light on the early evolution of abdane-related diterpenoid metabolism in the cereals", Phytochemistry, Published Dec. 1, 2012, vol. 84, No. 1, pp. 40-46.

Zerbe et al., "Diterpene synthases of the biosynthetic system of medicinally active diterpenoids in Marrubium vulgare", The Plant Journal, Published Sep. 1, 2014, vol. 79, No. 6, pp. 914-927.

* cited by examiner

- Figure 1 -
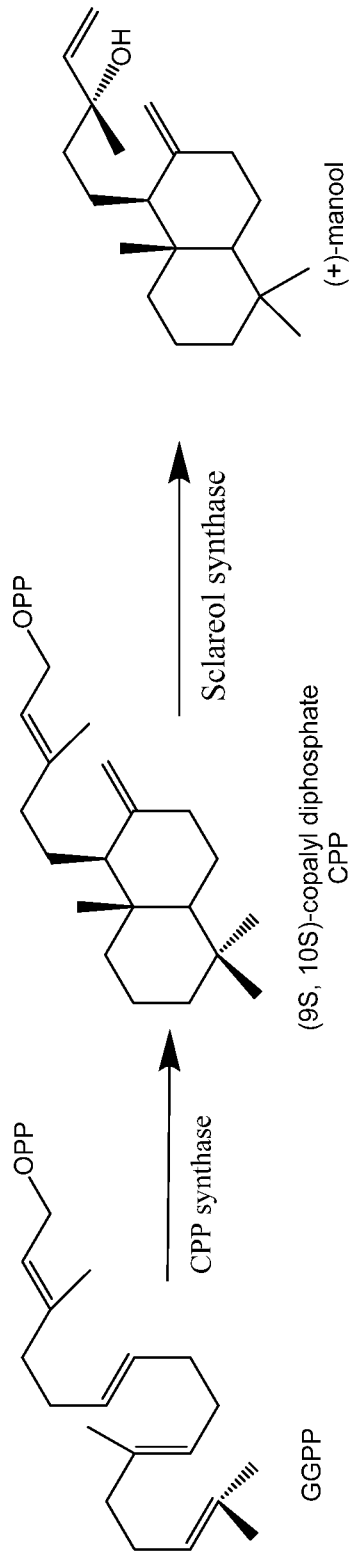

- Figure 2 -
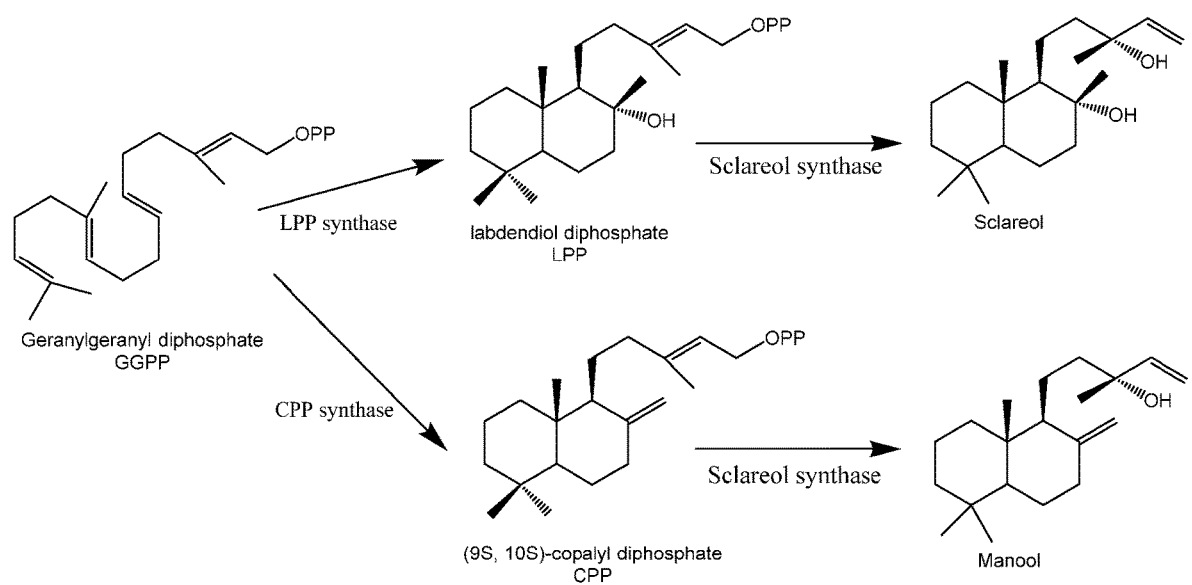

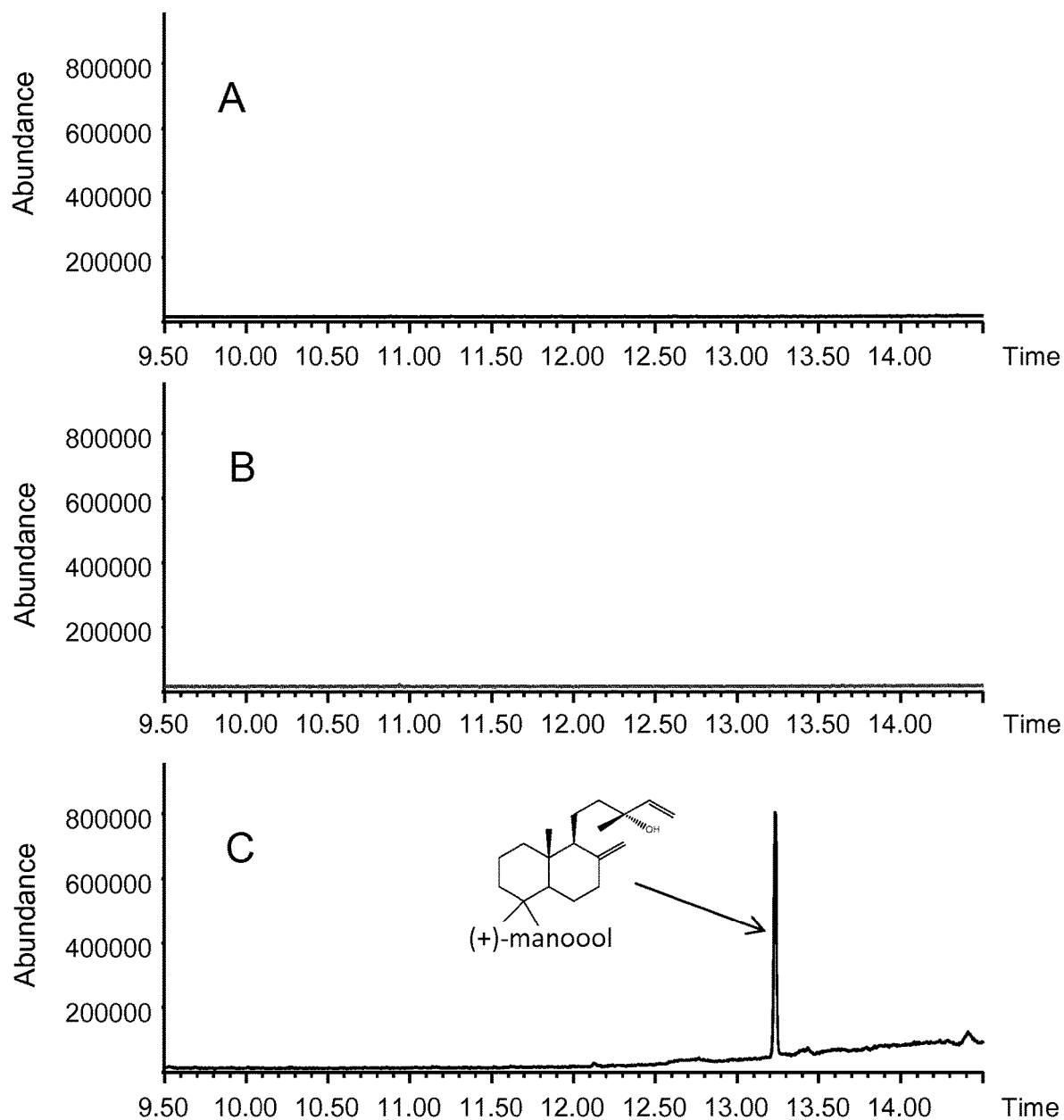
- Figure 3 -

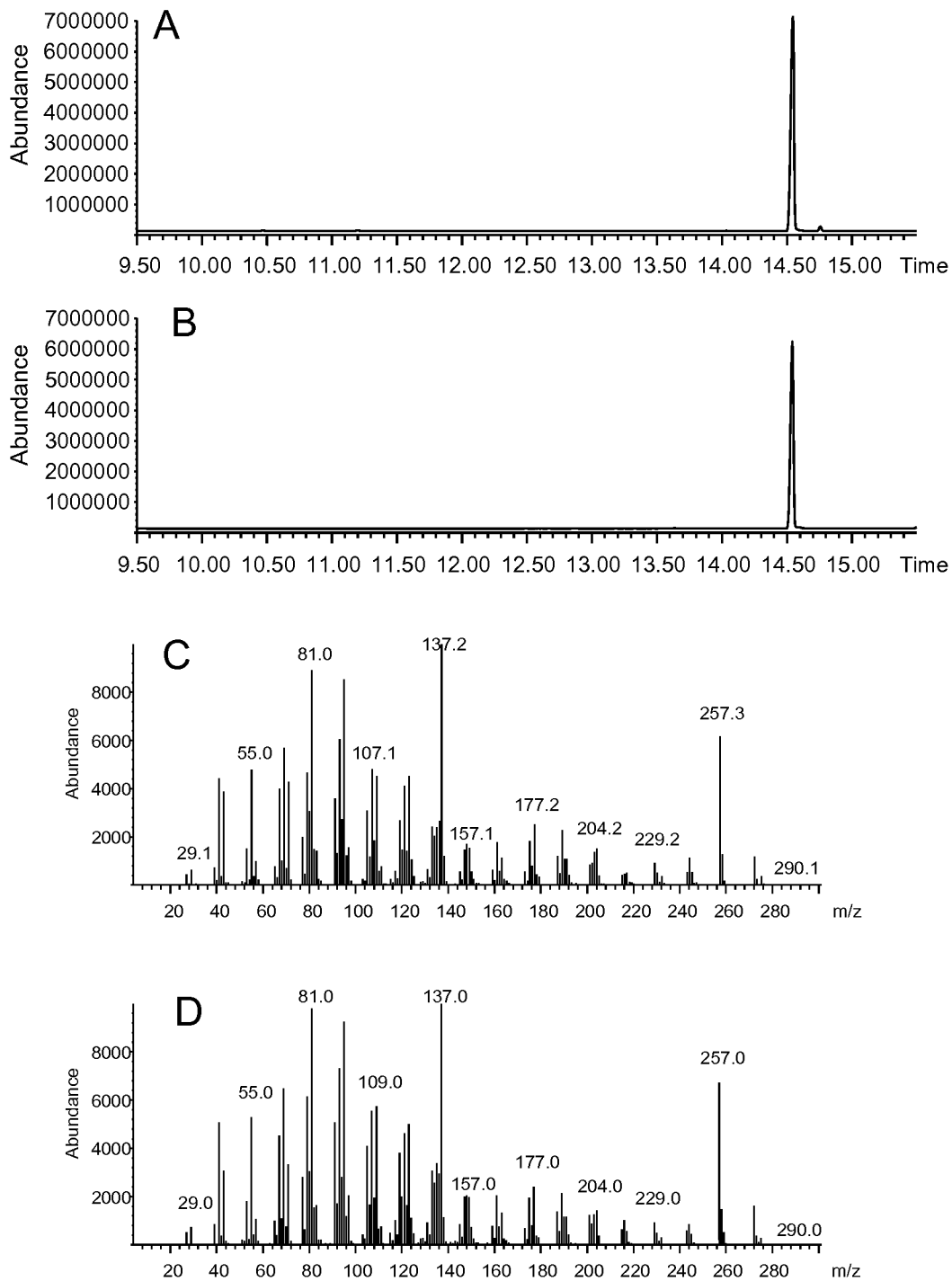
- Figure 4 -

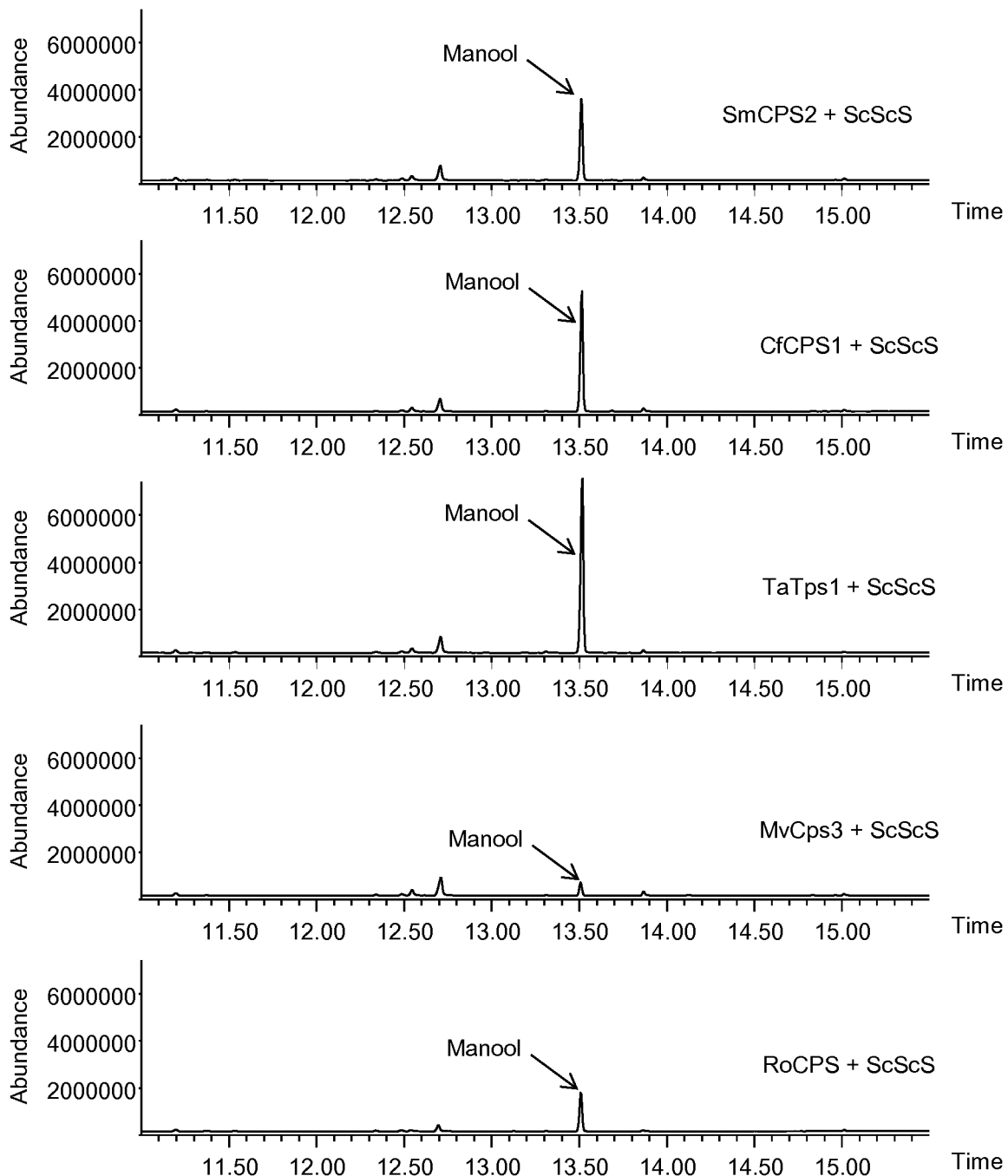
- Figure 5 -

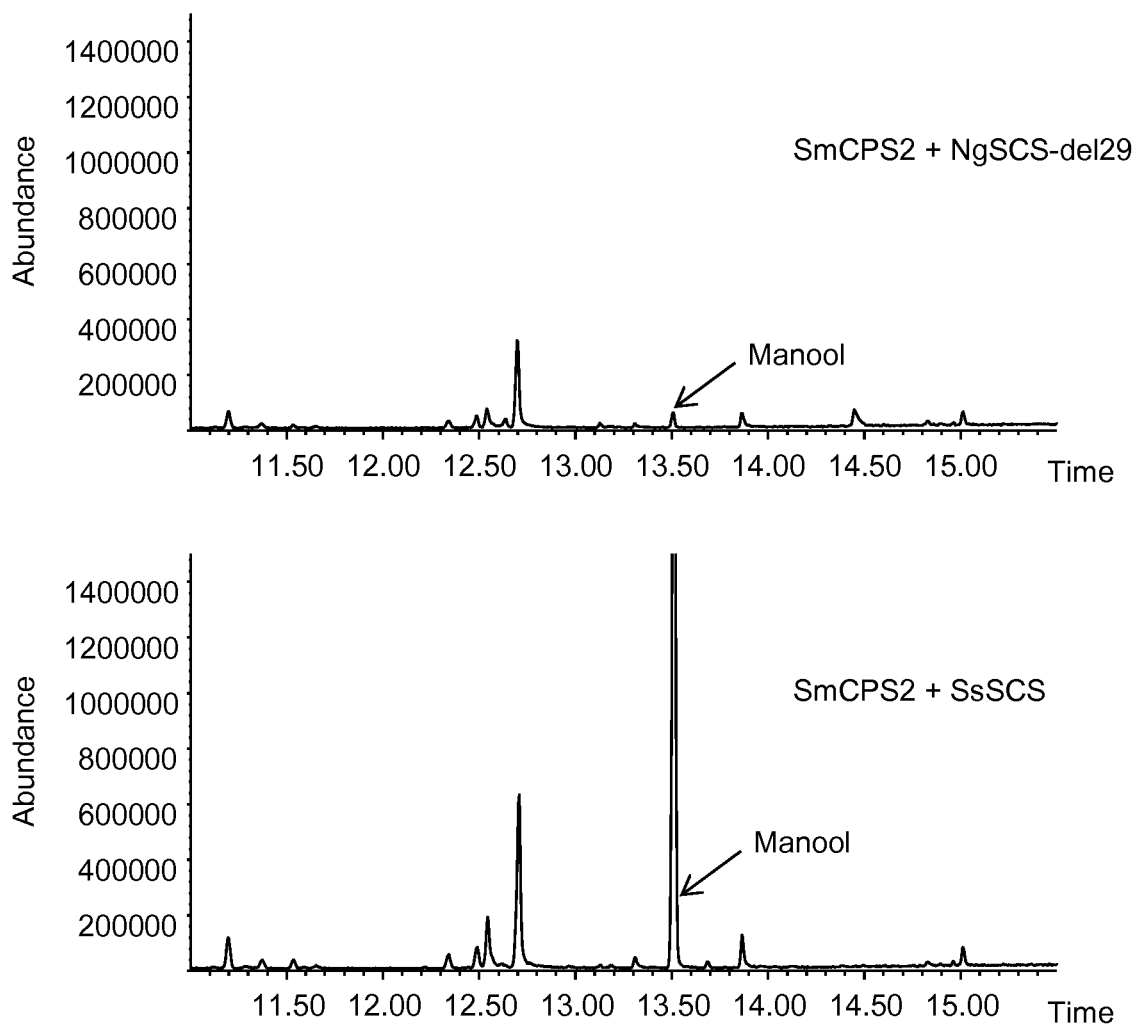
- Figure 6 –

– Figure 7 –
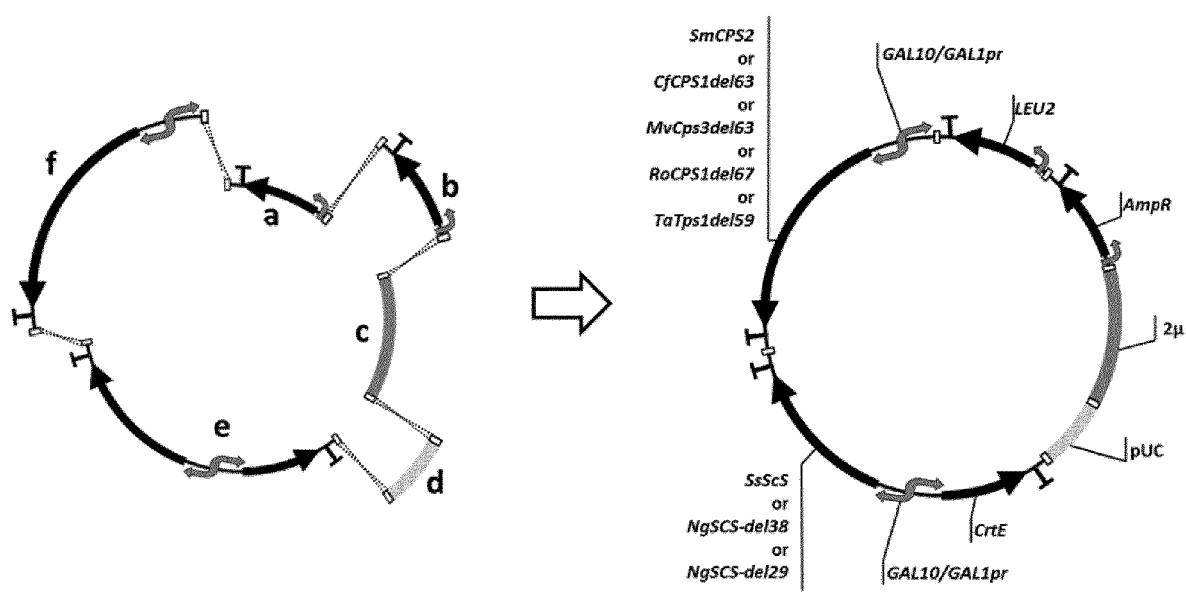

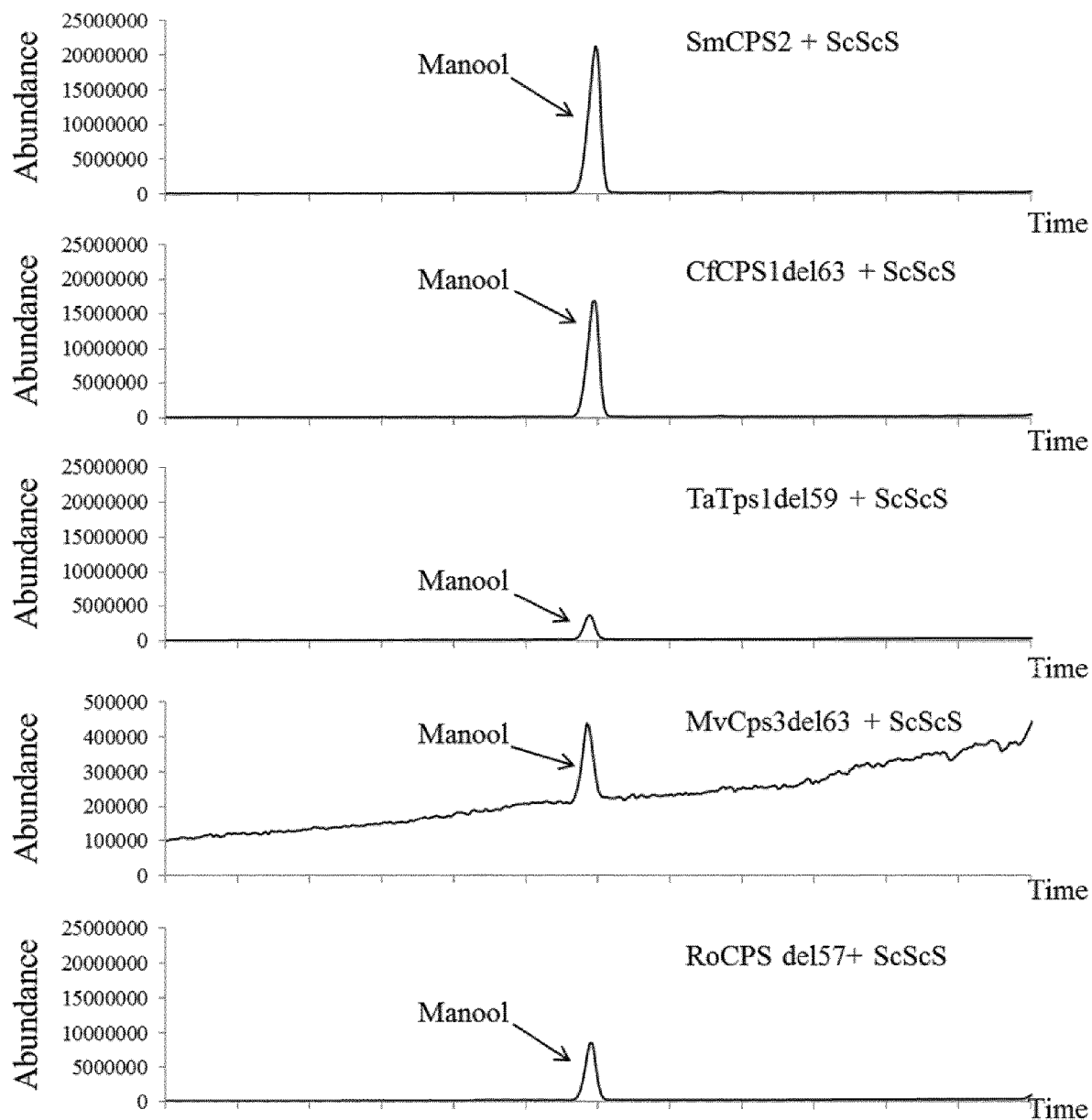
- Figure 8 –

SEQUENCE LISTING

```
<160> NUMBER OF SEQ ID NOS: 45

<210> SEQ ID NO 1
<211> LENGTH: 793
<212> TYPE: PRT
<213> ORGANISM: Salvia miltiorrhiza

<400> SEQUENCE: 1

Met Ala Ser Leu Ser Ser Thr Ile Leu Ser Arg Ser Pro Ala Ala Arg
1               5                   10                  15
```

-continued

```
Arg Arg Ile Thr Pro Ala Ser Ala Lys Leu His Arg Pro Glu Cys Phe
            20                  25                  30
Ala Thr Ser Ala Trp Met Gly Ser Ser Lys Asn Leu Ser Leu Ser
        35                  40                  45
Tyr Gln Leu Asn His Lys Lys Ile Ser Val Ala Thr Val Asp Ala Pro
    50                  55                  60
Gln Val His Asp His Asp Gly Thr Thr Val His Gln Gly His Asp Ala
65                  70                  75                  80
Val Lys Asn Ile Glu Asp Pro Ile Glu Tyr Ile Arg Thr Leu Leu Arg
                85                  90                  95
Thr Thr Gly Asp Gly Arg Ile Ser Val Ser Pro Tyr Asp Thr Ala Trp
            100                 105                 110
Val Ala Met Ile Lys Asp Val Glu Gly Arg Asp Gly Pro Gln Phe Pro
        115                 120                 125
Ser Ser Leu Glu Trp Ile Val Gln Asn Gln Leu Glu Asp Gly Ser Trp
    130                 135                 140
Gly Asp Gln Lys Leu Phe Cys Val Tyr Asp Arg Leu Val Asn Thr Ile
145                 150                 155                 160
Ala Cys Val Val Ala Leu Arg Ser Trp Asn Val His Ala His Lys Val
                165                 170                 175
Lys Arg Gly Val Thr Tyr Ile Lys Glu Asn Val Asp Lys Leu Met Glu
            180                 185                 190
Gly Asn Glu Glu His Met Thr Cys Gly Phe Glu Val Val Phe Pro Ala
        195                 200                 205
Leu Leu Gln Lys Ala Lys Ser Leu Gly Ile Glu Asp Leu Pro Tyr Asp
    210                 215                 220
Ser Pro Ala Val Gln Glu Val Tyr His Val Arg Glu Gln Lys Leu Lys
225                 230                 235                 240
Arg Ile Pro Leu Glu Ile Met His Lys Ile Pro Thr Ser Leu Leu Phe
                245                 250                 255
Ser Leu Glu Gly Leu Glu Asn Leu Asp Trp Asp Lys Leu Leu Lys Leu
            260                 265                 270
Gln Ser Ala Asp Gly Ser Phe Leu Thr Ser Pro Ser Ser Thr Ala Phe
        275                 280                 285
Ala Phe Met Gln Thr Lys Asp Glu Lys Cys Tyr Gln Phe Ile Lys Asn
    290                 295                 300
Thr Ile Asp Thr Phe Asn Gly Gly Ala Pro His Thr Tyr Pro Val Asp
305                 310                 315                 320
Val Phe Gly Arg Leu Trp Ala Ile Asp Arg Leu Gln Arg Leu Gly Ile
                325                 330                 335
Ser Arg Phe Phe Glu Pro Glu Ile Ala Asp Cys Leu Ser His Ile His
            340                 345                 350
Lys Phe Trp Thr Asp Lys Gly Val Phe Ser Gly Arg Glu Ser Glu Phe
        355                 360                 365
Cys Asp Ile Asp Asp Thr Ser Met Gly Met Arg Leu Met Arg Met His
    370                 375                 380
Gly Tyr Asp Val Asp Pro Asn Val Leu Arg Asn Phe Lys Gln Lys Asp
385                 390                 395                 400
Gly Lys Phe Ser Cys Tyr Gly Gly Gln Met Ile Glu Ser Pro Ser Pro
                405                 410                 415
Ile Tyr Asn Leu Tyr Arg Ala Ser Gln Leu Arg Phe Pro Gly Glu Glu
            420                 425                 430
Ile Leu Glu Asp Ala Lys Arg Phe Ala Tyr Asp Phe Leu Lys Glu Lys
```

```
                    435                 440                 445
Leu Ala Asn Asn Gln Ile Leu Asp Lys Trp Val Ile Ser Lys His Leu
450                 455                 460

Pro Asp Glu Ile Lys Leu Gly Leu Glu Met Pro Trp Leu Ala Thr Leu
465                 470                 475                 480

Pro Arg Val Glu Ala Lys Tyr Tyr Ile Gln Tyr Tyr Ala Gly Ser Gly
                    485                 490                 495

Asp Val Trp Ile Gly Lys Thr Leu Tyr Arg Met Pro Glu Ile Ser Asn
                500                 505                 510

Asp Thr Tyr His Asp Leu Ala Lys Thr Asp Phe Lys Arg Cys Gln Ala
            515                 520                 525

Lys His Gln Phe Glu Trp Leu Tyr Met Gln Glu Trp Tyr Glu Ser Cys
        530                 535                 540

Gly Ile Glu Glu Phe Gly Ile Ser Arg Lys Asp Leu Leu Ser Tyr
545                 550                 555                 560

Phe Leu Ala Thr Ala Ser Ile Phe Glu Leu Glu Arg Thr Asn Glu Arg
                565                 570                 575

Ile Ala Trp Ala Lys Ser Gln Ile Ile Ala Lys Met Ile Thr Ser Phe
            580                 585                 590

Phe Asn Lys Glu Thr Thr Ser Glu Glu Asp Lys Arg Ala Leu Leu Asn
        595                 600                 605

Glu Leu Gly Asn Ile Asn Gly Leu Asn Asp Thr Asn Gly Ala Gly Arg
610                 615                 620

Glu Gly Gly Ala Gly Ser Ile Ala Leu Ala Thr Leu Thr Gln Phe Leu
625                 630                 635                 640

Glu Gly Phe Asp Arg Tyr Thr Arg His Gln Leu Lys Asn Ala Trp Ser
                645                 650                 655

Val Trp Leu Thr Gln Leu Gln His Gly Glu Ala Asp Asp Ala Glu Leu
            660                 665                 670

Leu Thr Asn Thr Leu Asn Ile Cys Ala Gly His Ile Ala Phe Arg Glu
        675                 680                 685

Glu Ile Leu Ala His Asn Glu Tyr Lys Ala Leu Ser Asn Leu Thr Ser
690                 695                 700

Lys Ile Cys Arg Gln Leu Ser Phe Ile Gln Ser Glu Lys Glu Met Gly
705                 710                 715                 720

Val Glu Gly Glu Ile Ala Ala Lys Ser Ser Ile Lys Asn Lys Glu Leu
                725                 730                 735

Glu Glu Asp Met Gln Met Leu Val Lys Leu Val Leu Glu Lys Tyr Gly
            740                 745                 750

Gly Ile Asp Arg Asn Ile Lys Lys Ala Phe Leu Ala Val Ala Lys Thr
        755                 760                 765

Tyr Tyr Tyr Arg Ala Tyr His Ala Ala Asp Thr Ile Asp Thr His Met
770                 775                 780

Phe Lys Val Leu Phe Glu Pro Val Ala
785                 790

<210> SEQ ID NO 2
<211> LENGTH: 736
<212> TYPE: PRT
<213> ORGANISM: Artificial Sequence
<220> FEATURE:
<223> OTHER INFORMATION: Truncated copalyl diphosphate synthase

<400> SEQUENCE: 2

Met Ala Thr Val Asp Ala Pro Gln Val His Asp His Asp Gly Thr Thr
```

-continued

```
1               5                   10                  15
Val His Gln Gly His Asp Ala Val Lys Asn Ile Glu Asp Pro Ile Glu
                20                  25                  30

Tyr Ile Arg Thr Leu Leu Arg Thr Thr Gly Asp Gly Arg Ile Ser Val
                35                  40                  45

Ser Pro Tyr Asp Thr Ala Trp Val Ala Met Ile Lys Asp Val Glu Gly
    50                  55                  60

Arg Asp Gly Pro Gln Phe Pro Ser Ser Leu Glu Trp Ile Val Gln Asn
65                  70                  75                  80

Gln Leu Glu Asp Gly Ser Trp Gly Asp Gln Lys Leu Phe Cys Val Tyr
                85                  90                  95

Asp Arg Leu Val Asn Thr Ile Ala Cys Val Val Ala Leu Arg Ser Trp
                100                 105                 110

Asn Val His Ala His Lys Val Lys Arg Gly Val Thr Tyr Ile Lys Glu
                115                 120                 125

Asn Val Asp Lys Leu Met Glu Gly Asn Glu Glu His Met Thr Cys Gly
130                 135                 140

Phe Glu Val Val Phe Pro Ala Leu Leu Gln Lys Ala Lys Ser Leu Gly
145                 150                 155                 160

Ile Glu Asp Leu Pro Tyr Asp Ser Pro Ala Val Gln Glu Val Tyr His
                165                 170                 175

Val Arg Glu Gln Lys Leu Lys Arg Ile Pro Leu Glu Ile Met His Lys
                180                 185                 190

Ile Pro Thr Ser Leu Leu Phe Ser Leu Glu Gly Leu Glu Asn Leu Asp
                195                 200                 205

Trp Asp Lys Leu Leu Lys Leu Gln Ser Ala Asp Gly Ser Phe Leu Thr
210                 215                 220

Ser Pro Ser Ser Thr Ala Phe Ala Phe Met Gln Thr Lys Asp Glu Lys
225                 230                 235                 240

Cys Tyr Gln Phe Ile Lys Asn Thr Ile Asp Thr Phe Asn Gly Gly Ala
                245                 250                 255

Pro His Thr Tyr Pro Val Asp Val Phe Gly Arg Leu Trp Ala Ile Asp
                260                 265                 270

Arg Leu Gln Arg Leu Gly Ile Ser Arg Phe Phe Glu Pro Glu Ile Ala
                275                 280                 285

Asp Cys Leu Ser His Ile His Lys Phe Trp Thr Asp Lys Gly Val Phe
                290                 295                 300

Ser Gly Arg Glu Ser Glu Phe Cys Asp Ile Asp Asp Thr Ser Met Gly
305                 310                 315                 320

Met Arg Leu Met Arg Met His Gly Tyr Asp Val Asp Pro Asn Val Leu
                325                 330                 335

Arg Asn Phe Lys Gln Lys Asp Gly Lys Phe Ser Cys Tyr Gly Gly Gln
                340                 345                 350

Met Ile Glu Ser Pro Ser Pro Ile Tyr Asn Leu Tyr Arg Ala Ser Gln
                355                 360                 365

Leu Arg Phe Pro Gly Glu Glu Ile Leu Glu Asp Ala Lys Arg Phe Ala
                370                 375                 380

Tyr Asp Phe Leu Lys Glu Lys Leu Ala Asn Asn Gln Ile Leu Asp Lys
385                 390                 395                 400

Trp Val Ile Ser Lys His Leu Pro Asp Glu Ile Lys Leu Gly Leu Glu
                405                 410                 415

Met Pro Trp Leu Ala Thr Leu Pro Arg Val Glu Ala Lys Tyr Tyr Ile
                420                 425                 430
```

Gln Tyr Tyr Ala Gly Ser Gly Asp Val Trp Ile Gly Lys Thr Leu Tyr
                435                 440                 445

Arg Met Pro Glu Ile Ser Asn Asp Thr Tyr His Asp Leu Ala Lys Thr
450                 455                 460

Asp Phe Lys Arg Cys Gln Ala Lys His Gln Phe Glu Trp Leu Tyr Met
465                 470                 475                 480

Gln Glu Trp Tyr Glu Ser Cys Gly Ile Glu Glu Phe Gly Ile Ser Arg
                485                 490                 495

Lys Asp Leu Leu Leu Ser Tyr Phe Leu Ala Thr Ala Ser Ile Phe Glu
                500                 505                 510

Leu Glu Arg Thr Asn Glu Arg Ile Ala Trp Ala Lys Ser Gln Ile Ile
                515                 520                 525

Ala Lys Met Ile Thr Ser Phe Phe Asn Lys Glu Thr Thr Ser Glu Glu
                530                 535                 540

Asp Lys Arg Ala Leu Leu Asn Glu Leu Gly Asn Ile Asn Gly Leu Asn
545                 550                 555                 560

Asp Thr Asn Gly Ala Gly Arg Glu Gly Gly Ala Gly Ser Ile Ala Leu
                565                 570                 575

Ala Thr Leu Thr Gln Phe Leu Gly Phe Asp Arg Tyr Thr Arg His
                580                 585                 590

Gln Leu Lys Asn Ala Trp Ser Val Trp Leu Thr Gln Leu Gln His Gly
                595                 600                 605

Glu Ala Asp Asp Ala Glu Leu Leu Thr Asn Thr Leu Asn Ile Cys Ala
610                 615                 620

Gly His Ile Ala Phe Arg Glu Glu Ile Leu Ala His Asn Glu Tyr Lys
625                 630                 635                 640

Ala Leu Ser Asn Leu Thr Ser Lys Ile Cys Arg Gln Leu Ser Phe Ile
                645                 650                 655

Gln Ser Glu Lys Glu Met Gly Val Gly Glu Ile Ala Ala Lys Ser
                660                 665                 670

Ser Ile Lys Asn Lys Glu Leu Glu Glu Asp Met Gln Met Leu Val Lys
                675                 680                 685

Leu Val Leu Glu Lys Tyr Gly Gly Ile Asp Arg Asn Ile Lys Lys Ala
                690                 695                 700

Phe Leu Ala Val Ala Lys Thr Tyr Tyr Tyr Arg Ala Tyr His Ala Ala
705                 710                 715                 720

Asp Thr Ile Asp Thr His Met Phe Lys Val Leu Phe Glu Pro Val Ala
                725                 730                 735

<210> SEQ ID NO 3
<211> LENGTH: 2211
<212> TYPE: DNA
<213> ORGANISM: Artificial Sequence
<220> FEATURE:
<223> OTHER INFORMATION: Optimized cDNA for E. coli expression encoding
      for SmCPS2

<400> SEQUENCE: 3
atggcaactg ttgacgcacc tcaagtccat gatcacgatg gcaccaccgt tcaccagggt      60
cacgacgcgg tgaagaacat cgaggacccg atcgaataca ttcgtaccct gctgcgtacc     120
actggtgatg gtcgcatcag cgtcagcccg tatgacacgg cgtgggtggc gatgattaaa     180
gacgtcgagg gtcgcgatgg cccgcaattt ccttctagcc tggagtggat tgtccaaaat     240
cagctggaag atggctcgtg gggtgaccag aagctgtttt gtgtttacga tcgcctggtt     300

| | |
|---|---|
| aataccatcg catgtgtggt tgcgctgcgt agctggaatg ttcacgctca taaagtcaaa | 360 |
| cgtggcgtga cgtatatcaa ggaaaacgtg gataagctga tggaaggcaa cgaagaacac | 420 |
| atgacgtgtg gcttcgaggt tgttttttcca gccttgctgc agaaagcaaa gtccctgggt | 480 |
| attgaggatc tgccgtacga ctcgccggca gtgcaagaag tctatcacgt ccgcgagcag | 540 |
| aagctgaaac gcatcccgct ggagattatg cataagattc cgacctctct gctgttctct | 600 |
| ctggaaggtc tggagaacct ggattgggac aaactgctga gctgcagtc cgctgacggt | 660 |
| agctttctga ccagcccgag cagcacggcc tttgcgttta tgcagaccaa agatgagaag | 720 |
| tgctatcaat tcatcaagaa tactattgat accttcaacg gtggcgcacc gcacacgtac | 780 |
| ccagtagacg tttttggtcg cctgtgggcg attgaccgtt tgcagcgtct gggtatcagc | 840 |
| cgtttcttcg agccggagat tgcggactgc ttgagccata ttcacaaatt ctggacggac | 900 |
| aaaggcgtgt tcagcggtcg tgagagcgag ttctgcgaca tcgacgatac gagcatgggt | 960 |
| atgcgtctga tgcgtatgca cggttacgac gtggacccga atgtgttgcg caacttcaag | 1020 |
| caaaaagatg gcaagtttag ctgctacggt ggccaaatga ttgagagccc gagcccgatc | 1080 |
| tataacttat atcgtgcgag ccaactgcgt ttcccggggtg aagaaattct ggaagatgcg | 1140 |
| aagcgttttg cgtatgactt cctgaaggaa aagctcgcaa acaatcaaat cttggataaa | 1200 |
| tgggtgatca gcaagcactt gccggatgag attaaactgg gtctggagat gccgtggttg | 1260 |
| gccaccctgc cgagagttga ggcgaaatac tatattcagt attacgcggg tagcggtgat | 1320 |
| gtttggattg gcaagaccct gtaccgcatg ccggagatca gcaatgatac ctatcatgac | 1380 |
| ctggccaaga ccgacttcaa acgctgtcaa gcgaaacatc aatttgaatg gttatacatg | 1440 |
| caagagtggt acgaaagctg cggcatcgaa gagttcggta tctcccgtaa agatctgctg | 1500 |
| ctgtcttact ttctggcaac ggccagcatt ttcgagctgg agcgtaccaa tgagcgtatt | 1560 |
| gcctgggcga atcacaaat cattgctaag atgattacga gcttttttcaa taaagaaacc | 1620 |
| acgtccgagaa aagataaacg tgctctgctg aatgaactgg gcaacatcaa cggtctgaat | 1680 |
| gacaccaacg gtgccggtcg tgagggtggc gcaggcagca ttgcactggc cacgctgacc | 1740 |
| cagttcctgg aaggtttcga ccgctacacc cgtcaccagc tgaagaacgc gtggtccgtc | 1800 |
| tggctgaccc agctgcagca tggtgaggca gacgacgcgg agctgctgac caacacgttg | 1860 |
| aatatctgcg ctggccatat cgcgtttcgc gaagagattc tggcgcacaa cgagtacaaa | 1920 |
| gccctgagca atctgacctc taaaatctgt cgtcagctta gctttattca gagcgagaaa | 1980 |
| gaaatgggcg tggaaggtga gatcgcggca aaatccagca tcaagaacaa agaactggaa | 2040 |
| gaagatatgc agatgttggt caagctcgtc ctggagaagt atggtggcat cgaccgtaat | 2100 |
| atcaagaaag cgtttctggc cgtggcgaaa acgtattact accgcgcgta ccacgcggca | 2160 |
| gataccattg acacccacat gtttaaggtt ttgtttgagc cggttgctta a | 2211 |

<210> SEQ ID NO 4
<211> LENGTH: 575
<212> TYPE: PRT
<213> ORGANISM: Salvia sclarea

<400> SEQUENCE: 4

Met Ser Leu Ala Phe Asn Val Gly Val Thr Pro Phe Ser Gly Gln Arg
1               5                   10                  15

Val Gly Ser Arg Lys Glu Lys Phe Pro Val Gln Gly Phe Pro Val Thr
            20                  25                  30

Thr Pro Asn Arg Ser Arg Leu Ile Val Asn Cys Ser Leu Thr Thr Ile

```
                35                  40                  45
Asp Phe Met Ala Lys Met Lys Glu Asn Phe Lys Arg Glu Asp Asp Lys
 50                  55                  60

Phe Pro Thr Thr Thr Thr Leu Arg Ser Glu Asp Ile Pro Ser Asn Leu
 65                  70                  75                  80

Cys Ile Ile Asp Thr Leu Gln Arg Leu Gly Val Asp Gln Phe Phe Gln
                 85                  90                  95

Tyr Glu Ile Asn Thr Ile Leu Asp Asn Thr Phe Arg Leu Trp Gln Glu
                100                 105                 110

Lys His Lys Val Ile Tyr Gly Asn Val Thr Thr His Ala Met Ala Phe
                115                 120                 125

Arg Leu Leu Arg Val Lys Gly Tyr Glu Val Ser Ser Glu Glu Leu Ala
130                 135                 140

Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
                180                 185                 190

Lys Gln Val Gln Asp Asn Ser Ile Pro Asp Lys Lys Leu His Lys Leu
                195                 200                 205

Val Glu Phe Tyr Leu Arg Asn Tyr Lys Gly Ile Thr Ile Arg Leu Gly
210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
                260                 265                 270

Leu Gln Gln Leu Gln Arg Trp Tyr Ala Asp Cys Arg Leu Asp Thr Leu
                275                 280                 285

Asn Phe Gly Arg Asp Val Val Ile Ile Ala Asn Tyr Leu Ala Ser Leu
290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Asp Cys His Gly
                325                 330                 335

Ser Ser Gln Glu Cys Asp Lys Ile Ile Glu Leu Val Lys Glu Trp Lys
                340                 345                 350

Glu Asn Pro Asp Ala Glu Tyr Gly Ser Glu Glu Leu Glu Ile Leu Phe
                355                 360                 365

Met Ala Leu Tyr Asn Thr Val Asn Glu Leu Ala Glu Arg Ala Arg Val
                370                 375                 380

Glu Gln Gly Arg Ser Val Lys Glu Phe Leu Val Lys Leu Trp Val Glu
385                 390                 395                 400

Ile Leu Ser Ala Phe Lys Ile Glu Leu Asp Thr Trp Ser Asn Gly Thr
                405                 410                 415

Gln Gln Ser Phe Asp Glu Tyr Ile Ser Ser Ser Trp Leu Ser Asn Gly
                420                 425                 430

Ser Arg Leu Thr Gly Leu Leu Thr Met Gln Phe Val Gly Val Lys Leu
                435                 440                 445

Ser Asp Glu Met Leu Met Ser Glu Glu Cys Thr Asp Leu Ala Arg His
450                 455                 460
```

```
Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
                485                 490                 495

Thr Glu Lys Asp Gly Arg Lys Val Ser Glu Asp Glu Ala Ile Ala Glu
            500                 505                 510

Ile Asn Glu Met Val Glu Tyr His Trp Arg Lys Val Leu Gln Ile Val
        515                 520                 525

Tyr Lys Lys Glu Ser Ile Leu Pro Arg Arg Cys Lys Asp Val Phe Leu
530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Glu Asp Met Lys Ser Phe Val Phe
                565                 570                 575

<210> SEQ ID NO 5
<211> LENGTH: 525
<212> TYPE: PRT
<213> ORGANISM: Artificial Sequence
<220> FEATURE:
<223> OTHER INFORMATION: Truncated sclareol synthase from Salvia sclarea
      (SsScS)

<400> SEQUENCE: 5

Met Ala Lys Met Lys Glu Asn Phe Lys Arg Glu Asp Asp Lys Phe Pro
1               5                   10                  15

Thr Thr Thr Thr Leu Arg Ser Glu Asp Ile Pro Ser Asn Leu Cys Ile
                20                  25                  30

Ile Asp Thr Leu Gln Arg Leu Gly Val Asp Gln Phe Phe Gln Tyr Glu
            35                  40                  45

Ile Asn Thr Ile Leu Asp Asn Thr Phe Arg Leu Trp Gln Glu Lys His
        50                  55                  60

Lys Val Ile Tyr Gly Asn Val Thr Thr His Ala Met Ala Phe Arg Leu
65                  70                  75                  80

Leu Arg Val Lys Gly Tyr Glu Val Ser Ser Glu Glu Leu Ala Pro Tyr
                85                  90                  95

Gly Asn Gln Glu Ala Val Ser Gln Gln Thr Asn Asp Leu Pro Met Ile
            100                 105                 110

Ile Glu Leu Tyr Arg Ala Ala Asn Glu Arg Ile Tyr Glu Glu Arg
        115                 120                 125

Ser Leu Glu Lys Ile Leu Ala Trp Thr Thr Ile Phe Leu Asn Lys Gln
130                 135                 140

Val Gln Asp Asn Ser Ile Pro Asp Lys Lys Leu His Lys Leu Val Glu
145                 150                 155                 160

Phe Tyr Leu Arg Asn Tyr Lys Gly Ile Thr Ile Arg Leu Gly Ala Arg
                165                 170                 175

Arg Asn Leu Glu Leu Tyr Asp Met Thr Tyr Gln Ala Leu Lys Ser
            180                 185                 190

Thr Asn Arg Phe Ser Asn Leu Cys Asn Glu Asp Phe Leu Val Phe Ala
        195                 200                 205

Lys Gln Asp Phe Asp Ile His Glu Ala Gln Asn Lys Gly Leu Gln
            210                 215                 220

Gln Leu Gln Arg Trp Tyr Ala Asp Cys Arg Leu Asp Thr Leu Asn Phe
225                 230                 235                 240

Gly Arg Asp Val Val Ile Ile Ala Asn Tyr Leu Ala Ser Leu Ile Ile
```

```
            245                 250                 255
Gly Asp His Ala Phe Asp Tyr Val Arg Leu Ala Phe Ala Lys Thr Ser
            260                 265                 270

Val Leu Val Thr Ile Met Asp Asp Phe Phe Asp Cys His Gly Ser Ser
            275                 280                 285

Gln Glu Cys Asp Lys Ile Ile Glu Leu Val Lys Glu Trp Lys Glu Asn
        290                 295                 300

Pro Asp Ala Glu Tyr Gly Ser Glu Glu Leu Glu Ile Leu Phe Met Ala
305                 310                 315                 320

Leu Tyr Asn Thr Val Asn Glu Leu Ala Glu Arg Ala Arg Val Glu Gln
                325                 330                 335

Gly Arg Ser Val Lys Glu Phe Leu Val Lys Leu Trp Val Glu Ile Leu
            340                 345                 350

Ser Ala Phe Lys Ile Glu Leu Asp Thr Trp Ser Asn Gly Thr Gln Gln
            355                 360                 365

Ser Phe Asp Glu Tyr Ile Ser Ser Ser Trp Leu Ser Asn Gly Ser Arg
            370                 375                 380

Leu Thr Gly Leu Leu Thr Met Gln Phe Val Gly Val Lys Leu Ser Asp
385                 390                 395                 400

Glu Met Leu Met Ser Glu Cys Thr Asp Leu Ala Arg His Val Cys
                405                 410                 415

Met Val Gly Arg Leu Leu Asn Asp Val Cys Ser Ser Glu Arg Glu Arg
            420                 425                 430

Glu Glu Asn Ile Ala Gly Lys Ser Tyr Ser Ile Leu Leu Ala Thr Glu
            435                 440                 445

Lys Asp Gly Arg Lys Val Ser Glu Asp Glu Ala Ile Ala Glu Ile Asn
450                 455                 460

Glu Met Val Glu Tyr His Trp Arg Lys Val Leu Gln Ile Val Tyr Lys
465                 470                 475                 480

Lys Glu Ser Ile Leu Pro Arg Arg Cys Lys Asp Val Phe Leu Glu Met
            485                 490                 495

Ala Lys Gly Thr Phe Tyr Ala Tyr Gly Ile Asn Asp Glu Leu Thr Ser
            500                 505                 510

Pro Gln Gln Ser Lys Glu Asp Met Lys Ser Phe Val Phe
        515                 520                 525
```

<210> SEQ ID NO 6
<211> LENGTH: 1583
<212> TYPE: DNA
<213> ORGANISM: Artificial Sequence
<220> FEATURE:
<223> OTHER INFORMATION: Optimized cDNA for E. coli expression encoding the truncated sclareol synthase from Salvia sclarea

<400> SEQUENCE: 6

```
atggcgaaaa tgaaggagaa ctttaaacgc gaggacgata aattcccgac gaccacgacc        60
ctgcgcagcg aggatatccc gagcaacctg tgcatcattg taccctgca gcgcctgggt       120 gtcgatcagt tcttccaata cgaaatcaat accattctgg acaatacttt cgtctgtgg       180 caagagaaac acaaagtgat ctacggcaac gttaccaccc acgcgatggc gttccgtttg       240
ttgcgtgtca agggctacga ggtttccagc gaggaactgg cgccgtacgg taatcaggaa       300
gcagttagcc aacagacgaa tgatctgcct atgatcattg agctgtatcg cgcagcaaat       360
gagcgtatct acgaagagga acgcagcctg gaaaagatcc tggcgtggac cacgatcttc       420
ctgaacaaac aagttcaaga caattctatt cctgataaga agctgcataa actggtcgaa       480
```

-continued

```
ttctatctgc gtaattacaa gggcatcacg atccgtctgg gcgcacgccg taacctggag    540
ttgtatgata tgacgtatta ccaggctctg aaaagcacca atcgtttctc caatctgtgt    600
aatgaggatt ttctggtgtt cgccaagcag gattttgaca tccacgaggc gcaaaatcaa    660
aaaggtctgc aacaactgca acgttggtac gctgactgtc gcctggacac cctgaatttc    720
ggtcgcgacg ttgtcattat tgcaaactat ctggccagcc tgatcatcgg tgatcacgca    780
ttcgactacg tccgcctggc cttcgctaag accagcgttc tggtgaccat tatgatgat    840 ttcttcgatt gccacggttc tagccaggaa tgcgacaaaa tcattgagct ggtgaaagag    900
tggaaagaaa accctgatgc ggaataccgg tccgaagagt tggagatcct gtttatggcc    960
ttgtacaaca ccgtgaatga actggccgag cgtgctcgtg tggagcaggg ccgttctgtg    1020
aaggagtttt tggtcaagtt gtgggtggaa atcctgtccg cgttcaagat cgaactggat    1080
acgtggtcga atggtacgca acagagcttc gacgaataca tcagcagcag ctggctgagc    1140
aatggcagcc gtctgaccgg tttgctgacc atgcaatttg tgggtgttaa actgtccgat    1200
gaaatgctga tgagcgaaga atgcaccgac ctggcacgcc atgtgtgtat ggtgggtcgc    1260
ctgctgaacg acgtctgcag cagcgaacgt gagcgcgagg aaaacattgc aggcaagagc    1320
tacagcatct tgttggccac cgagaaagat ggtcgcaaag tgtctgagga cgaagcaatt    1380
gcagagatta tgaaatggt cgagtaccac tggcgtaagg ttttgcagat tgtgtataag    1440
aaagagagca tcttgccgcg tcgctgtaag gatgttttct tggagatggc gaagggcacg    1500
ttctatgcgt acggcattaa cgacgagctg acgagcccgc aacaatcgaa agaggacatg    1560
aagagcttcg tgttctgagg tac                                            1583
```

<210> SEQ ID NO 7
<211> LENGTH: 307
<212> TYPE: PRT
<213> ORGANISM: Pantoea agglomerans

<400> SEQUENCE: 7

```
Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175
```

```
Thr Pro Asp Ala Ile Leu Ser Thr Asn His Leu Lys Thr Gly Ile Leu
            180                 185                 190
Phe Ser Ala Met Leu Gln Ile Val Ala Ile Ala Ser Ala Ser Ser Pro
        195                 200                 205
Ser Thr Arg Glu Thr Leu His Ala Phe Ala Leu Asp Phe Gly Gln Ala
    210                 215                 220
Phe Gln Leu Leu Asp Asp Leu Arg Asp Asp His Pro Glu Thr Gly Lys
225                 230                 235                 240
Asp Arg Asn Lys Asp Ala Gly Lys Ser Thr Leu Val Asn Arg Leu Gly
                245                 250                 255
Ala Asp Ala Ala Arg Gln Lys Leu Arg Glu His Ile Asp Ser Ala Asp
            260                 265                 270
Lys His Leu Thr Phe Ala Cys Pro Gln Gly Gly Ala Ile Arg Gln Phe
        275                 280                 285
Met His Leu Trp Phe Gly His His Leu Ala Asp Trp Ser Pro Val Met
    290                 295                 300
Lys Ile Ala
305
```

<210> SEQ ID NO 8
<211> LENGTH: 924
<212> TYPE: DNA
<213> ORGANISM: Artificial Sequence
<220> FEATURE:
<223> OTHER INFORMATION: Optimized cDNA encoding for the GGPP synthase
      from Pantoea agglomerans

<400> SEQUENCE: 8

```
atggtttctg gttcgaaagc aggagtatca cctcataggg aaatcgaagt catgagacag      60
tccattgatg accacttagc aggattgttg ccagaaacag attcccagga tatcgttagc     120
cttgctatga gagaaggtgt tatggcacct ggtaaacgta tcagaccttt gctgatgtta     180
cttgctgcaa gagacctgag atatcagggt tctatgccta cactactgga tctagcttgt     240
gctgttgaac tgacacatac tgcttccttg atgctggatg acatgccttg tatggacaat     300
gcggaactta agagggtca accaacaacc cacaagaaat tcggagaatc tgttgccatt     360
ttggcttctg taggtctgtt gtcgaaagct tttggcttga ttgctgcaac tggtgatctt     420
ccaggtgaaa ggagagcaca agctgtaaac gagctatcta ctgcagttgg tgttcaaggt     480
ctagtcttag acagttcag agatttgaat gacgcagctt ggacagaaac tcctgatgct     540
atcctgtcta cgaaccatct gaagactggc atcttgttct cagctatgtt gcaaatcgta     600
gccattgctt ctgcttcttc accatctact agggaaacgt tacacgcatt cgcattggac     660
tttggtcaag cctttcaact gctagacgat ttgagggatg atcatccaga gacaggtaaa     720
gaccgtaaca agacgctgg taaaagcact ctagtcaaca gattgggtgc tgatgcagct     780
agacagaaac tgagagagca cattgactct gctgacaaac acctgacatt gcatgtccca     840
caaggaggtg ctataaggca gtttatgcac ctatggtttg gacaccatct tgctgattgg     900
tctccagtga tgaagatcgc ctaa                                            924
```

<210> SEQ ID NO 9
<211> LENGTH: 71
<212> TYPE: DNA
<213> ORGANISM: Artificial Sequence
<220> FEATURE:
<223> OTHER INFORMATION: Primer Sequence -continued

<400> SEQUENCE: 9
ctgtttgagc cggtcgccta aggtaccaga aggagataaa taatggcgaa atgaaggag     60 aactttaaac g                                                          71

<210> SEQ ID NO 10
<211> LENGTH: 55
<212> TYPE: DNA
<213> ORGANISM: Artificial Sequence
<220> FEATURE:
<223> OTHER INFORMATION: Primer Sequence

<400> SEQUENCE: 10
gcagcggttt ctttaccaga ctcgaggtca gaacacgaag ctcttcatgt cctct          55

<210> SEQ ID NO 11
<211> LENGTH: 786
<212> TYPE: PRT
<213> ORGANISM: Coleus forskohlii

<400> SEQUENCE: 11

```
Met Gly Ser Leu Ser Thr Met Asn Leu Asn His Ser Pro Met Ser Tyr
1               5                   10                  15

Ser Gly Ile Leu Pro Ser Ser Ala Lys Ala Lys Leu Leu Leu Leu Pro
            20                  25                  30

Gly Cys Phe Ser Ile Ser Ala Trp Met Asn Asn Gly Lys Asn Leu Asn
        35                  40                  45

Cys Gln Leu Thr His Lys Lys Ile Ser Lys Val Ala Glu Ile Arg Val
    50                  55                  60

Ala Thr Val Asn Ala Pro Pro Val His Asp Gln Asp Ser Thr Glu
65                  70                  75                  80

Asn Gln Cys His Asp Ala Val Asn Asn Ile Glu Asp Pro Ile Glu Tyr
                85                  90                  95

Ile Arg Thr Leu Leu Arg Thr Thr Gly Asp Gly Arg Ile Ser Val Ser
            100                 105                 110

Pro Tyr Asp Thr Ala Trp Val Ala Leu Ile Lys Asp Leu Gln Gly Arg
        115                 120                 125

Asp Ala Pro Glu Phe Pro Ser Ser Leu Glu Trp Ile Ile Gln Asn Gln
    130                 135                 140

Leu Ala Asp Gly Ser Trp Gly Asp Ala Lys Phe Phe Cys Val Tyr Asp
145                 150                 155                 160

Arg Leu Val Asn Thr Ile Ala Cys Val Val Ala Leu Arg Ser Trp Asp
                165                 170                 175

Val His Ala Glu Lys Val Glu Arg Gly Val Arg Tyr Ile Asn Glu Asn
            180                 185                 190

Val Glu Lys Leu Arg Asp Gly Asn Glu Glu His Met Thr Cys Gly Phe
        195                 200                 205

Glu Val Val Phe Pro Ala Leu Leu Gln Arg Ala Lys Ser Leu Gly Ile
    210                 215                 220

Gln Asp Leu Pro Tyr Asp Ala Pro Val Ile Gln Glu Ile Tyr His Ser
225                 230                 235                 240

Arg Glu Gln Lys Ser Lys Arg Ile Pro Leu Glu Met Met His Lys Val
                245                 250                 255

Pro Thr Ser Leu Leu Phe Ser Leu Glu Gly Leu Glu Asn Leu Glu Trp
            260                 265                 270

Asp Lys Leu Leu Lys Leu Gln Ser Ala Asp Gly Ser Phe Leu Thr Ser
        275                 280                 285
```

```
Pro Ser Ser Thr Ala Phe Ala Phe Met Gln Thr Arg Asp Pro Lys Cys
    290                 295                 300

Tyr Gln Phe Ile Lys Asn Thr Ile Gln Thr Phe Asn Gly Gly Ala Pro
305                 310                 315                 320

His Thr Tyr Pro Val Asp Val Phe Gly Arg Leu Trp Ala Ile Asp Arg
                325                 330                 335

Leu Gln Arg Leu Gly Ile Ser Arg Phe Phe Glu Ser Glu Ile Ala Asp
            340                 345                 350

Cys Ile Ala His Ile His Arg Phe Trp Thr Glu Lys Gly Val Phe Ser
        355                 360                 365

Gly Arg Glu Ser Glu Phe Cys Asp Ile Asp Asp Thr Ser Met Gly Val
    370                 375                 380

Arg Leu Met Arg Met His Gly Tyr Asp Val Asp Pro Asn Val Leu Lys
385                 390                 395                 400

Asn Phe Lys Lys Asp Asp Lys Phe Ser Cys Tyr Gly Gly Gln Met Ile
                405                 410                 415

Glu Ser Pro Ser Pro Ile Tyr Asn Leu Tyr Arg Ala Ser Gln Leu Arg
            420                 425                 430

Phe Pro Gly Glu Gln Ile Leu Glu Asp Ala Asn Lys Phe Ala Tyr Asp
        435                 440                 445

Phe Leu Gln Glu Lys Leu Ala His Asn Gln Ile Leu Asp Lys Trp Val
450                 455                 460

Ile Ser Lys His Leu Pro Asp Glu Ile Lys Leu Gly Leu Glu Met Pro
465                 470                 475                 480

Trp Tyr Ala Thr Leu Pro Arg Val Glu Ala Arg Tyr Tyr Ile Gln Tyr
                485                 490                 495

Tyr Ala Gly Ser Gly Asp Val Trp Ile Gly Lys Thr Leu Tyr Arg Met
            500                 505                 510

Pro Glu Ile Ser Asn Asp Thr Tyr His Glu Leu Ala Lys Thr Asp Phe
        515                 520                 525

Lys Arg Cys Gln Ala Gln His Gln Phe Glu Trp Ile Tyr Met Gln Glu
    530                 535                 540

Trp Tyr Glu Ser Cys Asn Met Glu Glu Phe Gly Ile Ser Arg Lys Glu
545                 550                 555                 560

Leu Leu Val Ala Tyr Phe Leu Ala Thr Ala Ser Ile Phe Glu Leu Glu
                565                 570                 575

Arg Ala Asn Glu Arg Ile Ala Trp Ala Lys Ser Gln Ile Ile Ser Thr
            580                 585                 590

Ile Ile Ala Ser Phe Phe Asn Asn Gln Asn Thr Ser Pro Glu Asp Lys
        595                 600                 605

Leu Ala Phe Leu Thr Asp Phe Lys Asn Gly Asn Ser Thr Asn Met Ala
    610                 615                 620

Leu Val Thr Leu Thr Gln Phe Leu Glu Gly Phe Asp Arg Tyr Thr Ser
625                 630                 635                 640

His Gln Leu Lys Asn Ala Trp Ser Val Trp Leu Arg Lys Leu Gln Gln
                645                 650                 655

Gly Glu Gly Asn Gly Gly Ala Asp Ala Glu Leu Leu Val Asn Thr Leu
            660                 665                 670

Asn Ile Cys Ala Gly His Ile Ala Phe Arg Glu Glu Ile Leu Ala His
        675                 680                 685

Asn Asp Tyr Lys Thr Leu Ser Asn Leu Thr Ser Lys Ile Cys Arg Gln
    690                 695                 700
```

```
Leu Ser Gln Ile Gln Asn Glu Lys Glu Leu Glu Thr Glu Gly Gln Lys
705                 710                 715                 720

Thr Ser Ile Lys Asn Lys Glu Leu Glu Asp Met Gln Arg Leu Val
            725                 730                 735

Lys Leu Val Leu Glu Lys Ser Arg Val Gly Ile Asn Arg Asp Met Lys
            740                 745                 750

Lys Thr Phe Leu Ala Val Val Lys Thr Tyr Tyr Lys Ala Tyr His
        755                 760                 765

Ser Ala Gln Ala Ile Asp Asn His Met Phe Lys Val Leu Phe Glu Pro
        770                 775                 780

Val Ala
785

<210> SEQ ID NO 12
<211> LENGTH: 724
<212> TYPE: PRT
<213> ORGANISM: Artificial Sequence
<220> FEATURE:
<223> OTHER INFORMATION: Truncated copalyl diphosphate synthase from
      Coleus forskohlii

<400> SEQUENCE: 12

Met Val Ala Thr Val Asn Ala Pro Pro Val His Asp Gln Asp Asp Ser
1               5                   10                  15

Thr Glu Asn Gln Cys His Asp Ala Val Asn Asn Ile Glu Asp Pro Ile
            20                  25                  30

Glu Tyr Ile Arg Thr Leu Leu Arg Thr Thr Gly Asp Gly Arg Ile Ser
        35                  40                  45

Val Ser Pro Tyr Asp Thr Ala Trp Val Ala Leu Ile Lys Asp Leu Gln
50                  55                  60

Gly Arg Asp Ala Pro Glu Phe Pro Ser Ser Leu Glu Trp Ile Ile Gln
65                  70                  75                  80

Asn Gln Leu Ala Asp Gly Ser Trp Gly Asp Ala Lys Phe Phe Cys Val
                85                  90                  95

Tyr Asp Arg Leu Val Asn Thr Ile Ala Cys Val Val Ala Leu Arg Ser
            100                 105                 110

Trp Asp Val His Ala Glu Lys Val Glu Arg Gly Val Arg Tyr Ile Asn
        115                 120                 125

Glu Asn Val Glu Lys Leu Arg Asp Gly Asn Glu His Met Thr Cys
130                 135                 140

Gly Phe Glu Val Val Phe Pro Ala Leu Leu Gln Arg Ala Lys Ser Leu
145                 150                 155                 160

Gly Ile Gln Asp Leu Pro Tyr Asp Ala Pro Val Ile Gln Glu Ile Tyr
                165                 170                 175

His Ser Arg Glu Gln Lys Ser Lys Arg Ile Pro Leu Glu Met Met His
            180                 185                 190

Lys Val Pro Thr Ser Leu Leu Phe Ser Leu Glu Gly Leu Glu Asn Leu
        195                 200                 205

Glu Trp Asp Lys Leu Leu Lys Leu Gln Ser Ala Asp Gly Ser Phe Leu
210                 215                 220

Thr Ser Pro Ser Ser Thr Ala Phe Ala Phe Met Gln Thr Arg Asp Pro
225                 230                 235                 240

Lys Cys Tyr Gln Phe Ile Lys Asn Thr Ile Gln Thr Phe Asn Gly Gly
                245                 250                 255

Ala Pro His Thr Tyr Pro Val Asp Val Phe Gly Arg Leu Trp Ala Ile
            260                 265                 270
```

```
Asp Arg Leu Gln Arg Leu Gly Ile Ser Arg Phe Phe Glu Ser Glu Ile
            275                 280                 285

Ala Asp Cys Ile Ala His Ile His Arg Phe Trp Thr Glu Lys Gly Val
290                 295                 300

Phe Ser Gly Arg Glu Ser Glu Phe Cys Asp Ile Asp Asp Thr Ser Met
305                 310                 315                 320

Gly Val Arg Leu Met Arg Met His Gly Tyr Asp Val Asp Pro Asn Val
                325                 330                 335

Leu Lys Asn Phe Lys Lys Asp Asp Lys Phe Ser Cys Tyr Gly Gly Gln
                340                 345                 350

Met Ile Glu Ser Pro Ser Pro Ile Tyr Asn Leu Tyr Arg Ala Ser Gln
            355                 360                 365

Leu Arg Phe Pro Gly Glu Gln Ile Leu Glu Asp Ala Asn Lys Phe Ala
370                 375                 380

Tyr Asp Phe Leu Gln Glu Lys Leu Ala His Asn Gln Ile Leu Asp Lys
385                 390                 395                 400

Trp Val Ile Ser Lys His Leu Pro Asp Glu Ile Lys Leu Gly Leu Glu
                405                 410                 415

Met Pro Trp Tyr Ala Thr Leu Pro Arg Val Glu Ala Arg Tyr Tyr Ile
            420                 425                 430

Gln Tyr Tyr Ala Gly Ser Gly Asp Val Trp Ile Gly Lys Thr Leu Tyr
            435                 440                 445

Arg Met Pro Glu Ile Ser Asn Asp Thr Tyr His Glu Leu Ala Lys Thr
            450                 455                 460

Asp Phe Lys Arg Cys Gln Ala Gln His Gln Phe Glu Trp Ile Tyr Met
465                 470                 475                 480

Gln Glu Trp Tyr Glu Ser Cys Asn Met Glu Glu Phe Gly Ile Ser Arg
                485                 490                 495

Lys Glu Leu Leu Val Ala Tyr Phe Leu Ala Thr Ala Ser Ile Phe Glu
                500                 505                 510

Leu Glu Arg Ala Asn Glu Arg Ile Ala Trp Ala Lys Ser Gln Ile Ile
            515                 520                 525

Ser Thr Ile Ile Ala Ser Phe Asn Asn Gln Asn Thr Ser Pro Glu
530                 535                 540

Asp Lys Leu Ala Phe Leu Thr Asp Phe Lys Asn Gly Asn Ser Thr Asn
545                 550                 555                 560

Met Ala Leu Val Thr Leu Thr Gln Phe Leu Glu Gly Phe Asp Arg Tyr
                565                 570                 575

Thr Ser His Gln Leu Lys Asn Ala Trp Ser Val Trp Leu Arg Lys Leu
            580                 585                 590

Gln Gln Gly Glu Gly Asn Gly Gly Ala Asp Ala Glu Leu Leu Val Asn
            595                 600                 605

Thr Leu Asn Ile Cys Ala Gly His Ile Ala Phe Arg Glu Glu Ile Leu
610                 615                 620

Ala His Asn Asp Tyr Lys Thr Leu Ser Asn Leu Thr Ser Lys Ile Cys
625                 630                 635                 640

Arg Gln Leu Ser Gln Ile Gln Asn Glu Lys Glu Leu Glu Thr Glu Gly
                645                 650                 655

Gln Lys Thr Ser Ile Lys Asn Lys Glu Leu Glu Glu Asp Met Gln Arg
            660                 665                 670

Leu Val Lys Leu Val Leu Glu Lys Ser Arg Val Gly Ile Asn Arg Asp
            675                 680                 685
```

```
Met Lys Lys Thr Phe Leu Ala Val Val Lys Thr Tyr Tyr Tyr Lys Ala
        690                 695                 700
Tyr His Ser Ala Gln Ala Ile Asp Asn His Met Phe Lys Val Leu Phe
705                 710                 715                 720
Glu Pro Val Ala

<210> SEQ ID NO 13
<211> LENGTH: 2175
<212> TYPE: DNA
<213> ORGANISM: Artificial Sequence
<220> FEATURE:
<223> OTHER INFORMATION: Optimized cDNA for E. coli expression encoding
      for CfCPS1-del63

<400> SEQUENCE: 13
```

| | | | | |
|---|---|---|---|---|
| atggtcgcta | ctgtcaatgc | tccaccggtc | cacgatcaag | acgacagcac tgagaatcaa | 60 |
| tgtcatgatg | ccgtaaacaa | tattgaagat | ccaatcgagt | atatccgtac cctgttgcgc | 120 |
| acgacgggtg | atggtcgtat | cagcgtcagc | ccgtacgata | ccgcgtgggt ggcgctgatc | 180 |
| aaagatctgc | agggccgtga | cgcaccggag | tttccgtcct | ctcttgagtg gatcattcaa | 240 |
| aaccagctgg | ccgacggttc | ttggggcgac | gccaaatttt | tctgcgtgta tgaccgtctg | 300 |
| gtgaacacca | tcgcgtgcgt | cgttgcgctg | cgttcctggg | acgtccacgc ggaaaaagtt | 360 |
| gagcgtggcg | tgcgctatat | caacgaaaat | gtcgaaaagc | tgcgcgacgg taatgaagaa | 420 |
| cacatgacct | gtggctttga | agttgttttc | ccggcgctcc | tgcagcgcgc gaagtctctg | 480 |
| ggtattcaag | atctgccgta | cgatgctccg | gtgatccaag | agatttatca ctctcgtgag | 540 |
| cagaagtcca | agcgtatccc | gttggagatg | atgcacaaag | ttccgacgag cctgctgttc | 600 |
| agcttggaag | gctggaaaa | tctggagtgg | gacaaactgc | tgaagctgca gagcgcggac | 660 |
| ggtagcttcc | tgacgagccc | gagcagcacc | gcatttgcat | ttatgcagac ccgtgacccg | 720 |
| aagtgttacc | aatttattaa | gaacacgatt | cagacgttta | cggtggtgc accgcatacc | 780 |
| tatccggtag | acgtctttgg | tcgcctgtgg | gcaattgatc | gtctgcagcg tttgggtatc | 840 |
| agccgcttct | tcgaaagcga | aattgcagat | tgtatcgcac | acatccatcg ttttggacc | 900 |
| gagaaaggcg | tctttagcgg | ccgtgagtct | gagttctgtg | acatcgatga cacgagcatg | 960 |
| ggtgtccgtc | tgatgcgtat | gcatggctat | gatgttgacc | cgaacgtgct gaagaatttt | 1020 |
| aaaaaagatg | acaagtttag | ctgctacggc | ggtcagatga | ttgagagccc gagcccgatt | 1080 |
| tataatctgt | accgcgcgag | ccaactgcgt | ttcccgggtg | aacagattct ggaagatgcc | 1140 |
| aataaattcg | cgtatgattt | cctgcaggaa | aaactggcgc | acaatcagat cctggataaa | 1200 |
| tgggttatca | gcaagcatct | gcctgacgaa | atcaaattgg | cctggagat gccgtggtat | 1260 |
| gcgaccttgc | cgcgtgtcga | agcgcgttac | tacatccagt | actatgcggg tagcggcgat | 1320 |
| gtctggattg | gtaagacgct | gtaccgtatg | ccagagatta | gcaacgacac ctaccatgaa | 1380 |
| ttggcaaaga | ccgatttcaa | gcgttgccaa | gcccaacacc | agttcgagtg gatttacatg | 1440 |
| caagagtggt | acgagtcgtg | caacatggaa | gagttcggta | ttagccgcaa agaactgctg | 1500 |
| gttgcatatt | tcctggccac | ggcgagcatc | tttgagctgg | agcgtgcgaa tgaacgcatt | 1560 |
| gcatgggcaa | aaagccaaat | catttctacc | attatcgctt | cgttctttaa taaccaaaat | 1620 |
| acgagccctg | aggataaact | ggcgtttctg | actgatttca | aaaatggcaa cagcaccaac | 1680 |
| atggctctgg | tgaccctgac | ccagttcctg | aaggctttg | accgctacac ttcccatcaa | 1740 |
| ctgaaaaacg | cgtggagcgt | ttggctgcgt | aagctgcaac | agggtgaggg taatggcggt | 1800 |

-continued

```
gccgacgccg agttactggt gaatacgctg aacatttgcg cgggtcacat cgcgttccgt    1860
gaagaaattc tggcacataa tgactataaa acgttgtcga acctgaccag caagatttgt    1920
cgccagctga ccagattca gaatgaaaaa gaattggaaa ccgaaggcca aaagacttcc    1980
attaagaaca aagaactgga agaagatatg cagcgcctgg ttaaactggt tttggagaaa    2040
agccgtgtgg gtatcaatcg tgacatgaag aaaacgttcc tggctgtggt gaaaacctac    2100
tattacaaag cataccactc cgcgcaggca atcgataacc acatgttcaa ggttctgttc    2160
gaaccggtgg cctaa                                                     2175
```

<210> SEQ ID NO 14
<211> LENGTH: 757
<212> TYPE: PRT
<213> ORGANISM: Triticum aestivum

<400> SEQUENCE: 14

```
Met Leu Thr Phe Thr Ala Ala Leu Arg His Val Pro Val Leu Asp Gln
1               5                   10                  15

Pro Thr Ser Glu Pro Trp Arg Arg Leu Ser Leu His Leu His Ser Gln
            20                  25                  30

Arg Arg Pro Cys Gly Leu Val Leu Ile Ser Lys Ser Pro Ser Tyr Pro
        35                  40                  45

Glu Val Asp Val Gly Glu Trp Lys Val Asp Glu Tyr Arg Gln Arg Thr
    50                  55                  60

Asp Glu Pro Ser Glu Thr Arg Gln Met Ile Asp Asp Ile Arg Thr Ala
65                  70                  75                  80

Leu Ala Ser Leu Gly Asp Asp Glu Thr Ser Met Ser Val Ser Ala Tyr
                85                  90                  95

Asp Thr Ala Leu Val Ala Leu Val Lys Asn Leu Asp Gly Gly Asp Gly
            100                 105                 110

Pro Gln Phe Pro Ser Cys Ile Asp Trp Ile Val Gln Asn Gln Leu Pro
        115                 120                 125

Asp Gly Ser Trp Gly Asp Pro Ala Phe Phe Met Val Gln Asp Arg Met
    130                 135                 140

Ile Ser Thr Leu Ala Cys Val Val Ala Val Lys Ser Trp Asn Ile Asp
145                 150                 155                 160

Arg Asp Asn Leu Cys Asp Arg Gly Val Leu Phe Ile Lys Glu Asn Met
                165                 170                 175

Ser Arg Leu Val Glu Glu Glu Gln Asp Trp Met Pro Cys Gly Phe Glu
            180                 185                 190

Ile Asn Phe Pro Ala Leu Leu Glu Lys Ala Lys Asp Leu Asp Leu Asp
        195                 200                 205

Ile Pro Tyr Asp His Pro Val Leu Glu Glu Ile Tyr Ala Lys Arg Asn
    210                 215                 220

Leu Lys Leu Leu Lys Ile Pro Leu Asp Val Leu His Ala Ile Pro Thr
225                 230                 235                 240

Thr Leu Leu Phe Ser Val Glu Gly Met Val Asp Leu Pro Leu Asp Trp
                245                 250                 255

Glu Lys Leu Leu Arg Leu Arg Cys Pro Asp Gly Ser Phe His Ser Ser
            260                 265                 270

Pro Ala Ala Thr Ala Ala Ala Leu Ser His Thr Gly Asp Lys Glu Cys
        275                 280                 285

His Ala Phe Leu Asp Arg Leu Ile Gln Lys Phe Glu Gly Gly Val Pro
    290                 295                 300
```

```
Cys Ser His Ser Met Asp Thr Phe Glu Gln Leu Trp Val Val Asp Arg
305                 310                 315                 320

Leu Met Arg Leu Gly Ile Ser Arg His Phe Thr Ser Glu Ile Gln Gln
            325                 330                 335

Cys Leu Glu Phe Ile Tyr Arg Arg Trp Thr Gln Lys Gly Leu Ala His
            340                 345                 350

Asn Met His Cys Pro Ile Pro Asp Ile Asp Asp Thr Ala Met Gly Phe
            355                 360                 365

Arg Leu Leu Arg Gln His Gly Tyr Asp Val Thr Pro Ser Val Phe Lys
370                 375                 380

His Phe Glu Lys Asp Gly Lys Phe Val Cys Phe Pro Met Glu Thr Asn
385                 390                 395                 400

His Ala Ser Val Thr Pro Met His Asn Thr Tyr Arg Ala Ser Gln Phe
                405                 410                 415

Met Phe Pro Gly Asp Asp Asp Val Leu Ala Arg Ala Gly Arg Tyr Cys
            420                 425                 430

Arg Ala Phe Leu Gln Glu Arg Gln Ser Ser Asn Lys Leu Tyr Asp Lys
            435                 440                 445

Trp Ile Ile Thr Lys Asp Leu Pro Gly Glu Val Gly Tyr Thr Leu Asn
450                 455                 460

Phe Pro Trp Lys Ser Ser Leu Pro Arg Ile Glu Thr Arg Met Tyr Leu
465                 470                 475                 480

Asp Gln Tyr Gly Gly Asn Asn Asp Val Trp Ile Ala Lys Val Leu Tyr
            485                 490                 495

Arg Met Asn Leu Val Ser Asn Asp Leu Tyr Leu Lys Met Ala Lys Ala
            500                 505                 510

Asp Phe Thr Glu Tyr Gln Arg Leu Ser Arg Ile Glu Trp Asn Gly Leu
            515                 520                 525

Arg Lys Trp Tyr Phe Arg Asn His Leu Gln Arg Tyr Gly Ala Thr Pro
            530                 535                 540

Lys Ser Ala Leu Lys Ala Tyr Phe Leu Ala Ser Ala Asn Ile Phe Glu
545                 550                 555                 560

Pro Gly Arg Ala Ala Glu Arg Leu Ala Trp Ala Arg Met Ala Val Leu
            565                 570                 575

Ala Glu Ala Val Thr Thr His Phe Arg His Ile Gly Gly Pro Cys Tyr
            580                 585                 590

Ser Thr Glu Asn Leu Glu Glu Leu Ile Asp Leu Val Ser Phe Asp Asp
            595                 600                 605

Val Ser Gly Gly Leu Arg Glu Ala Trp Lys Gln Trp Leu Met Ala Trp
            610                 615                 620

Thr Ala Lys Glu Ser His Gly Ser Val Asp Gly Asp Thr Ala Leu Leu
625                 630                 635                 640

Phe Val Arg Thr Ile Glu Ile Cys Ser Gly Arg Ile Val Ser Ser Glu
            645                 650                 655

Gln Lys Leu Asn Leu Trp Asp Tyr Ser Gln Leu Glu Gln Leu Thr Ser
            660                 665                 670

Ser Ile Cys His Lys Leu Ala Thr Ile Gly Leu Ser Gln Asn Glu Ala
            675                 680                 685

Ser Met Glu Asn Thr Glu Asp Leu His Gln Gln Val Asp Leu Glu Met
            690                 695                 700

Gln Glu Leu Ser Trp Arg Val His Gln Gly Cys His Gly Ile Asn Arg
705                 710                 715                 720

Glu Thr Arg Gln Thr Phe Leu Asn Val Val Lys Ser Phe Tyr Tyr Ser
```

```
                    725                 730                 735
Ala His Cys Ser Pro Glu Thr Val Asp Ser His Ile Ala Lys Val Ile
            740                 745                 750

Phe Gln Asp Val Ile
        755

<210> SEQ ID NO 15
<211> LENGTH: 699
<212> TYPE: PRT
<213> ORGANISM: Artificial Sequence
<220> FEATURE:
<223> OTHER INFORMATION: Truncated copalyl diphosphate synthase from
      Triticum aestivum

<400> SEQUENCE: 15

Met Tyr Arg Gln Arg Thr Asp Glu Pro Ser Glu Thr Arg Gln Met Ile
1               5                   10                  15

Asp Asp Ile Arg Thr Ala Leu Ala Ser Leu Gly Asp Asp Glu Thr Ser
            20                  25                  30

Met Ser Val Ser Ala Tyr Asp Thr Ala Leu Val Ala Leu Val Lys Asn
        35                  40                  45

Leu Asp Gly Gly Asp Gly Pro Gln Phe Pro Ser Cys Ile Asp Trp Ile
50                  55                  60

Val Gln Asn Gln Leu Pro Asp Gly Ser Trp Gly Asp Pro Ala Phe Phe
65                  70                  75                  80

Met Val Gln Asp Arg Met Ile Ser Thr Leu Ala Cys Val Val Ala Val
                85                  90                  95

Lys Ser Trp Asn Ile Asp Arg Asp Asn Leu Cys Asp Arg Gly Val Leu
            100                 105                 110

Phe Ile Lys Glu Asn Met Ser Arg Leu Val Glu Glu Glu Gln Asp Trp
        115                 120                 125

Met Pro Cys Gly Phe Glu Ile Asn Phe Pro Ala Leu Leu Glu Lys Ala
130                 135                 140

Lys Asp Leu Asp Leu Asp Ile Pro Tyr Asp His Pro Val Leu Glu Glu
145                 150                 155                 160

Ile Tyr Ala Lys Arg Asn Leu Lys Leu Leu Lys Ile Pro Leu Asp Val
                165                 170                 175

Leu His Ala Ile Pro Thr Thr Leu Leu Phe Ser Val Glu Gly Met Val
            180                 185                 190

Asp Leu Pro Leu Asp Trp Glu Lys Leu Leu Arg Leu Arg Cys Pro Asp
        195                 200                 205

Gly Ser Phe His Ser Ser Pro Ala Ala Thr Ala Ala Ala Leu Ser His
210                 215                 220

Thr Gly Asp Lys Glu Cys His Ala Phe Leu Asp Arg Leu Ile Gln Lys
225                 230                 235                 240

Phe Glu Gly Gly Val Pro Cys Ser His Ser Met Asp Thr Phe Glu Gln
                245                 250                 255

Leu Trp Val Val Asp Arg Leu Met Arg Leu Gly Ile Ser Arg His Phe
            260                 265                 270

Thr Ser Glu Ile Gln Gln Cys Leu Glu Phe Ile Tyr Arg Arg Trp Thr
        275                 280                 285

Gln Lys Gly Leu Ala His Asn Met His Cys Pro Ile Pro Asp Ile Asp
290                 295                 300

Asp Thr Ala Met Gly Phe Arg Leu Leu Arg Gln His Gly Tyr Asp Val
305                 310                 315                 320
```

Thr Pro Ser Val Phe Lys His Phe Glu Lys Asp Gly Lys Phe Val Cys
            325                 330                 335

Phe Pro Met Glu Thr Asn His Ala Ser Val Thr Pro Met His Asn Thr
        340                 345                 350

Tyr Arg Ala Ser Gln Phe Met Phe Pro Gly Asp Asp Val Leu Ala
    355                 360                 365

Arg Ala Gly Arg Tyr Cys Arg Ala Phe Leu Gln Glu Arg Gln Ser Ser
370                 375                 380

Asn Lys Leu Tyr Asp Lys Trp Ile Ile Thr Lys Asp Leu Pro Gly Glu
385                 390                 395                 400

Val Gly Tyr Thr Leu Asn Phe Pro Trp Lys Ser Ser Leu Pro Arg Ile
                405                 410                 415

Glu Thr Arg Met Tyr Leu Asp Gln Tyr Gly Gly Asn Asn Asp Val Trp
            420                 425                 430

Ile Ala Lys Val Leu Tyr Arg Met Asn Leu Val Ser Asn Asp Leu Tyr
        435                 440                 445

Leu Lys Met Ala Lys Ala Asp Phe Thr Glu Tyr Gln Arg Leu Ser Arg
    450                 455                 460

Ile Glu Trp Asn Gly Leu Arg Lys Trp Tyr Phe Arg Asn His Leu Gln
465                 470                 475                 480

Arg Tyr Gly Ala Thr Pro Lys Ser Ala Leu Lys Ala Tyr Phe Leu Ala
                485                 490                 495

Ser Ala Asn Ile Phe Glu Pro Gly Arg Ala Ala Glu Arg Leu Ala Trp
            500                 505                 510

Ala Arg Met Ala Val Leu Ala Glu Ala Val Thr Thr His Phe Arg His
        515                 520                 525

Ile Gly Gly Pro Cys Tyr Ser Thr Glu Asn Leu Glu Glu Leu Ile Asp
    530                 535                 540

Leu Val Ser Phe Asp Asp Val Ser Gly Gly Leu Arg Glu Ala Trp Lys
545                 550                 555                 560

Gln Trp Leu Met Ala Trp Thr Ala Lys Glu Ser His Gly Ser Val Asp
                565                 570                 575

Gly Asp Thr Ala Leu Leu Phe Val Arg Thr Ile Glu Ile Cys Ser Gly
            580                 585                 590

Arg Ile Val Ser Ser Glu Gln Lys Leu Asn Leu Trp Asp Tyr Ser Gln
        595                 600                 605

Leu Glu Gln Leu Thr Ser Ser Ile Cys His Lys Leu Ala Thr Ile Gly
    610                 615                 620

Leu Ser Gln Asn Glu Ala Ser Met Glu Asn Thr Glu Asp Leu His Gln
625                 630                 635                 640

Gln Val Asp Leu Glu Met Gln Glu Leu Ser Trp Arg Val His Gln Gly
                645                 650                 655

Cys His Gly Ile Asn Arg Glu Thr Arg Gln Thr Phe Leu Asn Val Val
            660                 665                 670

Lys Ser Phe Tyr Tyr Ser Ala His Cys Ser Pro Glu Thr Val Asp Ser
        675                 680                 685

His Ile Ala Lys Val Ile Phe Gln Asp Val Ile
    690                 695

<210> SEQ ID NO 16
<211> LENGTH: 2100
<212> TYPE: DNA
<213> ORGANISM: Artificial Sequence
<220> FEATURE:
<223> OTHER INFORMATION: Optimized cDNA for E. coli expression encoding for TaTps1-del59

<400> SEQUENCE: 16

```
atgtatcgcc aaagaactga tgagccaagc gaaacccgcc agatgatcga tgatattcgc      60
accgctttgg ctagcctggg tgacgatgaa accagcatga gcgtgagcgc atacgacacc     120
gccctggttg ccctggtgaa gaacctggac ggtggcgatg cccgcagtt cccgagctgc      180
attgactgga ttgttcagaa ccagctgccg gacggtagct ggggcgaccc ggctttcttt     240
atggttcagg accgtatgat cagcaccctg gcctgtgtcg tggccgtgaa atcctggaat     300
atcgatcgtg acaacttgtg cgatcgtggt gtcctgttta tcaaagaaaa catgtcgcgt     360
ctggttgaag aagaacaaga ttggatgcca tgtggcttcg agattaactt tcctgcactg     420
ttggagaaag ctaaagacct ggacttggac attccgtacg atcatcctgt gctggaagag     480
atttacgcga agcgtaatct gaaactgctg aagattccgt agatgtcct ccatgcgatc      540
ccgacgacgc tgttgttttc cgttgagggt atggtcgatc tgccgctgga ttgggagaaa     600
ctgctgcgtc tgcgttgccc ggacggttct tttcattcta gccggcggc gacggcagcg      660
gcgctgagcc acacgggtga caaagagtgt cacgccttcc tggaccgcct gattcaaaag     720
ttcgagggtg gcgtcccgtg ctcccacagc atggacacct cgagcaact gtgggttgtt      780
gaccgtttga tgcgtctggg tatcagccgt cattttacga gcagatcca gcagtgcttg      840
gagttcatct atcgtcgttg gacccagaaa ggtctggcgc acaatatgca ctgcccgatc     900
ccggacattg atgacactgc gatgggtttt cgtctgttga acagcacgg ttacgacgtg      960
accccgtcgg ttttcaagca tttcgagaaa gacggcaagt tcgtatgctt cccgatggaa    1020
accaaccatg cgagcgtgac gccgatgcac aatacctacc gtgcgagcca gttcatgttc    1080
ccgggtgatg acgacgtgct ggcccgtgcc ggccgctact gtcgcgcatt cttgcaagag    1140
cgtcagagct ctaacaagtt gtacgataag tggattatca cgaaagatct gccgggtgag    1200
gttggctaca cgctgaactt tccgtggaaa agctccctgc cgcgtattga aactcgtatg    1260
tatctggatc agtacggtgg caataacgat gtctggattg caaggtcct gtatcgcatg     1320
aacctggtta gcaatgacct gtacctgaaa atggcgaaag ccgactttac cgagtatcaa    1380
cgtctgtctc gcattgagtg gaacggcctg cgcaaatggt attttcgcaa tcatctgcag    1440
cgttacggtg cgaccccgaa gtccgcgctg aaagcgtatt tcctggcgtc ggcaaacatc    1500
tttgagcctg gccgcgcagc cgagcgcctg gcatgggcac gtatggccgt gctggctgaa    1560
gctgtaacga ctcatttccg tcacattggc ggcccgtgct acagcaccga gaatctggaa    1620
gaactgatcg accttgttag cttcgacgac gtgagcggcg gcttgcgtga ggcgtggaag    1680
caatggctga tggcgtggac cgcaaaagaa tcacacggca gcgtggacgg tgacacggca    1740
ctgctgtttg tccgcacgat tgagatttgc agcggccgca tcgtttccag cgagcagaaa    1800
ctgaatctgt gggattacag ccagttagag caattgacca gcagcatctg tcataaactg    1860
gccaccatcg gtctgagcca gaacgaagct agcatggaaa taccgaaga tctgcaccaa     1920
caagtcgatt tggaaatgca agaactgtca tggcgtgttc accagggttg tcacggtatt    1980
aatcgcgaaa cccgtcaaac cttcctgaat gttgttaagt cttttttatta ctccgcacac    2040
tgcagcccgg aaaccgtgga cagccatatt gcaaaagtga tctttcaaga cgttatctga    2100
```

<210> SEQ ID NO 17
<211> LENGTH: 785
<212> TYPE: PRT
<213> ORGANISM: Marrubium vulgare

<400> SEQUENCE: 17

Met Gly Ser Leu Ser Thr Leu Asn Leu Ile Lys Thr Cys Val Thr Leu
1               5                   10                  15

Ala Ser Ser Glu Lys Leu Asn Gln Pro Ser Gln Cys Tyr Thr Ile Ser
            20                  25                  30

Thr Cys Met Lys Ser Ser Asn Asn Pro Pro Phe Asn Tyr Tyr Gln Ile
        35                  40                  45

Asn Gly Arg Lys Lys Met Ser Thr Ala Ile Asp Ser Ser Val Asn Ala
    50                  55                  60

Pro Pro Glu Gln Lys Tyr Asn Ser Thr Ala Leu Glu His Asp Thr Glu
65              70                  75                  80

Ile Ile Glu Ile Glu Asp His Ile Glu Cys Ile Arg Arg Leu Leu Arg
                85                  90                  95

Thr Ala Gly Asp Gly Arg Ile Ser Val Ser Pro Tyr Asp Thr Ala Trp
            100                 105                 110

Ile Ala Leu Ile Lys Asp Leu Asp Gly His Asp Ser Pro Gln Phe Pro
        115                 120                 125

Ser Ser Met Glu Trp Val Ala Asp Asn Gln Leu Pro Asp Gly Ser Trp
    130                 135                 140

Gly Asp Glu His Phe Val Cys Val Tyr Asp Arg Leu Val Asn Thr Ile
145             150                 155                 160

Ala Cys Val Val Ala Leu Arg Ser Trp Asn Val His Ala His Lys Cys
                165                 170                 175

Glu Lys Gly Ile Lys Tyr Ile Lys Glu Asn Val His Lys Leu Glu Asp
            180                 185                 190

Ala Asn Glu Glu His Met Thr Cys Gly Phe Glu Val Val Phe Pro Ala
        195                 200                 205

Leu Leu Gln Arg Ala Gln Ser Met Gly Ile Lys Gly Ile Pro Tyr Asn
    210                 215                 220

Ala Pro Val Ile Glu Glu Ile Tyr Asn Ser Arg Glu Lys Lys Leu Lys
225             230                 235                 240

Arg Ile Pro Met Glu Val Val His Lys Val Ala Thr Ser Leu Leu Phe
                245                 250                 255

Ser Leu Glu Gly Leu Glu Asn Leu Glu Trp Glu Lys Leu Leu Lys Leu
            260                 265                 270

Gln Ser Pro Asp Gly Ser Phe Leu Thr Ser Pro Ser Ser Thr Ala Phe
        275                 280                 285

Ala Phe Ile His Thr Lys Asp Arg Lys Cys Phe Asn Phe Ile Asn Asn
    290                 295                 300

Ile Val His Thr Phe Lys Gly Gly Ala Pro His Thr Tyr Pro Val Asp
305             310                 315                 320

Ile Phe Gly Arg Leu Trp Ala Val Asp Arg Leu Gln Arg Leu Gly Ile
                325                 330                 335

Ser Arg Phe Phe Glu Ser Glu Ile Ala Glu Phe Leu Ser His Val His
            340                 345                 350

Arg Phe Trp Ser Asp Glu Ala Gly Val Phe Ser Gly Arg Glu Ser Val
        355                 360                 365

Phe Cys Asp Ile Asp Asp Thr Ser Met Gly Leu Arg Leu Leu Arg Met
    370                 375                 380

His Gly Tyr His Val Asp Pro Asn Val Leu Lys Asn Phe Lys Gln Ser
385             390                 395                 400

Asp Lys Phe Ser Cys Tyr Gly Gly Gln Met Met Glu Cys Ser Ser Pro

```
                405                 410                 415
Ile Tyr Asn Leu Tyr Arg Ala Ser Gln Leu Gln Phe Pro Gly Glu Glu
            420                 425                 430
Ile Leu Glu Glu Ala Asn Lys Phe Ala Tyr Lys Phe Leu Gln Glu Lys
        435                 440                 445
Leu Glu Ser Asn Gln Ile Leu Asp Lys Trp Leu Ile Ser Asn His Leu
    450                 455                 460
Ser Asp Glu Ile Lys Val Gly Leu Glu Met Pro Trp Tyr Ala Thr Leu
465                 470                 475                 480
Pro Arg Val Glu Thr Ser Tyr Tyr Ile His His Tyr Gly Gly Gly Asp
                485                 490                 495
Asp Val Trp Ile Gly Lys Thr Leu Tyr Arg Met Pro Glu Ile Ser Asn
            500                 505                 510
Asp Thr Tyr Arg Glu Leu Ala Arg Leu Asp Phe Arg Arg Cys Gln Ala
        515                 520                 525
Gln His Gln Leu Glu Trp Ile Tyr Met Gln Arg Trp Tyr Glu Ser Cys
    530                 535                 540
Arg Met Gln Glu Phe Gly Ile Ser Arg Lys Glu Val Leu Arg Ala Tyr
545                 550                 555                 560
Phe Leu Ala Ser Gly Thr Ile Phe Glu Val Glu Arg Ala Lys Glu Arg
                565                 570                 575
Val Ala Trp Ala Arg Ser Gln Ile Ile Ser His Met Ile Lys Ser Phe
            580                 585                 590
Phe Asn Lys Glu Thr Thr Ser Ser Asp Gln Lys Gln Ala Leu Leu Thr
        595                 600                 605
Glu Leu Leu Phe Gly Asn Ile Ser Ala Ser Glu Thr Glu Lys Arg Glu
    610                 615                 620
Leu Asp Gly Val Val Ala Thr Leu Arg Gln Phe Leu Glu Gly Phe
625                 630                 635                 640
Asp Ile Gly Thr Arg His Gln Val Lys Ala Ala Trp Asp Val Trp Leu
                645                 650                 655
Arg Lys Val Glu Gln Gly Glu Ala His Gly Gly Ala Asp Ala Glu Leu
            660                 665                 670
Cys Thr Thr Thr Leu Asn Thr Cys Ala Asn Gln His Leu Ser Ser His
        675                 680                 685
Pro Asp Tyr Asn Thr Leu Ser Lys Leu Thr Asn Lys Ile Cys His Lys
    690                 695                 700
Leu Ser Gln Ile Gln His Gln Lys Glu Met Lys Gly Gly Ile Lys Ala
705                 710                 715                 720
Lys Cys Ser Ile Asn Asn Lys Glu Val Asp Ile Glu Met Gln Trp Leu
                725                 730                 735
Val Lys Leu Val Leu Glu Lys Ser Gly Leu Asn Arg Lys Ala Lys Gln
            740                 745                 750
Ala Phe Leu Ser Ile Ala Lys Thr Tyr Tyr Arg Ala Tyr Tyr Ala
        755                 760                 765
Asp Gln Thr Met Asp Ala His Ile Phe Lys Val Leu Phe Glu Pro Val
    770                 775                 780
Val
785

<210> SEQ ID NO 18
<211> LENGTH: 723
<212> TYPE: PRT
<213> ORGANISM: Artificial Sequence
```

<220> FEATURE:
<223> OTHER INFORMATION: Truncated copalyl diphosphate synthase from
      Marrubium vulgare

<400> SEQUENCE: 18

| | | | | | | | | | | | | | | |
|---|---|---|---|---|---|---|---|---|---|---|---|---|---|---|
| Met | Ala | Pro | Pro | Glu | Gln | Lys | Tyr | Asn | Ser | Thr | Ala | Leu | Glu | His | Asp |
| 1 | | | | 5 | | | | | 10 | | | | | 15 | |

Thr Glu Ile Ile Glu Ile Glu Asp His Ile Glu Cys Ile Arg Arg Leu
              20                  25                  30

Leu Arg Thr Ala Gly Asp Gly Arg Ile Ser Val Ser Pro Tyr Asp Thr
         35                  40                  45

Ala Trp Ile Ala Leu Ile Lys Asp Leu Asp Gly His Asp Ser Pro Gln
 50                  55                  60

Phe Pro Ser Ser Met Glu Trp Val Ala Asp Asn Gln Leu Pro Asp Gly
 65                  70                  75                  80

Ser Trp Gly Asp Glu His Phe Val Cys Val Tyr Asp Arg Leu Val Asn
             85                  90                  95

Thr Ile Ala Cys Val Val Ala Leu Arg Ser Trp Asn Val His Ala His
            100                 105                 110

Lys Cys Glu Lys Gly Ile Lys Tyr Ile Lys Glu Asn Val His Lys Leu
        115                 120                 125

Glu Asp Ala Asn Glu Glu His Met Thr Cys Gly Phe Glu Val Val Phe
130                 135                 140

Pro Ala Leu Leu Gln Arg Ala Gln Ser Met Gly Ile Lys Gly Ile Pro
145                 150                 155                 160

Tyr Asn Ala Pro Val Ile Glu Glu Ile Tyr Asn Ser Arg Glu Lys Lys
                165                 170                 175

Leu Lys Arg Ile Pro Met Glu Val Val His Lys Val Ala Thr Ser Leu
            180                 185                 190

Leu Phe Ser Leu Glu Gly Leu Glu Asn Leu Glu Trp Glu Lys Leu Leu
        195                 200                 205

Lys Leu Gln Ser Pro Asp Gly Ser Phe Leu Thr Ser Pro Ser Ser Thr
210                 215                 220

Ala Phe Ala Phe Ile His Thr Lys Asp Arg Lys Cys Phe Asn Phe Ile
225                 230                 235                 240

Asn Asn Ile Val His Thr Phe Lys Gly Gly Ala Pro His Thr Tyr Pro
                245                 250                 255

Val Asp Ile Phe Gly Arg Leu Trp Ala Val Asp Arg Leu Gln Arg Leu
            260                 265                 270

Gly Ile Ser Arg Phe Phe Glu Ser Glu Ile Ala Glu Phe Leu Ser His
        275                 280                 285

Val His Arg Phe Trp Ser Asp Glu Ala Gly Val Phe Ser Gly Arg Glu
290                 295                 300

Ser Val Phe Cys Asp Ile Asp Asp Thr Ser Met Gly Leu Arg Leu Leu
305                 310                 315                 320

Arg Met His Gly Tyr His Val Asp Pro Asn Val Leu Lys Asn Phe Lys
                325                 330                 335

Gln Ser Asp Lys Phe Ser Cys Tyr Gly Gly Gln Met Met Glu Cys Ser
            340                 345                 350

Ser Pro Ile Tyr Asn Leu Tyr Arg Ala Ser Gln Leu Gln Phe Pro Gly
        355                 360                 365

Glu Glu Ile Leu Glu Glu Ala Asn Lys Phe Ala Tyr Lys Phe Leu Gln
370                 375                 380

Glu Lys Leu Glu Ser Asn Gln Ile Leu Asp Lys Trp Leu Ile Ser Asn

```
                385                 390                 395                 400
        His Leu Ser Asp Glu Ile Lys Val Gly Leu Glu Met Pro Trp Tyr Ala
                            405                 410                 415

Thr Leu Pro Arg Val Glu Thr Ser Tyr Tyr Ile His His Tyr Gly Gly
                            420                 425                 430

Gly Asp Asp Val Trp Ile Gly Lys Thr Leu Tyr Arg Met Pro Glu Ile
                            435                 440                 445

Ser Asn Asp Thr Tyr Arg Glu Leu Ala Arg Leu Asp Phe Arg Arg Cys
                            450                 455                 460

Gln Ala Gln His Gln Leu Glu Trp Ile Tyr Met Gln Arg Trp Tyr Glu
        465                 470                 475                 480

Ser Cys Arg Met Gln Glu Phe Gly Ile Ser Arg Lys Glu Val Leu Arg
                            485                 490                 495

Ala Tyr Phe Leu Ala Ser Gly Thr Ile Phe Glu Val Glu Arg Ala Lys
                            500                 505                 510

Glu Arg Val Ala Trp Ala Arg Ser Gln Ile Ile Ser His Met Ile Lys
                            515                 520                 525

Ser Phe Phe Asn Lys Glu Thr Thr Ser Ser Asp Gln Lys Gln Ala Leu
                            530                 535                 540

Leu Thr Glu Leu Leu Phe Gly Asn Ile Ser Ala Ser Glu Thr Glu Lys
        545                 550                 555                 560

Arg Glu Leu Asp Gly Val Val Val Ala Thr Leu Arg Gln Phe Leu Glu
                            565                 570                 575

Gly Phe Asp Ile Gly Thr Arg His Gln Val Lys Ala Ala Trp Asp Val
                            580                 585                 590

Trp Leu Arg Lys Val Glu Gln Gly Glu Ala His Gly Gly Ala Asp Ala
                            595                 600                 605

Glu Leu Cys Thr Thr Thr Leu Asn Thr Cys Ala Asn Gln His Leu Ser
                            610                 615                 620

Ser His Pro Asp Tyr Asn Thr Leu Ser Lys Leu Thr Asn Lys Ile Cys
        625                 630                 635                 640

His Lys Leu Ser Gln Ile Gln His Gln Lys Glu Met Lys Gly Gly Ile
                            645                 650                 655

Lys Ala Lys Cys Ser Ile Asn Asn Lys Glu Val Asp Ile Glu Met Gln
                            660                 665                 670

Trp Leu Val Lys Leu Val Leu Glu Lys Ser Gly Leu Asn Arg Lys Ala
                            675                 680                 685

Lys Gln Ala Phe Leu Ser Ile Ala Lys Thr Tyr Tyr Tyr Arg Ala Tyr
                            690                 695                 700

Tyr Ala Asp Gln Thr Met Asp Ala His Ile Phe Lys Val Leu Phe Glu
        705                 710                 715                 720

Pro Val Val
```

<210> SEQ ID NO 19
<211> LENGTH: 2172
<212> TYPE: DNA
<213> ORGANISM: Artificial Sequence
<220> FEATURE:
<223> OTHER INFORMATION: Optimized cDNA for E. coli expression encoding
      for MvCps3-del63

<400> SEQUENCE: 19
atggccccgc cggaacaaaa gtacaacagc actgcattag aacacgacac cgagattatt      60
gagatcgagg accacatcga gtgtatccgc cgtctgctgc gtaccgcggg tgatggtcgt     120

```
attagcgtga gcccgtatga taccgcgtgg attgcactga ttaaagattt ggatggccac      180
gactccccgc aattcccgtc gagcatggaa tgggttgctg ataatcagct gccggacggt      240
agctggggtg acgagcactt cgtttgcgtt tacgatcgcc tggttaatac catcgcatgc      300
gtcgtggcgc tgcgcagctg gaatgtccat gcacataagt gcgagaaagg tattaagtac      360
attaaagaaa atgtccacaa actggaagat gcgaacgaag aacacatgac ttgcggcttc      420
gaagtcgttt ttccggcctt gctgcagcgt gcacagagca tgggtattaa gggcatcccg      480
tacaacgcgc ctgtcattga agaaatttac aattcccgtg agaaaaagct gaaacgtatt      540
ccgatggaag ttgtccacaa agtcgcgacc agcctgctgt tctccctgga aggtctggag      600
aacctggagt gggagaaatt gctgaaactg cagagcccgg acggttcgtt tctgaccagc      660
ccgagctcta cggcattcgc gtttatccat accaaagacc gtaaatgttt taactttatt      720
aacaatatcg ttcatacctt taagggtggt gcaccgcaca cgtaccctgt ggacatcttt      780
ggccgcctgt gggcagtgga tcgcttgcag cgtctgggta ttagccgctt cttcgagagc      840
gagatcgcgg aatttctgag ccacgtgcac cgttttttga gcgacgaagc gggcgttttc      900
agcggccgtg agagcgtgtt ctgtgatatt gatgacacca gcatgggtct gcgcctgctt      960
cgtatgcatg gctaccatgt agacccaaac gttctgaaga acttcaagca atctgacaag     1020
tttagctgct acggtggcca gatgatggaa tgcagcagcc caatttacaa tctgtaccgt     1080
gcgagccaac tgcaatttcc gggtgaagaa atcttggaag aggctaacaa attcgcgtat     1140 aagttttttgc aagagaaact ggagtccaat cagattctgg acaagtggct gatctccaac     1200
cacctgagcg acgaaatcaa agttggcctg gaaatgccgt ggtatgcgac cttgccgcgc     1260
gttgagacta gctattatat tcaccattac ggcggtggcg acgatgtgtg gattggtaaa     1320
acgctgtatc gcatgccgga aattagcaac gacacctacc gtgagctggc acgtctggac     1380
ttccgccgct gccaggcgca gcaccagttg gaatggatct atatgcaacg ttggtatgag     1440
agctgtcgta tgcaagaatt tggtatttcc cgcaaagaag tcctgcgtgc ctacttcctg     1500
gcctctggca cgattttcga gttgagcgc gccaaagagc gcgtggcgtg ggctcgtagc     1560
caaatcattt cccacatgat caagagcttc ttcaataaag aaaccacgag cagcgatcag     1620
aaacaagcgc tgctgaccga gttgctgttt ggtaacatct ctgcaagcga gactgagaaa     1680
cgtgagctgg atggtgttgt ggttgcgacc ctgcgtcagt tcctggaagg cttcgatatc     1740
ggcacccgtc accaagtgaa ggcagcgtgg gatgtgtggc tgcgtaaagt cgaacagggt     1800
gaggcacatg gtggcgcgga cgccgagttg tgtacgacga cgctgaacac gtgcgcgaat     1860
cagcatctgt ctagccatcc ggactacaat accctgtcga aactcaccaa taagatttgt     1920
cacaagctgt cccaaatcca gcatcagaaa gaaatgaagg gcggtattaa ggcaaagtgc     1980
tctatcaata caaagaagt ggatatcgag atgcaatggc tggtcaaact ggtcctggag      2040
aaatccggtc tgaaccgcaa ggctaaacaa gcgtttctga gcattgccaa aacctattat     2100
tatcgtgctt actatgccga ccagacgatg gatgcccaca tcttcaaggt cctgtttgaa     2160
ccggtcgtgt aa                                                         2172
```

<210> SEQ ID NO 20
<211> LENGTH: 799
<212> TYPE: PRT
<213> ORGANISM: Rosmarinus officinalis

<400> SEQUENCE: 20

Met Thr Ser Met Ser Ser Leu Asn Leu Ser Arg Ala Pro Ala Ile Ser

```
1               5                   10                  15
Arg Arg Leu Gln Leu Pro Ala Lys Val Gln Leu Pro Glu Phe Tyr Ala
                20                  25                  30
Val Cys Ser Trp Leu Asn Asn Ser Lys His Thr Pro Leu Ser Cys
                35                  40                  45
His Ile His Arg Lys Gln Leu Ser Lys Val Thr Lys Cys Arg Val Ala
50                  55                  60
Ser Leu Asp Ala Ser Gln Val Ser Glu Lys Gly Thr Ser Ser Pro Val
65                  70                  75                  80
Gln Thr Pro Glu Glu Val Asn Glu Lys Ile Glu Asn Tyr Ile Glu Tyr
                85                  90                  95
Ile Lys Asn Leu Leu Thr Thr Ser Gly Asp Gly Arg Ile Ser Val Ser
                100                 105                 110
Pro Tyr Asp Thr Ser Ile Val Ala Leu Ile Lys Asp Leu Lys Gly Arg
                115                 120                 125
Asp Thr Pro Gln Phe Pro Ser Cys Leu Glu Trp Ile Ala Gln His Gln
130                 135                 140
Met Ala Asp Gly Ser Trp Gly Asp Glu Phe Phe Cys Ile Tyr Asp Arg
145                 150                 155                 160
Ile Leu Asn Thr Leu Ala Cys Val Val Ala Leu Lys Ser Trp Asn Val
                165                 170                 175
His Ala Asp Met Ile Glu Lys Gly Val Thr Tyr Val Asn Glu Asn Val
                180                 185                 190
Gln Lys Leu Glu Asp Gly Asn Leu Glu His Met Thr Ser Gly Phe Glu
                195                 200                 205
Ile Val Val Pro Ala Leu Val Gln Arg Ala Gln Asp Leu Gly Ile Gln
210                 215                 220
Gly Leu Pro Tyr Asp His Pro Leu Ile Lys Glu Ile Ala Asn Thr Lys
225                 230                 235                 240
Glu Gly Arg Leu Lys Lys Ile Pro Lys Asp Met Ile Tyr Gln Lys Pro
                245                 250                 255
Thr Thr Leu Leu Phe Ser Leu Glu Gly Leu Gly Asp Leu Glu Trp Glu
                260                 265                 270
Lys Ile Leu Lys Leu Gln Ser Gly Asp Gly Ser Phe Leu Thr Ser Pro
                275                 280                 285
Ser Ser Thr Ala His Val Phe Met Lys Thr Lys Asp Glu Lys Cys Leu
                290                 295                 300
Lys Phe Ile Glu Asn Ala Val Lys Asn Cys Asn Gly Gly Ala Pro His
305                 310                 315                 320
Thr Tyr Pro Val Asp Val Phe Ala Arg Leu Trp Ala Val Asp Arg Leu
                325                 330                 335
Gln Arg Leu Gly Ile Ser Arg Phe Phe Gln Gln Glu Ile Lys Tyr Phe
                340                 345                 350
Leu Asp His Ile Asn Ser Val Trp Thr Glu Asn Gly Val Phe Ser Gly
                355                 360                 365
Arg Asp Ser Glu Phe Cys Asp Ile Asp Asp Thr Ser Met Gly Ile Arg
                370                 375                 380
Leu Leu Lys Met His Gly Tyr Asp Ile Asp Pro Asn Ala Leu Glu His
385                 390                 395                 400
Phe Lys Gln Gln Asp Gly Lys Phe Ser Cys Tyr Gly Gly Gln Met Ile
                405                 410                 415
Glu Ser Ala Ser Pro Ile Tyr Asn Leu Tyr Arg Ala Ala Gln Leu Arg
                420                 425                 430
```

-continued

Phe Pro Gly Glu Glu Ile Leu Glu Glu Ala Thr Lys Phe Ala Tyr Asn
            435                 440                 445

Phe Leu Gln Glu Lys Ile Ala Asn Asp Gln Phe Gln Glu Lys Trp Val
        450                 455                 460

Ile Ser Asp His Leu Ile Asp Glu Val Lys Leu Gly Leu Lys Met Pro
465                 470                 475                 480

Trp Tyr Ala Thr Leu Pro Arg Val Glu Ala Ala Tyr Tyr Leu Gln Tyr
                485                 490                 495

Tyr Ala Gly Cys Gly Asp Val Trp Ile Gly Lys Val Phe Tyr Arg Met
                500                 505                 510

Pro Glu Ile Ser Asn Asp Thr Tyr Lys Lys Leu Ala Ile Leu Asp Phe
                515                 520                 525

Asn Arg Cys Gln Ala Gln His Gln Phe Glu Trp Ile Tyr Met Gln Glu
            530                 535                 540

Trp Tyr His Arg Ser Ser Val Ser Glu Phe Gly Ile Ser Lys Lys Asp
545                 550                 555                 560

Leu Leu Arg Ala Tyr Phe Leu Ala Ala Ala Thr Ile Phe Glu Pro Glu
                565                 570                 575

Arg Thr Gln Glu Arg Leu Val Trp Ala Lys Thr Gln Ile Val Ser Gly
            580                 585                 590

Met Ile Thr Ser Phe Val Asn Ser Gly Thr Thr Leu Ser Leu His Gln
                595                 600                 605

Lys Thr Ala Leu Leu Ser Gln Ile Gly His Asn Phe Asp Gly Leu Asp
            610                 615                 620

Glu Ile Ile Ser Ala Met Lys Asp His Gly Leu Ala Ala Thr Leu Leu
625                 630                 635                 640

Thr Thr Phe Gln Gln Leu Leu Asp Gly Phe Asp Arg Tyr Thr Arg His
                645                 650                 655

Gln Leu Lys Asn Ala Trp Ser Gln Trp Phe Met Lys Leu Gln Gln Gly
            660                 665                 670

Glu Ala Ser Gly Gly Glu Asp Ala Glu Leu Leu Ala Asn Thr Leu Asn
            675                 680                 685

Ile Cys Ala Gly Leu Ile Ala Phe Asn Glu Asp Val Leu Ser His His
            690                 695                 700

Glu Tyr Thr Thr Leu Ser Thr Leu Thr Asn Lys Ile Cys Lys Arg Leu
705                 710                 715                 720

Thr Gln Ile Gln Asp Lys Lys Thr Leu Glu Val Val Asp Gly Ser Ile
                725                 730                 735

Lys Asp Lys Glu Leu Glu Lys Asp Ile Gln Met Leu Val Lys Leu Val
                740                 745                 750

Leu Glu Glu Asn Gly Gly Gly Val Asp Arg Asn Ile Lys His Thr Phe
            755                 760                 765

Leu Ser Val Phe Lys Thr Phe Tyr Tyr Asn Ala Tyr His Asp Asp Glu
770                 775                 780

Thr Thr Asp Val His Ile Phe Lys Val Leu Phe Gly Pro Val Val
785                 790                 795

<210> SEQ ID NO 21
<211> LENGTH: 733
<212> TYPE: PRT
<213> ORGANISM: Artificial Sequence
<220> FEATURE:
<223> OTHER INFORMATION: Truncated copalyl diphosphate synthase from
      Rosmarinus officinalis

<400> SEQUENCE: 21

```
Met Ala Ser Gln Val Ser Glu Lys Gly Thr Ser Ser Pro Val Gln Thr
1               5                   10                  15

Pro Glu Glu Val Asn Glu Lys Ile Glu Asn Tyr Ile Glu Tyr Ile Lys
            20                  25                  30

Asn Leu Leu Thr Thr Ser Gly Asp Gly Arg Ile Ser Val Ser Pro Tyr
        35                  40                  45

Asp Thr Ser Ile Val Ala Leu Ile Lys Asp Leu Lys Gly Arg Asp Thr
    50                  55                  60

Pro Gln Phe Pro Ser Cys Leu Glu Trp Ile Ala Gln His Gln Met Ala
65                  70                  75                  80

Asp Gly Ser Trp Gly Asp Glu Phe Phe Cys Ile Tyr Asp Arg Ile Leu
                85                  90                  95

Asn Thr Leu Ala Cys Val Val Ala Leu Lys Ser Trp Asn Val His Ala
            100                 105                 110

Asp Met Ile Glu Lys Gly Val Thr Tyr Val Asn Glu Asn Val Gln Lys
        115                 120                 125

Leu Glu Asp Gly Asn Leu Glu His Met Thr Ser Gly Phe Glu Ile Val
    130                 135                 140

Val Pro Ala Leu Val Gln Arg Ala Gln Asp Leu Gly Ile Gln Gly Leu
145                 150                 155                 160

Pro Tyr Asp His Pro Leu Ile Lys Glu Ile Ala Asn Thr Lys Glu Gly
                165                 170                 175

Arg Leu Lys Lys Ile Pro Lys Asp Met Ile Tyr Gln Lys Pro Thr Thr
            180                 185                 190

Leu Leu Phe Ser Leu Glu Gly Leu Gly Asp Leu Glu Trp Glu Lys Ile
        195                 200                 205

Leu Lys Leu Gln Ser Gly Asp Gly Ser Phe Leu Thr Ser Pro Ser Ser
    210                 215                 220

Thr Ala His Val Phe Met Lys Thr Lys Asp Glu Lys Cys Leu Lys Phe
225                 230                 235                 240

Ile Glu Asn Ala Val Lys Asn Cys Asn Gly Gly Ala Pro His Thr Tyr
                245                 250                 255

Pro Val Asp Val Phe Ala Arg Leu Trp Ala Val Asp Arg Leu Gln Arg
            260                 265                 270

Leu Gly Ile Ser Arg Phe Phe Gln Gln Glu Ile Lys Tyr Phe Leu Asp
        275                 280                 285

His Ile Asn Ser Val Trp Thr Glu Asn Gly Val Phe Ser Gly Arg Asp
    290                 295                 300

Ser Glu Phe Cys Asp Ile Asp Asp Thr Ser Met Gly Ile Arg Leu Leu
305                 310                 315                 320

Lys Met His Gly Tyr Asp Ile Asp Pro Asn Ala Leu Glu His Phe Lys
                325                 330                 335

Gln Gln Asp Gly Lys Phe Ser Cys Tyr Gly Gly Gln Met Ile Glu Ser
            340                 345                 350

Ala Ser Pro Ile Tyr Asn Leu Tyr Arg Ala Ala Gln Leu Arg Phe Pro
        355                 360                 365

Gly Glu Glu Ile Leu Glu Glu Ala Thr Lys Phe Ala Tyr Asn Phe Leu
    370                 375                 380

Gln Glu Lys Ile Ala Asn Asp Gln Phe Gln Glu Lys Trp Val Ile Ser
385                 390                 395                 400

Asp His Leu Ile Asp Glu Val Lys Leu Gly Leu Lys Met Pro Trp Tyr
                405                 410                 415
```

```
Ala Thr Leu Pro Arg Val Glu Ala Ala Tyr Tyr Leu Gln Tyr Tyr Ala
            420                 425                 430

Gly Cys Gly Asp Val Trp Ile Gly Lys Val Phe Tyr Arg Met Pro Glu
            435                 440                 445

Ile Ser Asn Asp Thr Tyr Lys Lys Leu Ala Ile Leu Asp Phe Asn Arg
        450                 455                 460

Cys Gln Ala Gln His Gln Phe Glu Trp Ile Tyr Met Gln Glu Trp Tyr
465                 470                 475                 480

His Arg Ser Ser Val Ser Glu Phe Gly Ile Ser Lys Lys Asp Leu Leu
                485                 490                 495

Arg Ala Tyr Phe Leu Ala Ala Thr Ile Phe Glu Pro Glu Arg Thr
            500                 505                 510

Gln Glu Arg Leu Val Trp Ala Lys Thr Gln Ile Val Ser Gly Met Ile
            515                 520                 525

Thr Ser Phe Val Asn Ser Gly Thr Thr Leu Ser Leu His Gln Lys Thr
    530                 535                 540

Ala Leu Leu Ser Gln Ile Gly His Asn Phe Asp Gly Leu Asp Glu Ile
545                 550                 555                 560

Ile Ser Ala Met Lys Asp His Gly Leu Ala Ala Thr Leu Leu Thr Thr
                565                 570                 575

Phe Gln Gln Leu Leu Asp Gly Phe Asp Arg Tyr Thr Arg His Gln Leu
            580                 585                 590

Lys Asn Ala Trp Ser Gln Trp Phe Met Lys Leu Gln Gln Gly Glu Ala
            595                 600                 605

Ser Gly Gly Glu Asp Ala Glu Leu Leu Ala Asn Thr Leu Asn Ile Cys
    610                 615                 620

Ala Gly Leu Ile Ala Phe Asn Glu Asp Val Leu Ser His His Glu Tyr
625                 630                 635                 640

Thr Thr Leu Ser Thr Leu Thr Asn Lys Ile Cys Lys Arg Leu Thr Gln
                645                 650                 655

Ile Gln Asp Lys Lys Thr Leu Glu Val Val Asp Gly Ser Ile Lys Asp
            660                 665                 670

Lys Glu Leu Glu Lys Asp Ile Gln Met Leu Val Lys Leu Val Leu Glu
        675                 680                 685

Glu Asn Gly Gly Gly Val Asp Arg Asn Ile Lys His Thr Phe Leu Ser
    690                 695                 700

Val Phe Lys Thr Phe Tyr Tyr Asn Ala Tyr His Asp Asp Glu Thr Thr
705                 710                 715                 720

Asp Val His Ile Phe Lys Val Leu Phe Gly Pro Val Val
                725                 730
```

<210> SEQ ID NO 22
<211> LENGTH: 2202
<212> TYPE: DNA
<213> ORGANISM: Artificial Sequence
<220> FEATURE:
<223> OTHER INFORMATION: Optimized cDNA for E. coli expression encoding
      for RoCPS1-del67

<400> SEQUENCE: 22
atggcatcac aagttagcga gaaaggcacc agctccccag ttcaaacgcc agaggaagtg    60
aacgaaaaga tcgagaatta cattgagtat attaaaaatc tgctgactac ttcgggcgac   120
ggccgcatca gcgtcagccc gtacgacacg agcatcgttg ccctgattaa agacctgaag   180
ggtcgtgaca ccccgcagtt tccgtcctgt ctggagtgga ttgcccaaca ccaaatggcc   240

```
gatggttcct ggggtgatga attttctgc atttacgacc gcatcctgaa tacgctggct     300
tgtgttgtcg ccctgaagtc ctggaatgtt catgcagaca tgatcgaaaa gggtgtcact     360
tacgttaacg aaaacgtgca gaaactggaa gatggcaatc tggagcacat gacgagcggt     420
ttcgagattg ttgtcccggc gctggttcag agagcgcaag acctgggcat ccagggcctg     480
ccgtatgatc atccgttgat caaagaaatc gcaaacacca agagggccg cctgaagaaa     540 attcctaaag acatgattta tcagaaaccg actacgctgc tgttcagcct ggaaggcttg     600
ggcgacctgg agtgggaaaa gatcctgaag ttacagtctg gtgatggttc tttcctgacc     660
agcccgagct ctacgcccca tgttttcatg aaaaccaaag atgagaagtg tctgaagttt     720
attgaaaatg ccgtcaagaa ttgcaacggt ggcgcgcctc acacctaccc ggtggacgtt     780
ttcgctcgtc tgtgggccgt cgatcgtctg aacgcctgg gcatctcgcg tttcttccag     840
caagagatta agtacttcct ggaccacatt aatagcgtgt ggaccgaaaa cggcgttttc     900
agcggtcgcg acagcgagtt tgtgatatt gatgacacct ctatgggtat ccgtttgctg     960
aagatgcacg gttacgacat tgacccgaat gccctggagc actttaaaca acaggatggt    1020
aagttctcct gctacggtgg tcagatgatt gagagcgcga gccgatcta caacctgtac    1080 cgtgctgcgc agctgcgttt tccgggtgaa gagattctgg aagaggccac caaatttgcg    1140 tataatttt tgcaagagaa aattgcaaac gaccaattcc aggaaaaatg ggttattagc    1200
gatcacctta tcgatgaagt gaaactgggt ttgaagatgc cgtggtacgc gacgctgcca    1260
cgtgtcgagg cagcgtatta tctgcagtat tatgcgggct gtggtgatgt gtggatcggc    1320
aaagtgttct accgtatgcc ggaaatcagc aatgacacct acaagaaact ggccatcctg    1380
gatttcaacc gttgccaggc gcaacaccaa ttcgagtgga tctacatgca agagtggtat    1440
catcgtagca gcgtttctga gtttggcatt tccaaaaaag acttgctgcg cgcgtatttt    1500
ctggcggcag cgaccatttt cgaaccggag cgcacccagg aacgtctggt gtgggctaag    1560
acgcaaatcg tcagcggtat gattacgtcc tttgttaata gcggtacgac tctgagcctg    1620
caccagaaaa cggcactgtt gagccaaatc ggtcataact ttgacggcct ggatgagatt    1680
atcagcgcga tgaaagacca cggcctggca gcgacgctgt taacgacctt caacagctg    1740 ctggacggct tcgatcgcta cacccgtcat cagctgaaaa acgcgtggag ccagtggttc    1800
atgaagctgc aacagggtga ggcgtcgggt ggcgaagatg ctgagctgct ggctaatacc    1860
ctgaacattt gcgcgggttt gattgcgttt aatgaagatg tgttgagcca ccatgagtac    1920
accaccctga gcaccctgac caacaagatc tgtaagcgct tgactcaaat ccaggataag    1980
aaaacgctgg aagtcgtgga tggtagcatc aaagataaag aactggaaaa agacattcaa    2040
atgctggtga aactggtcct tgaagagaac ggcggtggcg ttgaccgtaa catcaagcac    2100
accttcctga gcgtctttaa aacctttat tataatgcct atcatgacga tgaaacgacc    2160
gacgtgcaca ttttcaaagt tctgttcggt ccggtcgtgt aa                       2202
```

<210> SEQ ID NO 23  
<211> LENGTH: 766  
<212> TYPE: PRT  
<213> ORGANISM: Artificial Sequence  
<220> FEATURE:  
<223> OTHER INFORMATION: Truncated putative sclareol synthase from Nicotiana glutinosa

<400> SEQUENCE: 23

Met Ala Asn Phe His Arg Pro Ser Arg Val Arg Cys Ser His Ser Thr

-continued

```
1               5                   10                  15
Ala Ser Ser Leu Glu Glu Ala Lys Glu Arg Ile Arg Glu Thr Phe Gly
            20                  25                  30

Lys Asn Glu Leu Ser Pro Ser Ser Tyr Asp Thr Ala Trp Val Ala Met
            35                  40                  45

Val Pro Ser Arg Tyr Ser Met Asn Gln Pro Cys Phe Pro Arg Cys Leu
        50                  55                  60

Asp Trp Ile Leu Glu Asn Gln Arg Glu Asp Gly Ser Trp Gly Leu Asn
65                  70                  75                  80

Pro Ser His Pro Leu Leu Val Lys Asp Ser Leu Ser Ser Thr Leu Ala
                85                  90                  95

Cys Leu Leu Ala Leu Arg Lys Trp Arg Ile Gly Asp Asn Gln Val Gln
            100                 105                 110

Arg Gly Leu Gly Phe Ile Glu Thr His Gly Trp Ala Val Asp Asn Val
            115                 120                 125

Asp Gln Ile Ser Pro Leu Gly Phe Asp Ile Ile Phe Pro Ser Met Ile
            130                 135                 140

Lys Tyr Ala Glu Lys Leu Asn Leu Asp Leu Pro Phe Asp Pro Asn Leu
145                 150                 155                 160

Val Asn Met Met Leu Arg Glu Arg Glu Leu Thr Ile Glu Arg Ala Leu
                165                 170                 175

Lys Asn Glu Phe Glu Gly Asn Met Ala Asn Val Glu Tyr Phe Ala Glu
            180                 185                 190

Gly Leu Gly Glu Leu Cys His Trp Lys Glu Ile Met Leu His Gln Arg
            195                 200                 205

Arg Asn Gly Ser Leu Phe Asp Ser Pro Ala Thr Thr Ala Ala Ala Leu
            210                 215                 220

Ile Tyr His Gln His Asp Glu Lys Cys Phe Gly Tyr Leu Ser Ser Ile
225                 230                 235                 240

Leu Lys Leu His Glu Asn Trp Val Pro Thr Ile Tyr Pro Thr Lys Val
                245                 250                 255

His Ser Asn Leu Phe Phe Val Asp Ala Leu Gln Asn Leu Gly Val Asp
            260                 265                 270

Arg Tyr Phe Lys Thr Glu Leu Lys Ser Val Leu Asp Glu Ile Tyr Arg
            275                 280                 285

Leu Trp Leu Glu Lys Asn Glu Glu Ile Phe Ser Asp Ile Ala His Cys
            290                 295                 300

Ala Met Ala Phe Arg Leu Leu Arg Met Asn Asn Tyr Glu Val Ser Ser
305                 310                 315                 320

Glu Glu Leu Glu Gly Phe Val Asp Gln Glu His Phe Phe Thr Thr Ser
            325                 330                 335

Gly Gly Lys Leu Ile Ser His Val Ala Ile Leu Glu Leu His Arg Ala
            340                 345                 350

Ser Gln Val Asp Ile Gln Glu Gly Lys Asp Leu Ile Leu Asp Lys Ile
            355                 360                 365

Ser Thr Trp Thr Arg Asn Phe Met Glu Gln Glu Leu Leu Asp Asn Gln
            370                 375                 380

Ile Leu Asp Arg Ser Lys Lys Glu Met Glu Phe Ala Met Arg Lys Phe
385                 390                 395                 400

Tyr Gly Thr Phe Asp Arg Val Glu Thr Arg Arg Tyr Ile Glu Ser Tyr
                405                 410                 415

Lys Met Asp Ser Phe Lys Ile Leu Lys Ala Ala Tyr Arg Ser Ser Asn
            420                 425                 430
```

Ile Asn Asn Ile Asp Leu Leu Lys Phe Ser Glu His Asp Phe Asn Leu
            435                 440                 445

Cys Gln Ala Arg His Lys Glu Glu Leu Gln Gln Ile Lys Arg Trp Phe
    450                 455                 460

Ala Asp Cys Lys Leu Glu Gln Val Gly Ser Ser Gln Asn Tyr Leu Tyr
465                 470                 475                 480

Thr Ser Tyr Phe Pro Ile Ala Ala Ile Leu Phe Glu Pro Glu Tyr Gly
                485                 490                 495

Asp Ala Arg Leu Ala Phe Ala Lys Cys Gly Ile Ile Ala Thr Thr Val
                500                 505                 510

Asp Asp Phe Phe Asp Gly Phe Ala Cys Asn Glu Leu Gln Asn Ile
                515                 520                 525

Ile Glu Leu Val Glu Arg Trp Asp Gly Tyr Pro Thr Val Gly Phe Arg
            530                 535                 540

Ser Glu Arg Val Arg Ile Phe Phe Leu Ala Leu Tyr Lys Met Ile Glu
545                 550                 555                 560

Glu Ile Ala Ala Lys Ala Glu Thr Lys Gln Gly Arg Cys Val Lys Asp
                565                 570                 575

Leu Leu Ile Asn Leu Trp Ile Asp Leu Leu Lys Cys Met Leu Val Glu
            580                 585                 590

Leu Asp Leu Trp Lys Ile Lys Ser Thr Thr Pro Ser Ile Glu Glu Tyr
        595                 600                 605

Leu Ser Ile Ala Cys Val Thr Thr Gly Val Lys Cys Leu Ile Leu Ile
        610                 615                 620

Ser Leu His Leu Leu Gly Pro Lys Leu Ser Lys Asp Val Thr Glu Ser
625                 630                 635                 640

Ser Glu Val Ser Ala Leu Trp Asn Cys Thr Ala Val Val Ala Arg Leu
                645                 650                 655

Asn Asn Asp Ile His Ser Tyr Lys Arg Glu Gln Ala Glu Ser Ser Thr
            660                 665                 670

Asn Met Ala Ala Ile Leu Ile Ser Gln Ser Gln Arg Thr Ile Ser Glu
    675                 680                 685

Glu Glu Ala Ile Arg Gln Ile Lys Glu Met Met Glu Ser Lys Arg Arg
        690                 695                 700

Glu Leu Leu Gly Met Val Leu Gln Asn Lys Glu Ser Gln Leu Pro Gln
705                 710                 715                 720

Val Cys Lys Asp Leu Phe Trp Thr Thr Phe Lys Ala Ala Tyr Ser Ile
                725                 730                 735

Tyr Thr His Gly Asp Glu Tyr Arg Phe Pro Gln Glu Leu Lys Asn His
            740                 745                 750

Ile Asn Asp Val Ile Tyr Lys Pro Leu Asn Gln Tyr Ser Pro
        755                 760                 765

<210> SEQ ID NO 24
<211> LENGTH: 2301
<212> TYPE: DNA
<213> ORGANISM: Artificial Sequence
<220> FEATURE:
<223> OTHER INFORMATION: Optimized cDNA for E. coli expression encoding
      for NgSCS-del29

<400> SEQUENCE: 24
atggctaatt ccatcgccc atcccgtgtt cgttgttccc actctaccgc aagctccctg      60
gaagaggcaa aagagcgcat ccgtgaaacc ttcggcaaaa atgaactctc tccttctagc    120

```
tatgatacgg cctgggttgc tatggtcccg agccgctaca gcatgaacca gccgtgcttt      180
ccgcgctgcc tggactggat tctggagaac caacgtgagg atggcagctg gggtctgaac      240
ccgagccatc cgttactggt gaaagacagc ttgagcagca cgctggcgtg tttgctggcg      300
ctgcgtaagt ggcgtattgg cgacaaccaa gtccagcgtg gcctgggttt tatcgagact      360
catggttggg cagtggacaa cgtagaccag atctctccac tgggttttga catcattttc      420
ccgagcatga ttaaatatgc ggaaaagctg aatctggatt tgccttttga tccgaacctg      480
gtgaacatga tgctgcgcga gcgcgagctg acgatcgagc gtgcgctgaa aaacgaattt      540
gagggtaata tggctaatgt cgagtacttc gccgagggtt tgggtgagct gtgtcactgg      600
aaagaaatca tgctgcacca acgccgtaac ggtagcctgt tcgactctcc ggcaacgacc      660
gccgcggctc ttatttatca tcagcacgat gagaagtgct tcggctatct gtctagcatc      720
ctgaaattac acgagaactg ggtgccgacc atctatccga ccaaggttca ctccaatctg      780
tttttcgtcg atgcgctgca gaacctgggt gttgaccgtt acttcaaaac cgaactgaag      840
tccgtcctgg atgagatcta ccgtttgtgg ctggagaaaa acgaagagat cttcagcgat      900
attgcgcact gcgcaatggc gtttcgcctg ttgcgcatga ataattacga ggttagcagc      960
gaagaactgg aaggcttcgt ggaccaagaa cattttttca ccacgtcggg tggcaagctg     1020
atcagccacg ttgccatcct ggaactgcac cgtgcaagcc aagtggacat tcaggagggc     1080
aaagacctga tcctggacaa aattagcacc tggactcgca actttatgga acaggaactg     1140
ctggataacc agatcttgga tcgtagcaaa aaagaaatgg aatttgcaat gcgtaagttt     1200
tacggtacgt tcgatcgcgt ggaaacccgt cgttatattg aaagctacaa aatggattcc     1260
ttcaagatcc tgaaggcagc gtaccgtagc tccaacatta acaatattga cctgttgaag     1320
ttcagcgagc acgacttcaa tctctgccag gcgcgtcaca aggaagaact gcagcaaatc     1380
aaacgctggt tcgcagattg caaactggag caagtcggta gcagccagaa ctacttgtac     1440
acctcttact tcccgatcgc ggccattttg ttcgagccgg agtatggcga cgcacgcctg     1500
gcgttcgcga agtgcggtat tatcgcgacc accgttgacg atttttttga cggttttgca     1560
tgtaatgaag aactgcaaaa catcatcgaa ctggtcgaga gatgggacgg ttatccgacg     1620
gttggttttcc gctccgagcg tgtgcgcatt ttctttctgg cgctgtacaa aatgattgaa     1680
gaaattgccg cgaaagcgga aacgaaacag ggccgttgcg tgaaagatct gttgatcaat     1740
ctgtggattg atctgctgaa atgcatgctg gtcgaactgg atctgtggaa aattaagagc     1800
acgaccccga gcattgaaga gtatctgagc attgcctgtg tgacgaccgg cgttaagtgc     1860
ttgatcctga ttagcctgca tctgctgggc ccgaaactga gcaaagacgt gaccgaatcc     1920
agcgaagtta gcgctctgtg gaactgtacg gccgtggttg cgcgcctgaa caacgacatt     1980
catagctaca agcgtgagca agccgagagc agcactaata tggccgcaat cctgatttcg     2040
caaagccagc gtaccatctc agaagaagaa gctatccgcc agatcaaaga gatgatggaa     2100
tcgaaacgcc gtgagctgct gggcatggtg ctgcagaata aagagagcca attgccgcaa     2160
gtctgcaaag acctgttttg gaccaccttc aaagccgcgt acagcattta cccacggt       2220
gatgagtacc gttttccaca agaactgaag aaccatatca cgatgtcat ctataagccg       2280
ttaaatcaat acagcccctta a                                                2301
```

<210> SEQ ID NO 25
<211> LENGTH: 755
<212> TYPE: PRT
<213> ORGANISM: Nicotiana glutinosa

<400> SEQUENCE: 25

Met Ser His Ser Thr Ala Ser Ser Leu Glu Glu Ala Lys Glu Arg Ile
1               5                   10                  15

Arg Glu Thr Phe Gly Lys Asn Glu Leu Ser Ser Ser Tyr Asp Thr
            20                  25                  30

Ala Trp Val Ala Met Val Pro Ser Arg Tyr Ser Met Asn Gln Pro Cys
            35                  40                  45

Phe Pro Arg Cys Leu Asp Trp Ile Leu Glu Asn Gln Arg Glu Asp Gly
        50                  55                  60

Ser Trp Gly Leu Asn Pro Ser Leu Pro Leu Leu Val Lys Asp Ser Leu
65                  70                  75                  80

Ser Ser Thr Leu Ala Cys Leu Leu Ala Leu Arg Lys Trp Arg Ile Gly
                85                  90                  95

Asp Asn Gln Val Gln Arg Gly Leu Gly Phe Ile Glu Thr His Gly Trp
                100                 105                 110

Ala Val Asp Asn Val Asp Gln Ile Ser Pro Leu Gly Phe Asp Ile Ile
            115                 120                 125

Phe Pro Ser Met Ile Lys Tyr Ala Glu Lys Leu Asn Leu Asp Leu Pro
        130                 135                 140

Phe Asp Pro Asn Leu Val Asn Met Met Leu Arg Glu Arg Glu Leu Thr
145                 150                 155                 160

Ile Glu Arg Ala Leu Lys Asn Glu Phe Glu Gly Asn Met Ala Asn Val
                165                 170                 175

Glu Tyr Phe Ala Glu Gly Leu Gly Glu Leu Cys His Trp Lys Glu Ile
            180                 185                 190

Met Leu His Gln Arg Arg Asn Gly Ser Pro Phe Asp Ser Pro Ala Thr
        195                 200                 205

Thr Ala Ala Leu Ile Tyr His Gln His Asp Glu Lys Cys Phe Gly
210                 215                 220

Tyr Leu Ser Ser Ile Leu Lys Leu His Glu Asn Trp Val Pro Thr Ile
225                 230                 235                 240

Tyr Pro Thr Lys Val His Ser Asn Leu Phe Phe Val Asp Ala Leu Gln
            245                 250                 255

Asn Leu Gly Val Asp Arg Tyr Phe Lys Thr Glu Leu Lys Ser Val Leu
            260                 265                 270

Asp Glu Ile Tyr Arg Leu Trp Leu Glu Lys Asn Glu Glu Ile Phe Ser
        275                 280                 285

Asp Ile Ala His Cys Ala Met Ala Phe Arg Leu Leu Arg Met Asn Asn
        290                 295                 300

Tyr Glu Val Ser Ser Glu Glu Leu Glu Gly Phe Val Asp Gln Glu His
305                 310                 315                 320

Phe Phe Thr Thr Ser Gly Gly Lys Leu Ile Ser His Val Ala Ile Leu
            325                 330                 335

Glu Leu His Arg Ala Ser Gln Val Asp Ile Glu Gly Lys Asp Leu
        340                 345                 350

Ile Leu Asp Lys Ile Ser Thr Trp Thr Arg Asn Phe Met Glu Gln Glu
        355                 360                 365

Leu Leu Asp Asn Gln Ile Leu Asp Arg Ser Lys Glu Met Glu Phe
        370                 375                 380

Ala Met Arg Lys Phe Tyr Gly Thr Phe Asp Arg Val Glu Thr Arg Arg
385                 390                 395                 400

Tyr Ile Glu Ser Tyr Lys Met Asp Ser Phe Lys Ile Leu Lys Ala Ala

```
                        405                 410                 415
Tyr Arg Ser Ser Asn Ile Asn Asn Ile Asp Leu Leu Lys Phe Ser Glu
            420                 425                 430

His Asp Phe Asn Leu Cys Gln Ala Arg His Lys Glu Glu Leu Gln Gln
            435                 440                 445

Ile Lys Arg Trp Phe Ala Asp Cys Lys Leu Glu Gln Val Gly Ser Ser
            450                 455                 460

Gln Asn Tyr Leu Tyr Thr Ser Tyr Phe Pro Ile Ala Ala Ile Leu Phe
465                 470                 475                 480

Glu Pro Glu Tyr Gly Asp Ala Arg Leu Ala Phe Ala Lys Cys Gly Ile
            485                 490                 495

Ile Ala Thr Thr Val Asp Asp Phe Phe Asp Gly Phe Ala Cys Asn Glu
            500                 505                 510

Glu Leu Gln Asn Ile Ile Glu Leu Val Glu Arg Trp Asp Gly Tyr Pro
            515                 520                 525

Thr Val Gly Phe Arg Ser Glu Arg Val Arg Ile Phe Phe Leu Ala Leu
            530                 535                 540

Tyr Lys Met Ile Glu Glu Ile Ala Ala Lys Ala Glu Thr Lys Gln Gly
545                 550                 555                 560

Arg Cys Val Lys Asp Leu Leu Ile Asn Leu Trp Ile Asp Leu Leu Lys
                565                 570                 575

Cys Met Leu Val Glu Leu Asp Leu Trp Lys Ile Lys Ser Thr Thr Pro
            580                 585                 590

Ser Ile Glu Glu Tyr Leu Ser Ile Ala Cys Val Thr Thr Gly Val Lys
            595                 600                 605

Cys Leu Ile Leu Ile Ser Leu His Leu Leu Gly Pro Lys Leu Ser Lys
610                 615                 620

Asp Val Thr Glu Ser Ser Glu Val Ser Ala Leu Trp Asn Cys Thr Ala
625                 630                 635                 640

Val Val Ala Arg Leu Asn Asn Asp Ile His Ser Tyr Lys Arg Glu Gln
                645                 650                 655

Ala Glu Ser Ser Thr Asn Met Val Ala Ile Leu Ile Ser Gln Ser Gln
            660                 665                 670

Arg Thr Ile Ser Glu Glu Ala Ile Arg Gln Ile Lys Glu Met Met
            675                 680                 685

Glu Ser Lys Arg Arg Glu Leu Leu Gly Met Val Leu Gln Asn Lys Glu
            690                 695                 700

Ser Gln Leu Pro Gln Val Cys Lys Asp Leu Phe Trp Thr Thr Phe Lys
705                 710                 715                 720

Ala Ala Tyr Ser Ile Tyr Thr His Gly Asp Glu Tyr Arg Phe Pro Gln
                725                 730                 735

Glu Leu Lys Asn His Ile Asn Asp Val Ile Tyr Lys Pro Leu Asn Gln
            740                 745                 750

Tyr Ser Pro
        755

<210> SEQ ID NO 26
<211> LENGTH: 2211
<212> TYPE: DNA
<213> ORGANISM: Artificial Sequence
<220> FEATURE:
<223> OTHER INFORMATION: Optimized cDNA for Saccharomyces cerevisiae
      expression encoding for SmCPS2

<400> SEQUENCE: 26
```

| | |
|---|---|
| atggctactg ttgacgctcc acaagttcac gaccacgacg gtactactgt tcaccaaggt | 60 |
| cacgacgctg ttaagaacat cgaagaccca atcgaataca tcagaacttt gttgagaact | 120 |
| actggtgacg gtagaatctc tgtttctcca tacgacactg cttgggttgc tatgatcaag | 180 |
| gacgttgaag gtagagacgg tccacaattc ccatcttctt tggaatggat cgttcaaaac | 240 |
| caattggaag acggttcttg gggtgaccaa aagttgttct gtgtttacga cagattggtt | 300 |
| aacactatcg cttgtgttgt tgctttgaga tcttggaacg ttcacgctca caaggttaag | 360 |
| agaggtgtta cttacatcaa ggaaaacgtt gacaagttga tggaaggtaa cgaagaacac | 420 |
| atgacttgtg gtttcgaagt tgttttccca gctttgttgc aaaaggctaa gtctttgggt | 480 |
| atcgaagact tgccatacga ctctccagct gttcaagaag tttaccacgt tagagaacaa | 540 |
| aagttgaaga gaatcccatt ggaaatcatg cacaagatcc caacttcttt gttgttctct | 600 |
| ttggaaggtt tggaaaactt ggactgggac aagttgttga agttgcaatc tgctgacggt | 660 |
| tctttcttga cttctccatc ttctactgct ttcgctttca tgcaaactaa ggacgaaaag | 720 |
| tgttaccaat tcatcaagaa cactatcgac actttcaacg tggtgctcc acacacttac | 780 |
| ccagttgacg ttttcggtag attgtgggct atcgacagat tgcaaagatt gggtatctct | 840 |
| agattcttcg aaccagaaat cgctgactgt ttgtctcaca tccacaagtt ctggactgac | 900 |
| aagggtgttt tctctggtag agaatctgaa ttctgtgaca tcgacgacac ttctatgggt | 960 |
| atgagattga tgagaatgca cggttacgac gttgacccaa cgttttgag aaacttcaag | 1020 |
| caaaaggacg gtaagttctc ttgttacggt ggtcaaatga tcgaatctcc atctccaatc | 1080 |
| tacaacttgt acagagcttc tcaattgaga ttcccaggtg aagaaatctt ggaagacgct | 1140 |
| aagagattcg cttacgactt cttgaaggaa aagttggcta acaaccaaat cttggacaag | 1200 |
| tgggttatct ctaagcactt gccagacgaa atcaagttgg gtttggaaat gccatggttg | 1260 |
| gctactttgc caagagttga agctaagtac tacatccaat actacgctgg ttctggtgac | 1320 |
| gtttggatcg gtaagacttt gtacagaatg ccagaaatct ctaacgacac ttaccacgac | 1380 |
| ttggctaaga ctgacttcaa gagatgtcaa gctaagcacc aattcgaatg gttgtacatg | 1440 |
| caagaatggt acgaatcttg tggtatcgaa gaattcggta tctctagaaa ggacttgttg | 1500 |
| ttgtcttact tcttggctac tgcttctatc ttcgaattgg aaagaactaa cgaaagaatc | 1560 |
| gcttgggcta agtctcaaat catcgctaag atgatcactt ctttcttcaa caaggaaact | 1620 |
| acttctgaag aagacaagag agctttgttg aacgaattgg gtaacatcaa cggtttgaac | 1680 |
| gacactaacg gtgctggtag agaaggtggt gctggttcta tcgctttggc tactttgact | 1740 |
| caattcttgg aaggtttcga cagatacact agacaccaat gaagaacgc ttggtctgtt | 1800 |
| tggttgactc aattgcaaca cggtgaagct gacgacgctg aattgttgac taacactttg | 1860 |
| aacatctgtg ctggtcacat cgctttcaga gaagaaatct tggctcacaa cgaatacaag | 1920 |
| gctttgtcta acttgacttc taagatctgt agacaattgt ctttcatcca atctgaaaag | 1980 |
| gaaatgggtg ttgaaggtga atcgctgct aagtcttcta tcaagaacaa ggaattggaa | 2040 |
| gaagacatgc aaatgttggt taagttggtt ttggaaaagt acggtggtat cgacagaaac | 2100 |
| atcaagaagg cttcttggc tgttgctaag acttactact acagagctta ccacgctgct | 2160 |
| gacactatcg acactcacat gttcaaggtt ttgttcgaac cagttgctta a | 2211 |

<210> SEQ ID NO 27
<211> LENGTH: 1578
<212> TYPE: DNA
<213> ORGANISM: Artificial Sequence
<220> FEATURE:
<223> OTHER INFORMATION: Optimized cDNA for S. cerevisiae expression encoding for truncated SsScS from Salvia sclarea

<400> SEQUENCE: 27

| | | | | | |
|---|---|---|---|---|---|
| atggctaaga | tgaaggaaaa | cttcaagaga | gaagacgaca | agttcccaac | tactactact | 60 |
| ttgagatctg | aagacatccc | atctaacttg | tgtatcatcg | acactttgca | aagattgggt | 120 |
| gttgaccaat | tcttccaata | cgaaatcaac | actatcttgg | acaacacttt | cagattgtgg | 180 |
| caagaaaagc | acaaggttat | ctacggtaac | gttactactc | acgctatggc | tttcagattg | 240 |
| ttgagagtta | agggttacga | agtttcttct | gaagaattgg | ctccatacgg | taaccaagaa | 300 |
| gctgtttctc | aacaaactaa | cgacttgcca | atgatcatcg | aattgtacag | agctgctaac | 360 |
| gaaagaatct | acgaagaaga | aagatctttg | gaaagatct | tggcttggac | tactatcttc | 420 |
| ttgaacaagc | aagttcaaga | caactctatc | ccagacaaga | agttgcacaa | gttggttgaa | 480 |
| ttctacttga | aaactacaa | gggtatcact | atcagattgg | gtgctagaag | aaacttggaa | 540 |
| ttgtacgaca | tgacttacta | ccaagctttg | aagtctacta | cagattctc | taacttgtgt | 600 |
| aacgaagact | tcttggtttt | cgctaagcaa | gacttcgaca | tccacgaagc | tcaaaaccaa | 660 |
| aagggtttgc | aacaattgca | aagatggtac | gctgactgta | gattggacac | tttgaacttc | 720 |
| ggtagagacg | ttgttatcat | cgctaactac | ttggcttctt | tgatcatcgg | tgaccacgct | 780 |
| ttcgactacg | ttagattggc | tttcgctaag | acttctgttt | tggttactat | catggacgac | 840 |
| ttcttcgact | gtcacggttc | ttctcaagaa | tgtgacaaga | tcatcgaatt | ggttaaggaa | 900 |
| tggaaggaaa | acccagacgc | tgaataccggt | tctgaagaat | tggaaatctt | gttcatggct | 960 |
| ttgtacaaca | ctgttaacga | attggctgaa | agagctagag | ttgaacaagg | tagatctgtt | 1020 |
| aaggaattct | tggttaagtt | gtgggttgaa | atcttgtctg | ctttcaagat | cgaattggac | 1080 |
| acttggtcta | acggtactca | acaatctttc | gacgaataca | tctcttcttc | ttggttgtct | 1140 |
| aacggttcta | gattgactgg | tttgttgact | atgcaattcg | ttggtgttaa | gttgtctgac | 1200 |
| gaaatgttga | tgtctgaaga | atgtactgac | ttggctagac | acgtttgtat | ggttggtaga | 1260 |
| ttgttgaacg | acgtttgttc | ttctgaaaga | gaaagagaag | aaaacatcgc | tggtaagtct | 1320 |
| tactctatct | tgttggctac | tgaaaaggac | ggtagaaagg | tttctgaaga | cgaagctatc | 1380 |
| gctgaaatca | acgaaatggt | tgaataccac | tggagaaagg | ttttgcaaat | cgtttacaag | 1440 |
| aaggaatcta | tcttgccaag | aagatgtaag | gacgtttct | tggaaatggc | taagggtact | 1500 |
| ttctacgctt | acggtatcaa | cgacgaattg | acttctccac | aacaatctaa | ggaagacatg | 1560 |
| aagtctttcg | ttttctaa | | | | | 1578 |

<210> SEQ ID NO 28
<211> LENGTH: 924
<212> TYPE: DNA
<213> ORGANISM: Artificial Sequence
<220> FEATURE:
<223> OTHER INFORMATION: Optimized cDNA for S. cerevisiae expression encoding for the GGPP synthase from Pantoea agglomerans

<400> SEQUENCE: 28

| | | | | | |
|---|---|---|---|---|---|
| atggtttctg | gttctaaggc | tggtgtttct | ccacacagag | aaatcgaagt | tatgagacaa | 60 |
| tctatcgacg | accacttggc | tggtttgttg | ccagaaactg | actctcaaga | catcgtttct | 120 |
| ttggctatga | gagaaggtgt | tatggctcca | ggtaagagaa | tcagaccatt | gttgatgttg | 180 |
| ttggctgcta | gagacttgag | ataccaaggt | tctatgccaa | cttgttggga | cttggctgt | 240 |

```
gctgttgaat tgactcacac tgcttctttg atgttggacg acatgccatg tatggacaac      300
gctgaattga aagaggtca accaactact cacaagaagt tcggtgaatc tgttgctatc      360
ttggcttctg ttggtttgtt gtctaaggct ttcggtttga tcgctgctac tggtgacttg      420
ccaggtgaaa aagagctca agctgttaac gaattgtcta ctgctgttgg tgttcaaggt      480
ttggttttgg gtcaattcag agacttgaac gacgctgctt tggacagaac tccagacgct      540
atcttgtcta ctaaccactt gaagactggt atcttgttct ctgctatgtt gcaaatcgtt      600
gctatcgctt ctgcttcttc tccatctact agagaaactt gcacgctttt cgctttggac      660
ttcggtcaag cttttccaat tgttggacga cttgagagacg accacccaga aactggtaag      720
gacagaaaca aggacgctgg taagtctact ttggttaaca gattgggtgc tgacgctgct      780
agacaaaagt tgagagaaca catcgactct gctgacaagc acttgacttt cgcttgtcca      840
caaggtggtg ctatcagaca attcatgcac ttgtggttcg gtcaccactt ggctgactgg      900
tctccagtta tgaagatcgc ttaa                                             924
```

```
<210> SEQ ID NO 29
<211> LENGTH: 2175
<212> TYPE: DNA
<213> ORGANISM: Artificial Sequence
<220> FEATURE:
<223> OTHER INFORMATION: Optimized cDNA for S. cerevisiae expression
      encoding for CfCPS1-del63

<400> SEQUENCE: 29
```

```
atggttgcta ctgttaacgc tccaccagtt cacgaccaag acgactctac tgaaaaccaa       60
tgtcacgacg ctgttaacaa catcgaagac ccaatcgaat acatcagaac tttgttgaga      120
actactggtg acgtagaat ctctgttttct ccatacgaca ctgcttgggt tgctttgatc      180
aaggacttgc aaggtagaga cgctccagaa ttcccatctt ctttggaatg gatcatccaa      240
aaccaattgg ctgacggttc ttggggtgac gctaagttct ctgtgtttta cgacagattg      300
gttaacacta tcgcttgtgt tgttgctttg agatcttggg acgttcacgc tgaaaaggtt      360
gaaagaggtg ttagatacat caacgaaaac gttgaaaagt tgagagacgg taacgaagaa      420
cacatgactt gtggtttcga agttgttttc ccagcttttgt tgcaaagagc taagtctttg      480
ggtatccaag acttgccata cgacgctcca gttatccaag aaatctacca ctctagagaa      540
caaaagtcta gagaatccc attggaaatg atgcacaagg ttccaacttc tttgttgttc      600 tcttttggaag gtttggaaaa cttggaatgg acaagttgt tgaagttgca atctgctgac      660
ggttctttct tgacttctcc atcttctact gctttcgctt tcatgcaaac tagagaccca      720
aagtgttacc aattcatcaa gaacactatc caaacttca acggtggtgc tccacacact      780
tacccagttg acgttttcgg tagattgtgg gctatcgaca gattgcaaag attgggtatc      840
tctagattct tcgaatctga aatcgctgac tgtatcgctc acatccacag attctggact      900
gaaaagggtg ttttctctgg tagagaatct gaattctgtg acatcgacga cacttctatg      960
ggtgttagat tgatgagaat gcacggttac gacgttgacc aaaacgtttt gaagaacttc     1020
aagaaggacg acaagttctc ttgttacggt ggtcaaatga tcgaatctcc atctccaatc     1080
tacaacttgt acagagcttc tcaattgaga ttcccaggtg aacaaatctt ggaagacgct     1140
aacaagttcg cttacgactt cttgcaagaa aagttggctc acaaccaaat cttggacaag     1200
tgggttatct ctaagcactt gccagacgaa atcaagttgg tttgggaaat gccatggtac     1260
gctactttgc aagagttga agctagatac tacatccaat actacgctgg ttctggtgac     1320
```

```
gtttggatcg gtaagacttt gtacagaatg ccagaaatct ctaacgacac ttaccacgaa    1380
ttggctaaga ctgacttcaa gagatgtcaa gctcaacacc aattcgaatg gatctacatg    1440
caagaatggt acgaatcttg taacatggaa gaattcggta tctctagaaa ggaattgttg    1500
gttgcttact tcttggctac tgcttctatc ttcgaattgg aaagagctaa cgaaagaatc    1560
gcttgggcta agtctcaaat catctctact atcatcgctt ctttcttcaa caaccaaaac    1620
acttctccag aagacaagtt ggctttcttg actgacttca agaacggtaa ctctactaac    1680
atggctttgg ttactttgac tcaattcttg gaaggtttcg acagatacac ttctcaccaa    1740
ttgaagaacg cttggtctgt ttggttgaga aagttgcaac aaggtgaagg taacggtggt    1800
gctgacgctg aattgttggt taacactttg aacatctgtg ctggtcacat cgctttcaga    1860
gaagaaatct tggctcacaa cgactacaag actttgtcta acttgacttc taagatctgt    1920
agacaattgt ctcaaatcca aaacgaaaag gaattggaaa ctgaaggtca aaagacttct    1980
atcaagaaca aggaattgga agaagacatg caaagattgg ttaagttggt tttggaaaag    2040
tctagagttg gtatcaacag agacatgaag aagactttct ggctgttgt taagacttac    2100 tactacaagg cttaccactc tgctcaagct atcgacaacc acatgttcaa ggttttgttc    2160
gaaccagttg cttaa                                                    2175
```

<210> SEQ ID NO 30
<211> LENGTH: 2100
<212> TYPE: DNA
<213> ORGANISM: Artificial Sequence
<220> FEATURE:
<223> OTHER INFORMATION: Optimized cDNA for S. cerevisiae expression
      encoding for TaTps1-del59

<400> SEQUENCE: 30

```
atgtacagac aaagaactga cgaaccatct gaaactagac aaatgatcga cgacatcaga     60
actgctttgg cttctttggg tgacgacgaa acttctatgt ctgtttctgc ttacgacact    120
gctttggttg cttttggttaa gaacttggac ggtggtgacg tccacaatt cccatcttgt    180 atcgactgga tcgttcaaaa ccaattgcca gacggttctt ggggtgaccc agctttcttc    240
atggttcaag acagaatgat ctctactttg gcttgtgttg ttgctgttaa gtcttggaac    300
atcgacagag acaacttgtg tgacagaggt gttttgttca tcaaggaaaa catgtctaga    360
ttggttgaag aagaacaaga ctggatgcca tgtggtttcg aaatcaactt cccagctttg    420
ttggaaaagg ctaaggactt ggacttggac atcccatacg accacccagt tttggaagaa    480
atctacgcta agagaaactt gaagttgttg aagatcccat ggacgttttt gcacgctatc    540
ccaactactt tgttgttctc tgttgaaggt atggttgact tgccattgga ctgggaaaag    600
ttgttgagat tgagatgtcc agacggttct ttccactctt ctccagctgc tactgctgct    660
gctttgtctc acactggtga caaggaatgt cacgctttct tggacagatt gatccaaaag    720
ttcgaaggtg tgttccatg ttctcactct atggacactt cgaacaatt gtgggttgtt    780 gacagattga tgagattggg tatctctaga cacttcactt ctgaaatcca acaatgtttg    840
gaattcatct acagaagatg gactcaaaag ggtttggctc acaacatgca ctgtccaatc    900
ccagacatcg acgacactgc tatgggtttc agattgttga caacacgg ttacgacgtt    960 actccatctg tttcaagca cttcgaaaag gacggtaagt tcgtttgttt cccaatggaa   1020
actaaccacg cttctgttac tccaatgcac aacacttaca gagcttctca attcatgttc   1080
ccaggtgacg acgacgtttt ggctagagct ggtagatact gtagagcttt cttgcaagaa   1140
```

-continued

| agacaatctt | ctaacaagtt | gtacgacaag | tggatcatca | ctaaggactt | gccaggtgaa | 1200 |
| gttggttaca | ctttgaactt | cccatggaag | tcttctttgc | caagaatcga | aactagaatg | 1260 |
| tacttggacc | aatacggtgg | taacaacgac | gtttggatcg | ctaaggtttt | gtacagaatg | 1320 |
| aacttggttt | ctaacgactt | gtacttgaag | atggctaagg | ctgacttcac | tgaataccaa | 1380 |
| agattgtcta | gaatcgaatg | gaacggtttg | agaaagtggt | acttcagaaa | ccacttgcaa | 1440 |
| agatacggtg | ctactccaaa | gtctgctttg | aaggcttact | tcttggcttc | tgctaacatc | 1500 |
| ttcgaaccag | gtagagctgc | tgaaagattg | gcttgggcta | gaatggctgt | tttggctgaa | 1560 |
| gctgttacta | ctcacttcag | acacatcggt | ggtccatgtt | actctactga | aaacttggaa | 1620 |
| gaattgatcg | acttggtttc | tttcgacgac | gtttctggtg | gtttgagaga | agcttggaag | 1680 |
| caatggttga | tggcttggac | tgctaaggaa | tctcacggtt | ctgttgacgg | tgacactgct | 1740 |
| ttgttgttcg | ttagaactat | cgaaatctgt | tctggtagaa | tcgtttcttc | tgaacaaaag | 1800 |
| ttgaacttgt | gggactactc | tcaattggaa | caattgactt | cttctatctg | tcacaagttg | 1860 |
| gctactatcg | gtttgtctca | aaacgaagct | tctatggaaa | acactgaaga | cttgcaccaa | 1920 |
| caagttgact | tggaaatgca | agaattgtct | tggagagttc | accaaggttg | tcacggtatc | 1980 |
| aacagagaaa | ctagacaaac | tttcttgaac | gttgttaagt | cttttctacta | ctctgctcac | 2040 |
| tgttctccag | aaactgttga | ctctcacatc | gctaaggtta | tcttccaaga | cgttatctaa | 2100 |

<210> SEQ ID NO 31
<211> LENGTH: 2172
<212> TYPE: DNA
<213> ORGANISM: Artificial Sequence
<220> FEATURE:
<223> OTHER INFORMATION: Optimized cDNA for S. cerevisiae expression encoding for MvCps3-del63

<400> SEQUENCE: 31

| atggctccac | cagaacaaaa | gtacaactct | actgctttgg | aacacgacac | tgaaatcatc | 60 |
| gaaatcgaag | accacatcga | atgtatcaga | agattgttga | gaactgctgg | tgacggtaga | 120 |
| atctctgttt | ctccatacga | cactgcttgg | atcgctttga | tcaaggactt | ggacggtcac | 180 |
| gactctccac | aattcccatc | ttctatggaa | tgggttgctg | acaaccaatt | gccagacggt | 240 |
| tcttggggtg | acgaacactt | cgtttgtgtt | tacgacagat | ggttaacac | tatcgcttgt | 300 |
| gttgttgctt | tgagatcttg | gaacgttcac | gctcacaagt | gtgaaaaggg | tatcaagtac | 360 |
| atcaaggaaa | acgttcacaa | gttggaagac | gctaacgaag | aacacatgac | ttgtggtttc | 420 |
| gaagttgttt | cccagctttt | gttgcaaaga | gctcaatcta | gggtatcaa | gggtatccca | 480 |
| tacaacgctc | cagttatcga | agaaatctac | aactctagag | aaaagaagtt | gaagagaatc | 540 |
| ccaatggaag | ttgttcacaa | ggttgctact | tctttgttgt | tctctttgga | aggtttggaa | 600 |
| aacttggaat | gggaaaagtt | gttgaagttg | caatctccag | acggttcttt | cttgacttct | 660 |
| ccatcttcta | ctgctttcgc | tttcatccac | actaaggaca | gaaagtgttt | caacttcatc | 720 |
| aacaacatcg | ttcacacttt | caagggtggt | gctccacaca | cttacccagt | tgacatcttc | 780 |
| ggtagattgt | gggctgttga | cagattgcaa | agattgggta | tctctagatt | cttcgaatct | 840 |
| gaaatcgctg | aattcttgtc | tcacgttcac | agattctggt | ctgacgaagc | tggtgttttc | 900 |
| tctggtagag | aatctgtttt | ctgtgacatc | gacgacactt | ctatgggttt | gagattgttg | 960 |
| agaatgcacg | gttaccacgt | tgacccaaac | gttttgaaga | acttcaagca | atctgacaag | 1020 |
| ttctcttgtt | acggtggtca | aatgatggaa | tgttcttctc | caatctacaa | cttgtacaga | 1080 |

| gcttctcaat tgcaattccc aggtgaagaa atcttggaag aagctaacaa gttcgcttac | 1140 |
| aagttcttgc aagaaaagtt ggaatctaac caaatcttgg acaagtggtt gatctctaac | 1200 |
| cacttgtctg acgaaatcaa ggttggtttg aaatgccat ggtacgctac tttgccaaga | 1260 |
| gttgaaactt cttactacat ccaccactac ggtggtggtg acgacgtttg gatcggtaag | 1320 |
| actttgtaca gaatgccaga atctctaac gacacttaca gagaattggc tagattggac | 1380 |
| ttcagaagat gtcaagctca acaccaattg gaatggatct acatgcaaag atggtacgaa | 1440 |
| tcttgtagaa tgcaagaatt cggtatctct agaaaggaag ttttgagagc ttacttcttg | 1500 |
| gcttctggta ctatcttcga agttgaaaga gctaaggaaa gagttgcttg ggctagatct | 1560 |
| caaatcatct ctcacatgat caagtctttc ttcaacaagg aaactacttc ttctgaccaa | 1620 |
| aagcaagctt tgttgactga attgttgttc ggtaacatct ctgcttctga aactgaaaag | 1680 |
| agagaattgg acggtgttgt tgttgctact ttgagacaat tcttggaagg tttcgacatc | 1740 |
| ggtactagac accaagttaa ggctgcttgg gacgtttggt tgagaaaggt tgaacaaggt | 1800 |
| gaagctcacg gtggtgctga cgctgaattg tgtactacta ctttgaacac ttgtgctaac | 1860 |
| caacacttgt cttctcaccc agactacaac actttgtcta agttgactaa caagatctgt | 1920 |
| cacaagttgt ctcaaatcca acaccaaaag gaaatgaagg gtggtatcaa ggctaagtgt | 1980 |
| tctatcaaca caaggaagt tgacatcgaa atgcaatggt tggttaagtt ggttttggaa | 2040 |
| aagtctggtt tgaacagaaa ggctaagcaa gctttcttgt ctatcgctaa gacttactac | 2100 |
| tacagagctt actacgctga ccaaactatg gacgctcaca tcttcaaggt tttgttcgaa | 2160 |
| ccagttgttt aa | 2172 |

<210> SEQ ID NO 32
<211> LENGTH: 2202
<212> TYPE: DNA
<213> ORGANISM: Artificial Sequence
<220> FEATURE:
<223> OTHER INFORMATION: Optimized cDNA for S. cerevisiae expression
encoding for RoCPS1-del67

<400> SEQUENCE: 32

| atggcttctc aagtttctga aaagggtact tcttctccag ttcaaactcc agaagaagtt | 60 |
| aacgaaaaga tcgaaaacta catcgaatac atcaagaact tgttgactac ttctggtgac | 120 |
| ggtagaatct ctgtttctcc atacgacact tctatcgttg ctttgatcaa ggacttgaag | 180 |
| ggtagagaca ctccacaatt cccatcttgt ttggaatgga tcgctcaaca ccaaatggct | 240 |
| gacggttctt ggggtgacga attcttctgt atctacgaca gaatcttgaa cactttggct | 300 |
| tgtgttgttg ctttgaagtc ttggaacgtt cacgctgaca tgatcgaaaa gggtgttact | 360 |
| tacgttaacg aaaacgttca aaagttggaa gacggtaact tggaacacat gacttctggt | 420 |
| ttcgaaatcg ttgttccagc tttggttcaa agagctcaag acttgggtat ccaaggtttg | 480 |
| ccatacgacc acccattgat caaggaaatc gctaacacta aggaaggtag attgaagaag | 540 |
| atcccaaagg acatgatcta ccaaaagcca actactttgt tgttctcttt ggaaggtttg | 600 |
| ggtgacttgg aatgggaaaa gatcttgaag ttgcaatctg gtgacggttc tttcttgact | 660 |
| tctccatctt ctactgctca cgttttcatg aagactaagg acgaaaagtg tttgaagttc | 720 |
| atcgaaaacg ctgttaagaa ctgtaacggt ggtgctccac acacttaccc agttgacgtt | 780 |
| ttcgctagat tgtgggctgt tgacagattg caaagattgg gtatctctag attcttccaa | 840 |
| caagaaatca agtacttctt ggaccacatc aactctgttt ggactgaaaa cggtgttttc | 900 |

```
tctggtagag actctgaatt ctgtgacatc gacgacactt ctatgggtat cagattgttg    960
aagatgcacg gttacgacat cgacccaaac gctttggaac acttcaagca acaagacggt   1020
aagttctctt gttacggtgg tcaaatgatc gaatctgctt ctccaatcta caacttgtac   1080
agagctgctc aattgagatt cccaggtgaa gaaatcttgg aagaagctac taagttcgct   1140
tacaacttct tgcaagaaaa gatcgctaac gaccaattcc aagaaaagtg ggttatctct   1200
gaccacttga tcgacgaagt taagttgggt ttgaagatgc catggtacgc tactttgcca   1260
agagttgaag ctgcttacta cttgcaatac tacgctggtt gtggtgacgt ttggatcggt   1320
aaggttttct acagaatgcc agaaatctct aacgacactt acaagaagtt ggctatcttg   1380
gacttcaaca gatgtcaagc tcaacaccaa ttcgaatgga tctacatgca agaatggtac   1440
cacagatctt ctgtttctga attcggtatc tctaagaagg acttgttgag agcttacttc   1500
ttggctgctg ctactatctt cgaaccagaa agaactcaag aaagattggt ttgggctaag   1560
actcaaatcg tttctggtat gatcacttct ttcgttaact ctggtactac tttgtctttg   1620
caccaaaaga ctgctttgtt gtctcaaatc ggtcacaact tcgacggttt ggacgaaatc   1680
atctctgcta tgaaggacca cggtttggct gctactttgt tgactacttt ccaacaattg   1740
ttggacggtt cgacagata cactagacac caattgaaga acgcttggtc tcaatggttc   1800
atgaagttgc aacaaggtga agcttctggt ggtgaagacg ctgaattgtt ggctaacact   1860
ttgaacatct gtgctggttt gatcgctttc aacgaagacg ttttgtctca ccacgaatac   1920
actactttgt ctactttgac taacaagatc tgtaagagat tgactcaaat ccaagacaag   1980
aagactttgg aagttgttga cggttctatc aaggacaagg aattggaaaa ggacatccaa   2040
atgttggtta agttggtttt ggaagaaaac ggtggtggtg ttgacagaaa catcaagcac   2100
actttcttgt ctgttttcaa gactttctac tacaacgctt accacgacga cgaaactact   2160
gacgttcaca tcttcaaggt tttgttcggt ccagttgttt aa                      2202
```

<210> SEQ ID NO 33
<211> LENGTH: 2301
<212> TYPE: DNA
<213> ORGANISM: Artificial Sequence
<220> FEATURE:
<223> OTHER INFORMATION: Optimized cDNA for S. cerevisiae expression encoding for NgSCS-del29

<400> SEQUENCE: 33

```
atggctaact tccacagacc atctagagtt agatgttctc actctactgc ttcttctttg    60
gaagaagcta aggaaagaat cagagaaact ttcggtaaga cgaattgtc tccatcttct   120 tacgacactg cttgggttgc tatggttcca tctagatact ctatgaacca accatgtttc   180
ccaagatgtt tggactggat cttggaaaac caaagagaag acggttcttg ggggtttgaac   240 ccatctcacc cattgttggt taaggactct ttgtcttcta ctttggcttg tttgttggct   300
ttgagaaagt ggagaatcgg tgacaaccaa gttcaaagag gtttgggttt catcgaaact   360
cacggttggg ctgttgacaa cgttgaccaa atctctccat gggtttcga catcatcttc   420 ccatctatga tcaagtacgc tgaaaagttg aacttggact tgccattcga cccaaacttg   480
gttaacatga tgttgagaga agagaattg actatcgaaa gagctttgaa gaacgaattc   540
gaaggtaaca tggctaacgt tgaatacttc gctgaaggtt gggtgaatt gtgtcactgg   600 aaggaaatca tgttgcacca agaagaaac ggttctttgt tcgactctcc agctactact   660
gctgctgctt tgatctacca ccaacacgac gaaaagtgtt tcggttactt gtcttctatc   720
```

```
ttgaagttgc acgaaaactg ggttccaact atctacccaa ctaaggttca ctctaacttg      780
ttcttcgttg acgctttgca aaacttgggt gttgacagat acttcaagac tgaattgaag      840
tctgttttgg acgaaatcta cagattgtgg ttggaaaaga acgaagaaat cttctctgac      900
atcgctcact gtgctatggc tttcagattg ttgagaatga caactacga agtttcttct       960 gaagaattgg aaggtttcgt tgaccaagaa cacttcttca ctacttctgg tggtaagttg     1020
atctctcacg ttgctatctt ggaattgcac agagcttctc aagttgacat ccaagaaggt     1080
aaggacttga tcttggacaa gatctctact tggactagaa acttcatgga caagaattg      1140 ttggacaacc aaatcttgga cagatctaag aaggaaatgg aattcgctat gagaaagttc     1200
tacggtactt cgacagagt tgaaactaga agatacatcg aatcttacaa gatggactct      1260
ttcaagatct tgaaggctgc ttacagatct tctaacatca acaacatcga cttgttgaag     1320
ttctctgaac acgacttcaa cttgtgtcaa gctagacaca aggaagaatt gcaacaaatc     1380
aagagatggt tcgctgactg taagttgaa caagttggtt cttctcaaaa ctacttgtac      1440
acttcttact tcccaatcgc tgctatcttg ttcgaaccag aatacggtga cgctagattg     1500
gctttcgcta agtgtggtat catcgctact actgttgacg acttcttcga cggtttcgct     1560
tgtaacgaag aattgcaaaa catcatcgaa ttggttgaaa gatgggacgg ttacccaact     1620
gttggtttca gatctgaaag agttagaatc ttcttcttgg cttttgtacaa gatgatcgaa    1680 gaaatcgctg ctaaggctga aactaagcaa ggtagatgtg ttaaggactt gttgatcaac     1740
ttgtggatcg acttgttgaa gtgtatgttg gttgaattgg acttgtggaa gatcaagtct     1800
actactccat ctatcgaaga atacttgtct atcgcttgtg ttactactgg tgttaagtgt     1860
ttgatcttga tctctttgca cttgttgggt ccaaagttgt ctaaggacgt tactgaatct     1920
tctgaagttt ctgctttgtg gaactgtact gctgttgttg ctagattgaa caacgacatc     1980
cactcttaca agagagaaca agctgaatct tctactaaca tggctgctat cttgatctct     2040
caatctcaaa gaactatctc tgaagaagaa gctatcagac aaatcaagga atgatggaa     2100 tctaagagaa gagaattgtt gggtatggtt ttgcaaaaca aggaatctca attgccacaa     2160
gtttgtaagg acttgttctg gactactttc aaggctgctt actctatcta cactcacggt     2220
gacgaataca gattcccaca agaattgaag aaccacatca cgacgttat ctacaagcca      2280 ttgaaccaat actctccata a                                                2301
```

<210> SEQ ID NO 34
<211> LENGTH: 2268
<212> TYPE: DNA
<213> ORGANISM: Artificial Sequence
<220> FEATURE:
<223> OTHER INFORMATION: Optimized cDNA for S. cerevisiae expression
      encoding for NgSCS-del38

<400> SEQUENCE: 34

```
atgtctcact ctactgcttc ttctttggaa gaagctaagg aaagaatcag agaaactttc       60
ggtaagaacg aattgtcttc ttcttcttac gacactgctt gggttgctat ggttccatct      120
agatactcta tgaaccaacc atgtttccca gatgtttggg actggatctt ggaaaaccaa      180
agagaagacg ttcttgggg tttgaaccca tctttgccat tgttggttaa ggactctttg       240
tcttctactt tggcttgttt gttggctttg agaaagtgga gaatcggtga acaaccaagtt    300 caaagaggtt tgggttcat cgaaactcac ggttgggctg ttgacaacgt tgaccaaatc       360
tctccattgg gtttcgacat catcttccca tctatgatca agtacgctga aaagttgaac      420
```

| | |
|---|---|
| ttggacttgc cattcgaccc aaacttggtt aacatgatgt tgagagaaag agaattgact | 480 |
| atcgaaagag ctttgaagaa cgaattcgaa ggtaacatgg ctaacgttga atacttcgct | 540 |
| gaaggtttgg gtgaattgtg tcactggaag gaaatcatgt tgcaccaaag aagaaacggt | 600 |
| tctccattcg actctccagc tactactgct gctgctttga tctaccacca acacgacgaa | 660 |
| aagtgtttcg gttacttgtc ttctatcttg aagttgcacg aaaactgggt tccaactatc | 720 |
| tacccaacta aggttcactc taacttgttc ttcgttgacg cttttgcaaaa cttgggtgtt | 780 |
| gacagatact tcaagactga attgaagtct gttttggacg aaatctacag attgtggttg | 840 |
| gaaaagaacg aagaaatctt ctctgacatc gctcactgtg ctatggcttt cagattgttg | 900 |
| agaatgaaca actacgaagt ttcttctgaa gaattggaag gtttcgttga ccaagaacac | 960 |
| ttcttcacta cttctggtgg taagttgatc tctcacgttg ctatcttgga attgcacaga | 1020 |
| gcttctcaag ttgacatcca agaaggtaag gacttgatct tggacaagat ctctacttgg | 1080 |
| actagaaact tcatggaaca agaattgttg gacaaccaaa tcttggacag atctaagaag | 1140 |
| gaaatggaat tcgctatgag aaagttctac ggtactttcg acagagttga aactagaaga | 1200 |
| tacatcgaat cttacaagat ggactctttc aagatcttga aggctgctta cagatcttct | 1260 |
| aacatcaaca acatcgactt gttgaagttc tctgaacacg acttcaactt gtgtcaagct | 1320 |
| agacacaagg aagaattgca acaaatcaag agatggttcg ctgactgtaa gttggaacaa | 1380 |
| gttggttctt ctcaaaacta cttgtacact tcttacttcc caatcgctgc tatcttgttc | 1440 |
| gaaccagaat acggtgacgc tagattggct ttcgctaagt gtggtatcat cgctactact | 1500 |
| gttgacgact tcttcgacgg tttcgcttgt aacgaagaat tgcaaaacat catcgaattg | 1560 |
| gttgaaagat gggacggtta cccaactgtt ggtttcagat ctgaaagagt tagaatcttc | 1620 |
| ttcttggctt tgtacaagat gatcgaagaa atcgctgcta aggctgaaac taagcaaggt | 1680 |
| agatgtgtta aggacttgtt gatcaacttg tggatcgact tgttgaagtg tatgttggtt | 1740 |
| gaattggact tgtggaagat caagtctact actccatcta tcgaagaata cttgtctatc | 1800 |
| gcttgtgtta ctactggtgt taagtgtttg atcttgatct cttttgcactt gttgggtcca | 1860 |
| aagttgtcta aggacgttac tgaatcttct gaagtttctg cttttgtggaa ctgtactgct | 1920 |
| gttgttgcta gattgaacaa cgacatccac tcttacaaga gagaacaagc tgaatcttct | 1980 |
| actaacatgg ttgctatctt gatctctcaa tctcaaagaa ctatctctga agaagaagct | 2040 |
| atcagacaaa tcaaggaaat gatggaatct aagagaagag aattgttggg tatggttttg | 2100 |
| caaaacaagg aatctcaatt gccacaagtt tgtaaggact tgttctggac tactttcaag | 2160 |
| gctgcttact ctatctacac tcacggtgac gaatacagat tcccacaaga attgaagaac | 2220 |
| cacatcaacg acgttatcta caagccattg aaccaatact ctccataa | 2268 |

<210> SEQ ID NO 35
<211> LENGTH: 85
<212> TYPE: DNA
<213> ORGANISM: Artificial Sequence
<220> FEATURE:
<223> OTHER INFORMATION: Primer Sequence

<400> SEQUENCE: 35

| | |
|---|---|
| aggtgcagtt cgcgtgcaat tataacgtcg tggcaactgt tatcagtcgt accgcgccat | 60 |
| tgagagtgca ccataccaca gcttt | 85 |

<210> SEQ ID NO 36
<211> LENGTH: 85

```
<212> TYPE: DNA
<213> ORGANISM: Artificial Sequence
<220> FEATURE:
<223> OTHER INFORMATION: Primer Sequence

<400> SEQUENCE: 36
tcgtggtcaa ggcgtgcaat tctcaacacg agagtgattc ttcggcgttg ttgctgacca    60
gcggtatttc acaccgcata gggta                                          85

<210> SEQ ID NO 37
<211> LENGTH: 85
<212> TYPE: DNA
<213> ORGANISM: Artificial Sequence
<220> FEATURE:
<223> OTHER INFORMATION: Primer Sequence

<400> SEQUENCE: 37
tggtcagcaa caacgccgaa gaatcactct cgtgttgaga attgcacgcc ttgaccacga    60
cacgttaagg gattttggtc atgag                                          85

<210> SEQ ID NO 38
<211> LENGTH: 80
<212> TYPE: DNA
<213> ORGANISM: Artificial Sequence
<220> FEATURE:
<223> OTHER INFORMATION: Primer Sequence

<400> SEQUENCE: 38
aacgcgtacc ctaagtacgg caccacagtg actatgcagt ccgcactttg ccaatgccaa    60
aaatgtgcgc ggaaccccta                                                80

<210> SEQ ID NO 39
<211> LENGTH: 84
<212> TYPE: DNA
<213> ORGANISM: Artificial Sequence
<220> FEATURE:
<223> OTHER INFORMATION: Primer Sequence

<400> SEQUENCE: 39
ttggcattgg caaagtgcgg actgcatagt cactgtggtg ccgtacttag ggtacgcgtt    60
cctgaacgaa gcatctgtgc ttca                                           84

<210> SEQ ID NO 40
<211> LENGTH: 85
<212> TYPE: DNA
<213> ORGANISM: Artificial Sequence
<220> FEATURE:
<223> OTHER INFORMATION: Primer Sequence

<400> SEQUENCE: 40
ccgagatgcc aaaggatagg tgctatgttg atgactacga cacagaactg cgggtgacat    60
aatgatagca ttgaaggatg agact                                          85

<210> SEQ ID NO 41
<211> LENGTH: 82
<212> TYPE: DNA
<213> ORGANISM: Artificial Sequence
<220> FEATURE:
<223> OTHER INFORMATION: Primer Sequence

<400> SEQUENCE: 41
atgtcacccg cagttctgtg tcgtagtcat caacatagca cctatccttt ggcatctcgg    60
```

```
<210> SEQ ID NO 42
<211> LENGTH: 81
<212> TYPE: DNA
<213> ORGANISM: Artificial Sequence
<220> FEATURE:
<223> OTHER INFORMATION: Primer Sequence

<400> SEQUENCE: 42
ctcagatgta cggtgatcgc caccatgtga cggaagctat cctgacagtg tagcaagtgc    60
tgagcgtcag accccgtaga a                                              81

<210> SEQ ID NO 43
<211> LENGTH: 60
<212> TYPE: DNA
<213> ORGANISM: Artificial Sequence
<220> FEATURE:
<223> OTHER INFORMATION: Primer Sequence

<400> SEQUENCE: 43
attcctagtg acggccttgg gaactcgata cacgatgttc agtagaccgc tcacacatgg    60

<210> SEQ ID NO 44
<211> LENGTH: 79
<212> TYPE: DNA
<213> ORGANISM: Artificial Sequence
<220> FEATURE:
<223> OTHER INFORMATION: Primer Sequence

<400> SEQUENCE: 44
aggtgcagtt cgcgtgcaat tataacgtcg tggcaactgt tatcagtcgt accgcgccat    60
tcgactacgt cgtaaggcc                                                 79

<210> SEQ ID NO 45
<211> LENGTH: 80
<212> TYPE: DNA
<213> ORGANISM: Artificial Sequence
<220> FEATURE:
<223> OTHER INFORMATION: Primer Sequence

<400> SEQUENCE: 45
tcgtggtcaa ggcgtgcaat tctcaacacg agagtgattc ttcggcgttg ttgctgacca    60
tcgacggtcg aggagaactt                                                80
```

PRODUCTION OF MANOOL

CROSS-REFERENCE TO RELATED APPLICATIONS

This application is a U.S. National Phase Application of PCT/EP2017/083372, filed Dec. 18, 2017, which claims the benefit of priority to European Patent Application No. 16206349.9, filed Dec. 22, 2016, the entire contents of which are hereby incorporated by reference herein.

TECHNICAL FIELD

Provided herein are biochemical methods of producing (+)-manool using a copalyl diphosphate synthase and a sclareol synthase.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. These enzymes convert an acyclic terpene precursor in one or more terpene products. In particular, diterpene synthases produce diterpenes by cyclization of the precursor geranylgeranyl diphosphate (GGPP). The cyclization of GGPP often requires two enzyme polypeptides, a type I and a type II diterpene synthase working in combination in two successive enzymatic reactions. The type II diterpene synthases catalyze a cyclization/rearrangement of GGPP initiated by the protonation of the terminal double bond of GGPP leading to a cyclic diterpene diphosphate intermediate. This intermediate is then further converted by a type I diterpene synthase catalyzing an ionization initiated cyclization.

Diterpene synthases are present in the plants and other organisms and use substrates such as GGPP but they have different product profiles. Genes and cDNAs encoding diterpene synthases have been cloned and the corresponding recombinant enzymes characterized.

Copalyl diphosphate (CPP) synthase enzymes and sclareol synthase enzymes are enzymes that occur in plants. Hence, it is desirable to discover and use these enzymes and variants in biochemical processes to generate (+)-manool.

SUMMARY

Provided herein is a method of producing (+)-manool comprising:
a) contacting geranylgeranyl diphosphate (GGPP) with a copalyl diphosphate (CPP) synthase to form a copalyl diphosphate, wherein the CPP synthase comprises
  i) an amino acid sequence having at least 50%, 55%, 60%, 65%, 70%, 75%, 80%, 85%, 90%, 95%, 98%, 99% or 100% sequence identity to a polypeptide selected from group consisting of SEQ ID NO: 14 and SEQ ID NO: 15; or
  ii) an amino acid sequence having at least 71%, 72%, 75%, 80%, 85%, 90%, 95%, 98%, 99% or 100% sequence identity to a polypeptide selected from group consisting of SEQ ID NO: 17 and SEQ ID NO: 18; or
  iii) an amino acid sequence having at least 90%, 91%, 92%, 93%, 94%, 95%, 96%, 97%, 98%, 99% or 100% sequence identity to a polypeptide selected from group consisting of SEQ ID NO: 20 and SEQ ID NO: 21; and
b) contacting the CPP with a sclareol synthase to form (+)-manool; and
c) optionally isolating the (+)-manool.

Provided herein is the above method further comprising further processing the (+)-manool to a (+)-manool derivative.

Also provided herein is a polypeptide having CPP synthase activity, wherein the polypeptide comprises
a) an amino acid sequence having at least 50%, 55%, 60%, 65%, 70%, 75%, 80%, 85%, 90%, 95%, 98%, 99% or 100% sequence identity to a polypeptide selected from group consisting of SEQ ID NO: 14 and SEQ ID NO: 15; or
b) an amino acid sequence having at least 71%, 72%, 75%, 80%, 85%, 90%, 95%, 98%, 99% or 100% sequence identity to a polypeptide selected from group consisting of SEQ ID NO: 17 and SEQ ID NO: 18; or
c) an amino acid sequence having at least 90%, 91%, 92%, 93%, 94%, 95%, 96%, 97%, 98%, 99% or 100% sequence identity to a polypeptide selected from group consisting of SEQ ID NO: 20 and SEQ ID NO: 21.

Further provided is a polypeptide having sclareol synthase activity, wherein the polypeptide comprises an amino acid sequence having at least 90%, 95%, 98%, 99% or 100% sequence identity to a polypeptide selected from the group consisting SEQ ID NO: 4, SEQ ID NO: 5, SEQ ID NO: 23, and SEQ ID NO: 25.

Also provided herein is a nucleic acid encoding a polypeptide described above.

Also provided herein is a nucleic acid encoding a CPP synthase wherein the nucleic acid comprises a nucleotide sequence having at least 90%, 95%, 98%, 99% or 100% sequence identity to the nucleic acid sequence as set forth in SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

Further provided herein is a nucleic acid encoding a sclareol synthase wherein the nucleic acid comprises a nucleotide sequence having at least 90%, 95%, 98%, 99% or 100% sequence identity to SEQ ID NO: 6, SEQ ID NO: 24, SEQ ID NO: 27, SEQ ID NO: 33, or SEQ ID NO: 34.

Also provided is an expression vector comprising the nucleic acids described above, a non-human host organism or cell comprising the nucleic acids described above or comprising the expression vector, non-human host organisms or cells capable of producing GGPP, methods of transforming a non-human host organism or cell, and methods for culturing the non-human host organisms or cells for producing (+)-manool.

DESCRIPTION OF THE DRAWINGS

FIG. 1. Enzymatic pathway from geranylgeranyl diphosphate (GGPP) to (+)-manool.

FIG. 2. Enzymatic pathways from geranylgeranyl diphosphate (GGPP) to (+)-manool and sclareol.

FIG. 3. GCMS analysis of the in vitro enzymatic conversion of GGPP. A. Using the recombinant SmCPS enzyme. B. Using the recombinant ScScS enzyme. C. Combining the SmCPS with ScScS enzymes in a single assay.

FIG. 4. GCMS analysis of (+)-manool produced using *Escherichia coli* cells expressing SmCPS, ScScS and mevalonate pathway enzymes. A. Total ion chromatogram of an extract of the *E. coli* culture medium. B. Total ion chromatogram of a (+)-manool standard. C. Mass spectrum of the major peak (retention time of 14.55 min) in chromatogram A. D. Mass spectrum of the (+)-manool authentic standard.

FIG. 5. GCMS analysis of (+)-manool produced using *E. coli* cells expressing, mevalonate pathway enzymes, a GGPP synthase, ScSCS and five different CPP synthases: SmCPS2 from *Salvia miltiorrhiza*, CfCPS1 from *Coleus forskohlii*, TaTps1 from *Triticum aestivum*, MvCps3 from *Marrubium vulgare* and RoCPS1 from *Rosmarinus officinalis*.

FIG. 6. GCMS analysis of (+)-manool produced using *E. coli* cells expressing, mevalonate pathway enzymes, a GGPP synthase, SmCPS2 and a class I diterpene synthases: NgSCS-del29 from *Nicotiana glutinosa* or SsScS from *Salvia sclarea*.

FIG. 7. *Saccharomyces cerevisiae* expression plasmids were constructed in vivo by co-transformation of yeast with six DNA fragments: a) LEU2 yeast marker, b) AmpR *E. coli* marker, c) Yeast origin of replication, d) *E. coli* replication origin, e) a fragment for co-expression of CrtE and one of the sclareol synthases coding sequences tested, and f) a fragment for expression of one of the copalyl diphosphate (CPP) synthases coding sequences tested.

FIG. 8. GCMS analysis of (+)-manool produced using the modified *S. cerevisiae* strain YST045 expressing a GGPP synthase, ScSCS and five different truncated versions of CPP synthases: SmCPS2 from *Salvia* miltiorrhiza, CfCPS1 from *Coleus forskohlii*, TaTps1 from *Triticum aestivum*, MvCps3 from *Marrubium vulgare* and RoCPS1 from *Rosmarinus officinalis*.

DETAILED DESCRIPTION

Definitions

For the descriptions herein and the appended claims, the use of "or" means "and/or" unless stated otherwise.

Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The following terms have the meanings ascribed to them unless specified otherwise.

The term "polypeptide" means an amino acid sequence of consecutively polymerized amino acid residues, for instance, at least 15 residues, at least 30 residues, at least 50 residues. In some embodiments provided herein, a polypeptide comprises an amino acid sequence that is an enzyme, or a fragment, or a variant thereof.

The term "isolated" polypeptide refers to an amino acid sequence that is removed from its natural environment by any method or combination of methods known in the art and includes recombinant, biochemical and synthetic methods.

The term "protein" refers to an amino acid sequence of any length wherein amino acids are linked by covalent peptide bonds, and includes oligopeptide, peptide, polypeptide and full length protein whether naturally occurring or synthetic.

The terms "biological function," "function," "biological activity" or "activity" refer to the ability of the CPP synthase and the sclareol synthase activity to catalyze the formation of (+)-manool.

The terms "nucleic acid sequence," "nucleic acid," and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes; and the complement of such sequences. The skilled artisan is aware that the nucleic acid sequences of RNA are identical to the DNA sequences with the difference of thymine (T) being replaced by uracil (U).

An isolated nucleic acid or isolated nucleic acid sequence refers to a nucleic acid or nucleic acid sequence that is in an environment different from that in which the nucleic acid or nucleic acid sequence naturally occurs. The term "naturally-occurring" as used herein as applied to a nucleic acid refers to a nucleic acid that is found in a cell in nature. For example, a nucleic acid sequence that is present in an organism, for instance in the cells of an organism, that can be isolated from a source in nature and which it has not been intentionally modified by a human in the laboratory is naturally occurring.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, or at least 50% or 75% of the mass, by weight, of a given sample. In one particular embodiment, these terms refer to the compound of the invention comprising at least 95, 96, 97, 98, 99 or 100% of the mass, by weight, of a given sample. As used herein, the terms "purified," "substantially purified," and "isolated," when referring to a nucleic acid or protein, of nucleic acids or proteins, also refers to a state of purification or concentration different than that which occurs naturally in a cell or organism. Any degree of purification or concentration greater than that which occurs naturally in a cell or organism, including (1) the purification from other associated structures or compounds or (2) the association with structures or compounds to which it is not normally associated in the cell or organism, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Recombinant nucleic acid sequence" are nucleic acid sequences that result from the use of laboratory methods (molecular cloning) to bring together genetic material from more than on source, creating a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

A "chimeric gene" refers to any gene, which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises for example a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein. "Regulatory sequence" refers to a nucleic acid sequence that determines the expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the cell or organism, e.g. host cell, plant cell, plant, or microorganism, to be transformed. The sequence also may be entirely or partially synthetic. Regardless of the origin, the nucleic acid sequence associated with the promoter sequence will be expressed or silenced in accordance with promoter properties to which it is linked. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of a (+)-manool synthase in the host cell or organism.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a CPP synthase protein and/or a sclareol synthase protein or which together produce (+)-manool.

The host cell is particularly a bacterial cell, a fungal cell or a plant cell. The host cell may contain a recombinant gene which has been integrated into the nuclear or organelle genomes of the host cell. Alternatively, the host may contain the recombinant gene extra-chromosomally. Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using for example CLUSTAL or BLAST programs The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The term "organism" refers to any non-human multicellular or unicellular organisms such as a plant, or a microorganism. Particularly, a microorganism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, buds, flowers, petioles, petals, pollen, ovules, embryos, tubers, fruits, seed, progeny thereof and the like. Any plant can be used to carry out the methods of an embodiment herein.

Particular Embodiments

In one embodiment provided herein is a method for transforming a host cell or non-human organism comprising transforming a host cell or non-human organism with a nucleic acid encoding a polypeptide having a copalyl diphosphate synthase activity and with a nucleic acid encoding a polypeptide having a sclareol synthase activity, wherein the polypeptide having the copalyl diphosphate activity comprises a) an amino acid sequence having at least 50%, 55%, 60%, 65%, 70%, 75%, 80%, 85%, 90%, 95%, 98%, 99% or 100% sequence identity to a polypeptide selected from group consisting of SEQ ID NO: 14 and SEQ ID NO: 15; or b) an amino acid sequence having at least 71%, 72%, 75%, 80%, 85%, 90%, 95%, 98%, 99% or 100% sequence identity to a polypeptide selected from group consisting of SEQ ID NO: 17 and SEQ ID NO: 18; or c) an amino acid sequence having at least 90%, 91%, 92%, 93%, 94%, 95%, 96%, 97%, 98%, 99% or 100% sequence identity to a polypeptide selected from group consisting of SEQ ID NO: 20 and SEQ ID NO: 21.

In one embodiment, the polypeptide having the sclareol synthase activity comprises an amino acid sequence having at least 90%, 95%, 98%, 99% or 100% sequence identity to a polypeptide selected from the group consisting SEQ ID NO: 4, SEQ ID NO: 5, SEQ ID NO: 23, and SEQ ID NO: 25.

In one embodiment provided herein is a method comprising cultivating a non-human host organism or cell capable of producing a geranylgeranyl diphosphate (GGPP) and transformed to express a polypeptide having a copalyl diphosphate synthase activity wherein the polypeptide having the copalyl diphosphate synthase activity comprises a) an amino acid sequence having at least 50%, 55%, 60%, 65%, 70%, 75%, 80%, 85%, 90%, 95%, 98%, 99% or 100% sequence identity to a polypeptide selected from group consisting of SEQ ID NO: 14 and SEQ ID NO: 15; or b) an amino acid sequence having at least 71%, 72%, 75%, 80%, 85%, 90%, 95%, 98%, 99% or 100% sequence identity to a polypeptide selected from group consisting of SEQ ID NO: 17 and SEQ ID NO: 18; or c) an amino acid sequence having at least 90%, 91%, 92%, 93%, 94%, 95%, 96%, 97%, 98%, 99% or 100% sequence identity to a polypeptide selected from group consisting of SEQ ID NO: 20 and SEQ ID NO: 21; and further transformed to express a polypeptide having a sclareol synthase activity.

Particularly, the polypeptide having the sclareol synthase activity comprises an amino acid sequence having at least 90%, 95%, 98%, 99% or 100% sequence identity to a polypeptide selected from the group consisting SEQ ID NO: 4, SEQ ID NO: 5, SEQ ID NO: 23, and SEQ ID NO: 25.

Further provided herein is an expression vector comprising a nucleic acid encoding a CPP synthase wherein the CPP synthase comprises a polypeptide comprising a) an amino acid sequence having at least 50%, 55%, 60%, 65%, 70%, 75%, 80%, 85%, 90%, 95%, 98%, 99% or 100% sequence identity to SEQ ID NO: 14 or SEQ ID NO: 15; or b) an amino acid sequence having at least 71%, 72%, 75%, 80%, 85%, 90%, 95%, 98%, 99% or 100% sequence identity to SEQ ID NO: 17 or SEQ ID NO: 18; or c) an amino acid sequence having at least 90%, 91%, 92%, 93%, 94%, 95%, 96%, 97%, 98%, 99% or 100% sequence identity to SEQ ID NO: 20 or SEQ ID NO: 21; and further the expression vector comprises a nucleic acid encoding a sclareol synthase enzyme.

Particularly, the sclareol synthase comprises an amino acid sequence having at least 90%, 95%, 98%, 99% or 100% sequence identity to SEQ ID NO: 4, SEQ ID NO: 5, SEQ ID NO: 23, or SEQ ID NO: 25. In a particularly embodiment, the two enzymes, i.e. the CPP synthase and the sclareol synthase, could be on two different vectors or plasmids transformed in the same cell. In a further embodiment, these two enzymes could be on two different vectors or plasmids transformed in two different cells.

Further provided herein is a non-human host organism or cell comprising or transformed to harbor at least one nucleic acid encoding a CPP synthase wherein the CPP synthase comprises
  a) a polypeptide comprising an amino acid sequence having at least 50%, 55%, 60%, 65%, 70%, 75%, 80%, 85%, 90%, 95%, 98%, 99% or 100% sequence identity to SEQ ID NO: 14 or SEQ ID NO: 15; or
  b) an amino acid sequence having at least 71%, 72%, 75%, 80%, 85%, 90%, 95%, 98%, 99% or 100% sequence identity to SEQ ID NO: 17 or SEQ ID NO: 18; or
  c) an amino acid sequence having at least 90%, 91%, 92%, 93%, 94%, 95%, 96%, 97%, 98%, 99% or 100% sequence identity to SEQ ID NO: 20 or SEQ ID NO: 21; and
at least one nucleic acid encoding a sclareol enzyme.

Particularly, the sclareol synthase comprises an amino acid sequence having at least 90%, 95%, 98%, 99% or 100% sequence identity to SEQ ID NO: 4, SEQ ID NO: 5, SEQ ID NO: 23, or SEQ ID NO: 25.

Further provided herein is a non-human host organism or cell comprising or transformed to harbor at least one nucleic acid encoding a CPP synthase wherein the CPP synthase comprises an amino acid sequence having at least 90%, 95%, 98%, 99% or 100% sequence identity to a polypeptide selected from the group consisting of SEQ ID NO: 1 and SEQ ID NO: 2; and
at least one nucleic acid encoding a sclareol enzyme wherein the sclareol synthase comprises an amino acid sequence having at least 90%, 95%, 98%, 99% or 100% sequence identity to a polypeptide selected from the group SEQ ID NO: 23 and SEQ ID NO: 25.

In one embodiment, the nucleic acid that encodes for a CPP synthase provided herein comprises a nucleotide sequence that has at least 90%, 95%, 98%, 99% or 100% sequence identity to SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

In one embodiment, the nucleic acid that encodes for a CPP synthase provided herein comprises a nucleotide sequence having at least 95%, 98%, 99% or 100% sequence identity to SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

In one embodiment, the nucleic acid that encodes for a CPP synthase provided herein comprises a nucleotide sequence having at least 98% %, 99% or 100% sequence identity to SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

In one embodiment, the nucleic acid that encodes for a CPP synthase provided herein comprises a nucleotide sequence having 99% or 100% sequence identity to SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

In one embodiment, the nucleic acid that encodes for a CPP synthase provided herein comprises the nucleotide sequence as set forth in SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

In one embodiment, the CPP synthase comprises a polypeptide comprising
  a) an amino acid sequence having at least 50%, 55%, 60%, 65%, 70%, 75%, 80%, 85%, 90%, 95%, 98%, 99% or 100% sequence identity to a polypeptide selected from the group consisting of SEQ ID NO: 14 and SEQ ID NO: 15; or
  b) an amino acid sequence having at least 71%, 72%, 75%, 80%, 85%, 90%, 95%, 98%, 99% or 100% sequence identity to a polypeptide selected from group consisting of SEQ ID NO: 17 and SEQ ID NO: 18; or
  c) an amino acid sequence having at least 90%, 91%, 92%, 93%, 94%, 95%, 96%, 97%, 98%, 99% or 100% sequence identity to a polypeptide selected from group consisting of SEQ ID NO: 20 and SEQ ID NO: 21.

In one embodiment, the CPP synthase comprises a polypeptide comprising an amino acid sequence having at least 55%, 60%, 65%, 70%, 75%, 80%, 85%, 90%, 95%, 98% or 99% sequence identity to SEQ ID NO: 14.

In one embodiment, the CPP synthase comprises a polypeptide comprising an amino acid sequence having at least 60%, 65%, 70%, 75%, 80%, 85%, 90%, 95%, 98%, 99% or 100% sequence identity to SEQ ID NO: 14.

In one embodiment, the CPP synthase comprises a polypeptide comprising an amino acid sequence having at least 70%, 75%, 80%, 85%, 90%, 95%, 98%, 99% or 100% sequence identity to SEQ ID NO: 14.

In one embodiment, the CPP synthase comprises a polypeptide comprising an amino acid sequence having at least 90%, 95%, 98%, 99% or 100% sequence identity to SEQ ID NO: 14.

In one embodiment, the CPP synthase comprises a polypeptide comprising an amino acid sequence having at least 98%, 99% or 100% sequence identity to SEQ ID NO: 14.

In one embodiment, the CPP synthase comprises a polypeptide comprising the amino acid sequence as set forth in SEQ ID NO: 14.

In one embodiment, the CPP synthase comprises a polypeptide comprising an amino acid sequence having at least 55%, 60%, 65%, 70%, 75%, 80%, 85%, 90%, 95%, 98%, 99% or 100% sequence identity to SEQ ID NO: 15.

In one embodiment, the CPP synthase comprises a polypeptide comprising an amino acid sequence having at least 60%, 65%, 70%, 75%, 80%, 85%, 90%, 95%, 98%, 99% or 100% sequence identity to SEQ ID NO: 15.

In one embodiment, the CPP synthase comprises a polypeptide comprising an amino acid sequence having at least 70%, 75%, 80%, 85%, 90%, 95%, 98%, 99% or 100% sequence identity to SEQ ID NO: 15.

In one embodiment, the CPP synthase comprises a polypeptide comprising an amino acid sequence having at least 90%, 95%, 98%, 99% or 100% sequence identity to SEQ ID NO: 15.

In one embodiment, the CPP synthase comprises a polypeptide comprising an amino acid sequence having at least 98%, 99% or 100% sequence identity to SEQ ID NO: 15.

In one embodiment, the CPP synthase comprises a polypeptide comprising the amino acid sequence as set forth in SEQ ID NO: 15.

In one embodiment, the CPP synthase comprises a polypeptide comprising an amino acid sequence having at least 75%, 80%, 85%, 90%, 95%, 98%, 99% or 100% sequence identity to SEQ ID NO: 17.

In one embodiment, the CPP synthase comprises a polypeptide comprising an amino acid sequence having at least 80%, 85%, 90%, 95%, 98%, 99% or 100% sequence identity to SEQ ID NO: 17.

In one embodiment, the CPP synthase comprises a polypeptide comprising an amino acid sequence having at least 90%, 95%, 98%, 99% or 100% sequence identity to SEQ ID NO: 17.

In one embodiment, the CPP synthase comprises a polypeptide comprising an amino acid sequence having at least 98%, 99% or 100% sequence identity to SEQ ID NO: 17.

In one embodiment, the CPP synthase comprises a polypeptide comprising the amino acid sequence as set forth in SEQ ID NO: 17.

In one embodiment, the CPP synthase comprises a polypeptide comprising an amino acid sequence having at least 75%, 80%, 85%, 90%, 95%, 98%, 99% or 100% sequence identity to SEQ ID NO: 18.

In one embodiment, the CPP synthase comprises a polypeptide comprising an amino acid sequence having at least 80%, 85%, 90%, 95%, 98%, 99% or 100% sequence identity to SEQ ID NO: 18.

In one embodiment, the CPP synthase comprises a polypeptide comprising an amino acid sequence having at least 90%, 95%, 98%, 99% or 100% sequence identity to SEQ ID NO: 18.

In one embodiment, the CPP synthase comprises a polypeptide comprising an amino acid sequence having at least 98%, 99% or 100% sequence identity to SEQ ID NO: 18.

In one embodiment, the CPP synthase comprises a polypeptide comprising the amino acid sequence as set forth in SEQ ID NO: 18.

In one embodiment, the CPP synthase comprises a polypeptide comprising an amino acid sequence having at least 91%, 92%, 93%, 94%, 95%, 96%, 97%, 98%, 99% or 100% sequence identity to SEQ ID NO: 20.

In one embodiment, the CPP synthase comprises a polypeptide comprising an amino acid sequence having at least 95%, 96%, 97%, 98%, 99% or 100% sequence identity to SEQ ID NO: 20.

In one embodiment, the CPP synthase comprises a polypeptide comprising an amino acid sequence having at least 98%, 99% or 100% sequence identity to SEQ ID NO: 20.

In one embodiment, the CPP synthase comprises a polypeptide comprising the amino acid sequence as set forth in SEQ ID NO: 20.

In one embodiment, the CPP synthase comprises a polypeptide comprising an amino acid sequence having at least 91%, 92%, 93%, 94%, 95%, 96%, 97%, 98%, 99% or 100% sequence identity to SEQ ID NO: 21.

In one embodiment, the CPP synthase comprises a polypeptide comprising an amino acid sequence having at least 95%, 96%, 97%, 98%, 99% or 100% sequence identity to SEQ ID NO: 21.

In one embodiment, the CPP synthase comprises a polypeptide comprising an amino acid sequence having at least 98%, 99% or 100% sequence identity to SEQ ID NO: 21.

In one embodiment, the CPP synthase comprises a polypeptide comprising an amino acid sequence having at least 99% sequence identity to SEQ ID NO: 21.

In one embodiment, the CPP synthase comprises a polypeptide comprising the amino acid sequence as set forth in SEQ ID NO: 21.

In one embodiment, the nucleic acid encoding the sclareol synthase enzyme comprises a nucleotide sequence having at least 90%, 95%, 98%, 99% or 100% sequence identity to SEQ ID NO: 6, SEQ ID NO: 24, SEQ ID NO: 27, SEQ ID NO: 33, or SEQ ID NO: 34.

In one embodiment, the sclareol synthase comprises an amino acid sequence having at least 90%, 95%, 98%, 99% or 100% sequence identity to SEQ ID NO: 4.

In one embodiment, the sclareol synthase comprises an amino acid sequence having at least 95%, 98%, 99% or 100% sequence identity to SEQ ID NO: 4.

In one embodiment, the sclareol synthase comprises an amino acid sequence having at least 98%, 99% or 100% sequence identity to SEQ ID NO: 4.

In one embodiment, the sclareol synthase comprises an amino acid sequence having at least 99% sequence identity to SEQ ID NO: 4.

In one embodiment, the sclareol synthase comprises the amino acid sequence as set forth in SEQ ID NO: 4.

In one embodiment, the sclareol synthase comprises an amino acid sequence having at least 90%, 95%, 98%, 99% or 100% sequence identity to SEQ ID NO: 5.

In one embodiment, the sclareol synthase comprises an amino acid sequence having at least 95%, 98%, 99% or 100% sequence identity to SEQ ID NO: 5.

In one embodiment, the sclareol synthase comprises an amino acid sequence having at least 98%, 99% or 100% sequence identity to SEQ ID NO: 5.

In one embodiment, the sclareol synthase comprises an amino acid sequence having at least 99% sequence identity to SEQ ID NO: 5.

In one embodiment, the sclareol synthase comprises the amino acid sequence as set forth in SEQ ID NO: 5.

In one embodiment, the sclareol synthase comprises an amino acid sequence having at least 90%, 95%, 98%, 99% or 100% sequence identity to SEQ ID NO: 23.

In one embodiment, the sclareol synthase comprises an amino acid sequence having at least 95%, 98%, 99% or 100% sequence identity to SEQ ID NO: 23.

In one embodiment, the sclareol synthase comprises an amino acid sequence having at least 98%, 99% or 100% sequence identity to SEQ ID NO: 23.

In one embodiment, the sclareol synthase comprises an amino acid sequence having at least 99% sequence identity to SEQ ID NO: 23.

In one embodiment, the sclareol synthase comprises the amino acid sequence as set forth in SEQ ID NO: 23.

In one embodiment, the sclareol synthase comprises an amino acid sequence having at least 90%, 95%, 98%, 99% or 100% sequence identity to SEQ ID NO: 25.

In one embodiment, the sclareol synthase comprises an amino acid sequence having at least 95%, 98%, 99% or 100% sequence identity to SEQ ID NO: 25.

In one embodiment, the sclareol synthase comprises an amino acid sequence having at least 98%, 99% or 100% sequence identity to SEQ ID NO: 25.

In one embodiment, the sclareol synthase comprises an amino acid sequence having at least 99% sequence identity to SEQ ID NO: 25.

In one embodiment, the sclareol synthase comprises the amino acid sequence as set forth in SEQ ID NO: 25.

In another embodiment, provided herein is an expression vector comprising at least one of the nucleic acids described herein.

In another embodiment, provided herein is a non-human host organism or cell that comprises one or more expression vectors comprising a nucleic acid encoding a CPP synthase as described herein and a nucleic acid encoding a sclareol synthase as described herein.

In another embodiment, provided herein is a non-human host organism or cell comprising or transformed to harbor at least one nucleic acid described herein so that it heterologously expresses or over-expresses at least one polypeptide described herein.

In an embodiment, the present invention provides a transformed cell or organism, in which the polypeptides are expressed in higher quantity than in the same cell or organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual,* 1985, Elsevier, New York and Sambrook et al., *Molecular Cloning: A Laboratory Manual,* 2$^{nd}$ edition, 1989, Cold Spring Harbor Laboratory Press. Cloning and expression vectors for higher plants and/or plant cells in particular are available to the skilled person. See for example Schardl et al., *Gene,* 1987, 61:1-11.

Methods for transforming host organisms or cells to harbor transgenic nucleic acids are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

In one embodiment for carrying out the method for producing (+)-manool, herein provided is a method of making at least one polypeptide having a CPP synthase activity and at least one polypeptide having a sclareol synthase activity as described in any embodiment of the invention.

One embodiment provides a method for producing manool comprising
  a) contacting geranylgeranyl diphosphate (GGPP) with a copalyl diphosphate (CPP) synthase as described herein to form a copalyl diphosphate; and
  b) contacting the CPP with a sclareol synthase as described herein to form (+)-manool;
wherein step a) comprises culturing a non-human host organism or host cell capable of producing GGPP and transformed with one or more nucleic acids as described herein or with one or more expression vectors as described herein, so that the non-human host organism or host cell harbors a nucleic acid encoding a polypeptide having CPP synthase activity as described herein and a nucleic acid encoding a polypeptide having a sclareol synthase activity as described herein and expresses or over-expresses the polypeptides.

One embodiment provides the above method for producing manool further comprising prior to step a), transforming a non-human host organism or host cell capable of producing GGPP with
  a) at least one nucleic acid encoding a polypeptide comprising
    i. an amino acid sequence having at least 50%, 55%, 60%, 65%, 70%, 75%, 80%, 85%, 90%, 95%, 98%, 99% or 100% sequence identity to SEQ ID NO: 14 or SEQ ID NO: 15; or
    ii. an amino acid sequence having at least 71%, 72%, 75%, 80%, 85%, 90%, 95%, 98%, 99% or 100% sequence identity to SEQ ID NO: 17 or SEQ ID NO: 18; or
    iii. an amino acid sequence having at least 90%, 91%, 92%, 93%, 94%, 95%, 96%, 97%, 98%, 99% or 100% sequence identity to SEQ ID NO: 20 or SEQ ID NO: 21; and
    having a CPP synthase activity, so that said organism or cell expresses said polypeptide having a CPP synthase activity; and
  b) at least one nucleic acid encoding a polypeptide having a sclareol synthase activity as described herein, so that said organism or cell expresses said polypeptide having a sclareol synthase activity.

In one embodiment, the non-human host organism or host cell capable of producing GGPP comprises
  a) a nucleic acid encoding a CPP synthase comprising SEQ ID NO: 15 and a nucleic acid encoding a sclareol synthase comprising SEQ ID NO: 5; or
  b) a nucleic acid encoding a CPP synthase comprising SEQ ID NO: 18 and a nucleic acid encoding a sclareol synthase comprising SEQ ID NO: 5; or
  c) a nucleic acid encoding a CPP synthase comprising SEQ ID NO: 21 and a nucleic acid encoding a sclareol synthase comprising SEQ ID NO: 5; or
  d) a nucleic acid comprising SEQ ID NO: 16 which encodes for a CPP synthase and a nucleic acid comprising SEQ ID NO: 6 which encodes for a sclareol synthase; or
  e) a nucleic acid comprising SEQ ID NO: 19 which encodes for a CPP synthase and a nucleic acid comprising SEQ ID NO: 6 which encodes for a sclareol synthase; or
  f) a nucleic acid comprising SEQ ID NO: 22 which encodes for a CPP synthase and a nucleic acid comprising SEQ ID NO: 6 which encodes for a sclareol synthase; or
  g) a nucleic acid comprising SEQ ID NO: 26 which encodes for a CPP synthase and a nucleic acid comprising SEQ ID NO: 27 which encodes for a sclareol synthase; or
  h) a nucleic acid comprising SEQ ID NO: 29 which encodes for a CPP synthase and a nucleic acid comprising SEQ ID NO: 27 which encodes for a sclareol synthase; or
  i) a nucleic acid comprising SEQ ID NO: 30 which encodes for a CPP synthase and a nucleic acid comprising SEQ ID NO: 27 which encodes for a sclareol synthase; or
  j) a nucleic acid comprising SEQ ID NO: 31 which encodes for a CPP synthase and a nucleic acid comprising SEQ ID NO: 27 which encodes for a sclareol synthase; or
  k) a nucleic acid comprising SEQ ID NO: 32 which encodes for a CPP synthase and a nucleic acid comprising SEQ ID NO: 27 which encodes for a sclareol synthase; or
  l) a nucleic acid encoding a CPP synthase comprising SEQ ID NO: 2 and a nucleic acid encoding a sclareol synthase comprising SEQ ID NO: 23; or m) a nucleic acid encoding a CPP synthase comprising SEQ ID NO: 15 and a nucleic acid encoding a sclareol synthase comprising SEQ ID NO: 23; or
n) a nucleic acid encoding a CPP synthase comprising SEQ ID NO: 18 and a nucleic acid encoding a sclareol synthase comprising SEQ ID NO: 23; or
o) a nucleic acid encoding a CPP synthase comprising SEQ ID NO: 21 and a nucleic acid encoding a sclareol synthase comprising SEQ ID NO: 23; or
p) a nucleic acid encoding a CPP synthase comprising SEQ ID NO: 2 and a nucleic acid encoding a sclareol synthase comprising SEQ ID NO: 25; or
q) a nucleic acid encoding a CPP synthase comprising SEQ ID NO: 15 and a nucleic acid encoding a sclareol synthase comprising SEQ ID NO: 25; or
r) a nucleic acid encoding a CPP synthase comprising SEQ ID NO: 18 and a nucleic acid encoding a sclareol synthase comprising SEQ ID NO: 25; or
s) a nucleic acid encoding a CPP synthase comprising SEQ ID NO: 21 and a nucleic acid encoding a sclareol synthase comprising SEQ ID NO: 25; or
t) a nucleic acid comprising SEQ ID NO: 16 which encodes for a CPP synthase and a nucleic acid comprising SEQ ID NO: 24 which encodes for a sclareol synthase; or
u) a nucleic acid comprising SEQ ID NO: 19 which encodes for a CPP synthase and a nucleic acid comprising SEQ ID NO: 24 which encodes for a sclareol synthase; or
v) a nucleic acid comprising SEQ ID NO: 22 which encodes for a CPP synthase and a nucleic acid comprising SEQ ID NO: 24 which encodes for a sclareol synthase; or
w) a nucleic acid comprising SEQ ID NO: 26 which encodes for a CPP synthase and a nucleic acid comprising SEQ ID NO: 33 which encodes for a sclareol synthase; or
x) a nucleic acid comprising SEQ ID NO: 26 which encodes for a CPP synthase and a nucleic acid comprising SEQ ID NO: 34 which encodes for a sclareol synthase
y) a nucleic acid comprising SEQ ID NO: 29 which encodes for a CPP synthase and a nucleic acid comprising SEQ ID NO: 33 which encodes for a sclareol synthase; or
z) a nucleic acid comprising SEQ ID NO: 29 which encodes for a CPP synthase and a nucleic acid comprising SEQ ID NO: 34 which encodes for a sclareol synthase
aa) a nucleic acid comprising SEQ ID NO: 30 which encodes for a CPP synthase and a nucleic acid comprising SEQ ID NO: 33 which encodes for a sclareol synthase; or
bb) a nucleic acid comprising SEQ ID NO: 30 which encodes for a CPP synthase and a nucleic acid comprising SEQ ID NO: 34 which encodes for a sclareol synthase
cc) a nucleic acid comprising SEQ ID NO: 31 which encodes for a CPP synthase and a nucleic acid comprising SEQ ID NO: 33 which encodes for a sclareol synthase; or
dd) a nucleic acid comprising SEQ ID NO: 31 which encodes for a CPP synthase and a nucleic acid comprising SEQ ID NO: 34 which encodes for a sclareol synthase; or
ee) a nucleic acid comprising SEQ ID NO: 32 which encodes for a CPP synthase and a nucleic acid comprising SEQ ID NO: 33 which encodes for a sclareol synthase; or
ff) a nucleic acid comprising SEQ ID NO: 32 which encodes for a CPP synthase and a nucleic acid comprising SEQ ID NO: 34 which encodes for a sclareol synthase;

wherein the above combinations of nucleic acid sequences and/or synthases also comprise the variants and various percent identities to the SEQ ID NO enumerated as described herein.

In one embodiment, the non-human host organism provided herein is a plant, a prokaryote or a fungus.

In one embodiment, the non-human host provided herein is a microorganism, particularly bacteria or yeast.

In one embodiment, the bacterium provided herein is *Escherichia coli* and yeast is *Saccharomyces cerevisiae*.

In one embodiment, the non-human organism provided herein is *Saccharomyces cerevisiae*.

In one embodiment, the cell is a prokaryotic cell.

In other embodiment, the cell is a bacterial cell.

In one embodiment, the cell is a eukaryotic cell.

In one embodiment, the eukaryotic cell is a yeast cell or a plant cell.

In one embodiment, the manool can be produced by culturing the transformed bacteria or yeast described herein, including through fermentation, for example as described in Paddon et al., *Nature*, 2013, 496:528-532.

In one embodiment, the process of producing (+)-manool produces the (+)-manool at a purity of at least 98.5%.

In another embodiment, a method provided herein further comprising processing the (+)-manool to a derivative using a chemical or biochemical synthesis or a combination of both using methods commonly known in the art.

In one embodiment, the (+)-manool derivative is selected from the group consisting of a hydrocarbon, an alcohol, acetal, aldehyde, acid, ether, ketone, lactone, acetate and an ester.

According to any embodiment of the invention, said (+)-manool derivative is a $C_{10}$ to $C_{25}$ compound optionally comprising one, two or three oxygen atoms.

In a further embodiment, the derivative is selected from the group consisting of manool acetate ((3R)-3-methyl-5-[(1S,4aS,8aS)-5,5,8a-trimethyl-2-methylenedecahydro-1-naphthalenyl]-1-penten-3-yl acetate), copalol ((2E)-3-methyl-5-[(1S,4aS,8aS)-5,5,8a-trimethyl-2-methylenedecahydro-1-naphthalenyl]-2-penten-1-ol), copalol acetate ((2E)-3-methyl-5-[(1S,4aS,8aS)-5,5,8a-trimethyl-2-methylenedecahydro-1-naphthalenyl]-2-penten-1-yl acetate), copalal ((2E)-3-methyl-5-[(1S,4aS,8aS)-5,5,8a-trimethyl-2-methylenedecahydro-1-naphthalenyl]-2-pentenal), (+)-manooloxy (4-[(1S,4aS,8aS)-5,5,8a-trimethyl-2-methylenedecahydro-1-naphthalenyl]-2-butanone), Z-11 ((3S,5aR,7aS,11aS,11bR)-3,8,8,11a-tetramethyldodecahydro-3,5a-epoxynaphtho[2,1-c]oxepin), gamma-ambrol (2-[(1S,4aS,8aS)-5,5,8a-trimethyl-2-methylenedecahydro-1-naphthalenyl]ethanol) and Ambrox® (3 aR,5 aS,9aS,9bR)-3a,6,6,9a-tetramethyldodecahydronaphtho[2,1-b]furan).

In another embodiment, a method provided herein further comprises contacting the (+)-manool with a suitable reacting system to convert said (+)-manool in to a suitable (+)-manool derivative. Said suitable reacting system can be of enzymatic nature (e.g. requiring one or more enzymes) or of chemical nature (e.g. requiring one or more synthetic chemicals).

For example, (+)-manool may be enzymatically converted to manooloxy or gamma-ambrol using a process described in the literature, for example as set forth in U.S. Pat. No. 7,294,492, wherein said patent is hereby incorporated by reference in its entirety herein.

In yet another embodiment, the (+)-manool derivative is copalol and its esters with a $C_1$-$C_5$ carboxylic acids.

In yet another embodiment, the (+)-manool derivative is a (+)-manool ester with a $C_1$-$C_5$ carboxylic acids.

In one embodiment, the (+)-manool derivative is copalal.

In one embodiment, the (+)-manool derivative is manooloxy.

In yet another embodiment, the (+)-manool derivative is Z-11.

In one embodiment, the (+)-manool derivative is an ambrol or is a mixture thereof and its esters with a $C_1$-$C_5$ carboxylic acids, and in particular gamma-ambrol and its esters.

In a further embodiment, the (+)-manool derivative is Ambrox®, sclareolide (also known as 3a,6,6,9a-tetramethyldecahydronaphtho[2,1-b]furan-2(1H)-one and all its diastereoisomer and stereoisomers), 3,4a,7,7,10a-pentamethyldodecahydro-1H-benzo[f]chromen-3-ol or 3,4a,7,7,10a-pentamethyl-4a,5,6,6a,7,8,9,10,10a,10b-decahydro-1H-benzo[f]chromene and all their diastereoisomer and stereoisomers cyclic ketone and open form, (1R,2R,4aS,8aS)-1-(2-hydroxyethyl)-2,5,5,8a-tetramethyldecahydronaphthalen-2-ol DOL, gamma-ambrol.

Specific examples of how said derivatives (e.g. a triene hydrocarbon, an acetate or copalol) can be obtained are detailed in the Examples.

For instance, the manool obtained according to the invention can be processed into Manooloxy (a ketone, as per known methods) and then into ambrol (an alcohol) and ambrox (an ether), according to EP 212254.

The ability of a polypeptide to catalyze the synthesis of a particular sesquiterpene can be confirmed by performing the enzyme assay as detailed in the Examples provided herein.

Polypeptides are also meant to include truncated polypeptides provided that they keep their (+)-manool synthase activity and their sclareol synthase activity.

As intended herein below, a nucleotide sequence obtained by modifying the sequences described herein may be performed using any method known in the art, for example by introducing any type of mutations such as deletion, insertion or substitution mutations. Examples of such methods are cited in the part of the description relative to the variant polypeptides and the methods to prepare them.

The percentage of identity between two peptide or nucleotide sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web. Preferably, the BLAST program (Tatiana et al., *FEMS Microbiol Lett.*, 1999, 174:247-250) set to the default parameters, available from the National Center for Biotechnology Information (NCBI) at http://www.ncbi.nlm.nih.gov/BLAST/b12seq/wblast2.cgi, can be used to obtain an optimal alignment of protein or nucleic acid sequences and to calculate the percentage of sequence identity.

The polypeptide to be contacted with GGPP in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. In another embodiment, the GGPP may be contacted with the polypeptide in the culture medium where the polypeptide may be released from the host organism, unicellular organism or cell. If the organism or cell accumulates the polypeptide within its cells, the polypeptide may be obtained by disruption or lysis of the cells. The GGPP may be contacted with the polypeptide upon further extraction of the polypeptide from the cell lysate or through contact with the cell lysate without necessarily conducting such an extraction.

According to another particularly embodiment, the method of any of the above-described embodiments is carried out in vivo. These embodiments provided herein are particularly advantageous since it is possible to carry out the method in vivo without previously isolating the polypeptide. The reaction occurs directly within the organism or cell transformed to express said polypeptide.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells.

A particular organism or cell is meant to be "capable of producing GGPP" when it produces GGPP naturally or when it does not produce GPPP naturally but is transformed to produce GGPP, either prior to the transformation with a nucleic acid as described herein or together with said nucleic acid. Organisms or cells transformed to produce a higher amount of GGPP than the naturally occurring organism or cell are also encompassed by the "organisms or cells capable of producing GGPP". Several methods to transform organisms, for example microorganisms, so that they produce GGPP are known, for example in Schalk et al., J. Am. Chem. Soc., 2013, 134:18900-18903.

Non-human host organisms suitable to carry out the method of an embodiment herein in vivo may be any non-human multicellular or unicellular organisms. In a particular embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In a more particular embodiment the non-human host organism used to carry out the method of an embodiment herein in vivo is a microorganism. Any microorganism can be used but according to an even more particular embodiment said microorganism is a bacteria or yeast. Most particularly, said bacterium is *E. coli* and said yeast is *Saccharomyces cerevisiae*.

Some of these organisms do not produce GGPP naturally or only in small amounts. To be suitable to carry out the method of an embodiment herein, these organisms have to be transformed to produce said precursor or engineered to produce said precursor in larger amounts. They can be so transformed either before the modification with the nucleic acid described according to any of the above embodiments or simultaneously, as explained above.

In one embodiment, the non-human host organism or cell capable of producing GGPP is transformed with a nucleic acid encoding a CPP synthase or variant thereof as described herein and a nucleic acid encoding a sclareol synthase or variant thereof as described herein, wherein the non-human host organism or cell capable of producing GGPP has been engineered to over-express a GGPP synthase or transformed with a nucleic acid encoding a GGPP synthase.

In one embodiment, the non-human host organism or cell comprises a nucleic acid encoding a GGPP synthase, a nucleic acid encoding a CPP synthase or variant thereof as described herein, and a nucleic acid encoding a sclareol synthase or variant thereof as described herein, wherein at least one of said nucleic acids is heterologous to the non-human host organism or cell.

Isolated higher eukaryotic cells can also be used, instead of complete organisms, as hosts to carry out the method of an embodiment herein in vivo. Suitable eukaryotic cells may be any non-human cell, but are particularly plant or fungal cells.

According to another embodiment, the polypeptides having a CPP synthase activity used in any of the embodiments described herein or encoded by the nucleic acids described herein may be variants obtained by genetic engineering, provided that said variant keeps its CPP synthase activity.

According to another embodiment, the polypeptides having a sclareol synthase activity used in any of the embodiments described herein or encoded by the nucleic acids described herein may be variants obtained by genetic engineering, provided that said variant keeps its sclareol synthase activity or has manool synthase activity.

As used herein, the polypeptide is intended as a polypeptide or peptide fragment that encompasses the amino acid sequences identified herein, as well as truncated or variant polypeptides, provided that they keep their CPP synthase activity and their sclareol synthase activity and/or manool synthase activity.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, encompassed herein are methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also advantageously be used in the methods of an embodiment herein.

A variant may also differ from the polypeptide of an embodiment herein by attachment of modifying groups which are covalently or non-covalently linked to the polypeptide backbone.

The variant also includes a polypeptide which differs from the polypeptide described herein by introduced N-linked or O-linked glycosylation sites, and/or an addition of cysteine residues. The skilled artisan will recognize how to modify an amino acid sequence and preserve biological activity.

Therefore, in an embodiment, the present invention provides a method for preparing a variant polypeptide having a CPP synthase activity or a sclareol synthase activity or a manool synthase activity, as described in any of the above embodiments, and comprising the steps of:

(a) selecting a nucleic acid according to any of the embodiments exposed above;

(b) modifying the selected nucleic acid to obtain at least one mutant nucleic acid;

(c) transforming host cells or unicellular organisms with the mutant nucleic acid sequence to express a polypeptide encoded by the mutant nucleic acid sequence;

(d) screening the polypeptide for at least one modified property; and, (e) optionally, if the polypeptide has no desired variant CPP synthase activity, sclareol synthase activity, or manool synthase activity repeating the process steps (a) to (d) until a polypeptide with a desired variant CPP synthase activity, sclareol synthase activity, or manool synthase activity is obtained;

(f) optionally, if a polypeptide having a desired variant CPP synthase activity or a sclareol synthase activity or manool synthase activity was identified in step (d), isolating the corresponding mutant nucleic acid obtained in step (c).

According to an embodiment, the variant polypeptide prepared when in combination with either a polypeptide with CPP synthase activity or a sclareol synthase activity is capable of producing (+)-manool.

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution (*Proc Natl Acad Sci USA.,* 1994, 91(22): 10747-1075). In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Mutant nucleic acids may be obtained and separated, which may be used for transforming a host cell according to standard procedures, for example such as disclosed in the present examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

In addition to the gene sequences shown in the sequences disclosed herein, it will be apparent for the person skilled in the art that DNA sequence polymorphisms may exist within a given population, which may lead to changes in the amino acid sequence of the polypeptides disclosed herein. Such genetic polymorphisms may exist in cells from different populations or within a population due to natural allelic variation. Allelic variants may also include functional equivalents.

Further embodiments also relate to the molecules derived by such sequence polymorphisms from the concretely disclosed nucleic acids. These natural variations usually bring about a variance of about 1 to 5% in the nucleotide sequence of a gene or in the amino acid sequence of the polypeptides disclosed herein. As mentioned above, the nucleic acid encoding the polypeptide of an embodiment herein is a useful tool to modify non-human host organisms or cells intended to be used when the method is carried out in vivo.

A nucleic acid encoding a polypeptide according to any of the above-described embodiments is therefore also provided herein.

The nucleic acid of an embodiment herein can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of an embodiment herein also encompass certain isolated nucleotide sequences including those that are substantially free from contaminating endogenous material. The nucleic acid of an embodiment herein may be truncated, provided that it encodes a polypeptide encompassed herein, as described above.

In one embodiment, the nucleic acid of an embodiment herein that encodes for a CPP synthase can be either present naturally in a plant such as *Salvia miltiorrhiza*, or other species, such as *Coleus forskohlii, Triticum aestivum, Marrubium vulgare* or *Rosmarinus officinalis*, or be obtained by modifying SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32.

In a further embodiment, the nucleic acid of an embodiment herein that encodes for a sclareol synthase can be either present naturally in a plant such as *Salvia sclarea*, or other species such as *Nicotiana glutinosa*, or can be obtained by modifying SEQ ID NO: 6, SEQ ID NO: 24, SEQ ID NO: 27, SEQ ID NO: 33, or SEQ ID NO: 34.

Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the CPP synthase and the scalereol synthase may be optimized for increased expression in the host cell. For example, nucleotides of an embodiment herein may be synthesized using codons particular to a host for improved expression.

Another important tool for transforming host organisms or cells suitable to carry out the method of an embodiment herein in vivo is an expression vector comprising a nucleic acid according to any embodiment of an embodiment herein. Such a vector is therefore also provided herein.

Recombinant non-human host organisms and cells transformed to harbor at least one nucleic acid of an embodiment herein so that it heterologously expresses or over-expresses at least one polypeptide of an embodiment herein are also very useful tools to carry out the method of an embodiment herein. Such non-human host organisms and cells are therefore also provided herein.

A nucleic acid according to any of the above-described embodiments can be used to transform the non-human host organisms and cells and the expressed polypeptide can be any of the above-described polypeptides.

Non-human host organisms of an embodiment herein may be any non-human multicellular or unicellular organisms. In a particular embodiment, the non-human host organism is a plant, a prokaryote or a fungus. Any plant, prokaryote or fungus is suitable to be transformed according to the methods provided herein. Particularly useful plants are those that naturally produce high amounts of terpenes.

In a more particular embodiment the non-human host organism is a microorganism. Any microorganism is suitable to be used herein, but according to an even more particular embodiment said microorganism is a bacteria or yeast. Most particularly, said bacterium is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

Embodiments provided herein include, but are not limited to cDNA, genomic DNA and RNA sequences.

Genes, including the polynucleotides of an embodiment herein, can be cloned on basis of the available nucleotide sequence information, such as found in the attached sequence listing and by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

Provided herein are nucleic acid sequences obtained by mutations of SEQ ID NO: 3, SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32, and SEQ ID NO: 6, SEQ ID NO: 24, SEQ ID NO: 27, SEQ ID NO: 33, or SEQ ID NO: 34; such mutations can be routinely made. It is clear to the skilled artisan that mutations, deletions, insertions, and/or substitutions of one or more nucleotides can be introduced into these DNA sequence The nucleic acid sequences of an embodiment herein encoding CPP synthase and the sclareol synthase proteins can be inserted in expression vectors and/or be contained in chimeric genes inserted in expression vectors, to produce CPP synthase and sclareol synthase in a host cell or host organism. The vectors for inserting transgenes into the genome of host cells are well known in the art and include plasmids, viruses, cosmids and artificial chromosomes. Binary or co-integration vectors into which a chimeric gene is inserted are also used for transforming host cells.

An embodiment provided herein provides recombinant expression vectors comprising a nucleic acid encoding for a CPP synthase and a sclareol synthase each, separately, are operably linked to associated nucleic acid sequences such as, for instance, promoter sequences.

Alternatively, the promoter sequence may already be present in a vector so that the nucleic acid sequence which is to be transcribed is inserted into the vector downstream of the promoter sequence. Vectors are typically engineered to have an origin of replication, a multiple cloning site, and a selectable marker.

EXAMPLES

Example 1

Diterpene Synthase Genes.

Two diterpene synthase are necessary for the conversion of geranylgeranyl diphosphate (GGPP) to manool: a type II and a type I diterpene synthase. In the following examples, several type II and type I diterpene synthase combinations were selected and evaluated for the production of manool. For the type II synthases, five copalyl diphosphate (CPP) synthases were selected:
SmCPS, NCBI accession No ABV57835.1, from *Salvia miltiorrhiza*.
CfCPS1, NCBI accession No AHW04046.1, from *Coleus forskohlii*.
TaTps1, NCBI accession No BAH56559.1, from *Triticum aestivum*.
MvCps3, NCBI accession No AIE77092.1, from *Marrubium vulgare*.
RoCPS1, NCBI accession No AHL67261.1, from *Rosmarinus officinalis*.

The codon usage of the cDNA encoding for the five CPP synthases were modified for optimal expression in *E. coli* (DNA 2.0, Menlo Park, Calif. 94025) and the NdeI and KpnI restriction sites were added at 5'-end and 3'-end, respectively. In addition, the cDNA were designed to express the recombinant CPP synthase with deletion of the predicted peptide signal (58, 63, 59, 63 and 67 amino acids for SmCPS, CfCPS1, TaTps1, MvCps3 and RoCPS1, respectively).

For the type I diterpene synthase, the sclareol synthase from *Salvia sclarea* (SsScS) was used (NCBI accession No AET21246.1, WO2009095366). The codon usage of the cDNA was optimized for *E. coli* expression (DNA 2.0, Menlo Park, Calif. 94025), the 50 first N-terminal codon were removed and the NdeI and KpnI restriction sites were added at the 5'-end and 3'-end, respectively. All the cDNAs were synthesized in vitro and cloned in the pJ208 or pJ401 plasmid (DNA 2.0, Menlo Park, Calif. 94025, USA).

Example 2

Expression Plasmids.

The modified SmCPS-encoding cDNA (SmCPS2) and sclareol synthase (SsScS)-encoding cDNA (1132-2-5 opt) were digested with NdeI and KpnI and ligated into the pETDuet-1 plasmid providing the pETDuet-SmCPS2 and pETDuet-1132opt expression plasmids, respectively.

Another plasmid was constructed to co-expression the SmCPS2 and SsScS enzymes together with a geranylgeranyl diphophate (GGPP) synthase. For the GGPP synthase, the CrtE gene from *Pantoea agglomerans* (NCBI accession M38424.1) encoding for a GGPP synthase (NCBI accession number AAA24819.1) was used. The CrtE gene was synthesized with codon optimization and addition of the NcoI and BamHI restriction enzyme recognition sites at the 3' and 5' ends (DNA 2.0, Menlo Park, Calif. 94025, USA) and ligated between NcoI and BamHI site of the pETDuet-1 plasmid to obtain the pETDuet-CrtE plasmid. The SmCPS2 encoding cDNA was digested with NdeI and KpnI and ligated into the pETDuet-1-CrtE plasmid thus providing the pETDuet-CrtE-SmCPS2 construct. The optimized cDNA (1132-2-5_opt) encoding for the truncated SsScS was then introduced in the pETDuet-CrtE-SmCPS2 plasmid using the In-Fusion® technique (Clontech, Takara Bio Europe). For this cloning, the pETDuet-1132opt was used as template in a PCR amplification using the forward primer SmCPS2-1132Inf_F1 5'-CTGTTTGAGCCGGTCGCCTAAGGTAC-CAGAAGGAGATAAATAATGGCGAAAATG AAGGA-GAACTTTAAACG-3' (SEQ ID NO: 9) and the reverse primer 1132-pET_Inf_R1 5'-GCAGCGGTTTCTTTACCA-GACTCGAGGTCAGAACACGAAGCTCTTCATGTC-CTCT-3' (SEQ ID NO: 10). The PCR product was ligated in the plasmid pETDuet-CrtE-SmCPS2 digested with the KpnI and XhoI restriction enzymes and using the In-Fusion® Dry-Down PCR Cloning Kit (Clontech, Takara Bio Europe), providing the new plasmid pETDuet-CrtE-SmCPS2-SsScS. In this plasmid the CrtE gene is under the control of the first T7 promoter of the pETDuet plasmid and the CPP synthase and sclareol synthase encoding cDNAs are organized in a bi-cistronic construct under the control of the second T7 promoter.

The pETDuet-CrtE-SmCPS2-SsScS plasmid was used as template for construction of new expression plasmids carrying the four other CPP synthases-encoding enzymes. The SmCPS2 cDNA was replaced by one of the four new CPP synthase encoding cDNA using an NdeI-KpnI restriction digestion-ligation approach providing the new plasmids pETDuet-CrtE-CfCPS1del63-SsScS, pETDuet-CrtE-TaTps1del59-SsScS, pETDuet-CrtE-MvCps3del63-SsScS and pETDuet-CrtE-RoCPS1del67-SsScS.

Example 3

Heterologous Expression in *E. coli* and Enzymatic Activities.

The expression plasmids (pETDuet-SmCPS2 or pET-Duet-1132opt) were used to transform B121(DE3) *E. coli* cells (Novagene, Madison, Wis.). Single colonies of transformed cells were used to inoculate 25 ml LB medium. After 5 to 6 hours incubation at 37° C., the cultures were transferred to a 20° C. incubator and left 1 hour for equilibration. Expression of the protein was then induced by the addition of 0.1 mM IPTG and the culture was incubated over-night at 20° C. The next day, the cells were collected by centrifugation, re-suspended in 0.1 volume of 50 mM MOPSO (3-morpholino-2-hydroxypropanesulfonic acid sodium salt, 3-(N-morpholinyl)-2-hydroxypropanesulfonic acid sodium salt) buffer at pH 7, 10% glycerol, 1 mM DTT and lysed by sonication. The extracts were cleared by centrifugation (30 min at 20,000 g) and the supernatants containing the soluble proteins were used for further experiments.

Example 4

In vitro diterpene synthase activity assays.

Enzymatic assays were performed in Teflon sealed glass tubes using 50 to 100 µl of protein extract in a final volume of 1 mL of 50 mM MOPSO pH 7, 10% glycerol supplemented with 20 mM $MgCl_2$ and 50 to 200 µM purified geranylgeranyl diphosphate (GGPP) (prepared as described by Keller and Thompson, J. Chromatogr, 1993, 645(1):161-167). The tubes were incubated 5 to 48 hours at 30° C. and the enzyme products were extracted twice with one volume of pentane. After concentration under a nitrogen flux, the extracts were analyzed by GC-MS and compared to extracts from control proteins (obtained from cells transformed with the empty plasmid). GC-MS analysis were performed on an Agilent 6890 series GC system equipped with a DB1 column (30 m×0.25 mm×0.25 mm film thickness; Agilent) and coupled with a 5975 series mass spectrometer. The carrier gas was helium at a constant flow of 1 ml/min. Injection was in split-less mode with the injector temperature set at 260° C. and the oven temperature was programmed from 100° C. to 225° C. at 10° C./min and to 280° C. at 30° C./min. The identities of the products were confirmed based on the concordance of the retention indices and mass spectra of authentic standards.

In these conditions and with the recombinant protein from *E. coli* cells transformed with the plasmids pETDuet-SmCPS2 or pETDuet-1132opt (heterologously expressing the SmCPS or ScScS enzymes, respectively) no production of diterpene molecules was detected in the solvent extracts (the diphosphate-containing diterpenes are not detected in these conditions). Similar assays were then performed but combining the 2 protein extracts containing the recombinant SmCPS and SsScS in a single assay. In these assays, one major product was formed and was identified as being (+)-manool by matching of the mass spectrum and retention index with authentic standards (FIG. 3). This experiment demonstrated that a sclareol synthase can be used together with a CPP synthase to produce manool.

Example 5

In Vivo Manool Production Using *E. coli* Cells.

The in vivo production of manool using cultures of whole cells was evaluated using *E. coli* cells. The CrtE gene inserted in the co-expression plasmids described in Example 2 encodes for an enzyme having GGPP synthase activity that uses farnesyl-diphosphate (FPP) to produce geranylgeranyl diphosphate (GGPP). To increase the level of the endogenous GGPP pool and therefore the productivity in diterpene of the cells, a heterologous complete mevalonate pathway leading to FPP was co-expressed in the same cells. The enzymes of this pathway were expressed using a single plasmid containing all the genes organized in two operons under the control of two promoters. The construction of this expression plasmid is described in patent application WO2013064411 or in Schalk et al. (J. Am. Chem. Soc., 2013, 134:18900-18903). Briefly, a first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP.

KRX *E. coli* cells (Promega) were co-transformed with the plasmid pACYC-29258-4506 and one plasmid selected from pETDuet-CrtE-SmCPS2-SsSc, pETDuet-CrtE-CfCPS1del63-SsScS, pETDuet-CrtE-TaTps1del59-SsScS, pETDuet-CrtE-MvCps3del63-SsScS, or pETDuet-CrtE-RoCPS1del67-SsScS. Transformed cells were selected on carbenicillin (50 µg/ml) and chloramphenicol (34 µg/ml) LB-agarose plates. Single colonies were used to inoculate 5 mL liquid LB medium supplemented with the same antibiotics. The cultures were incubated overnight at 37° C. The next day 2 mL of TB medium supplemented with the same antibiotics were inoculated with 0.2 mL of the overnight culture. After 6 hours incubation at 37° C., the culture was cooled down to 28° C. and 0.1 mM IPTG, 0.2% rhamnose and 1:10 volume of decane were added to each tube. The cultures were incubated for 48 hours at 28° C. The cultures were then extracted twice with 2 volumes of MTBE (Methyl tert-butyl ether), the organic phase were concentrated to 500 µL and analyzed by GC-MS as described above in Example 4 except for the oven temperature which was 1 min hold at 100° C., followed by a temperature gradient of 10° C./min to 220° C. and 20° C./min and to 3000° C.

Under these culture conditions, manool was produced with each combination of type II diterpene synthase and the *Salvia sclarea* sclareol synthase (SsScS) (FIGS. 4 and 5). The amounts of diterpene compounds produced were quantified using an internal standard (alpha-longipinene). The table below shows the quantities of manool produced relative to the SmCPS/SsScS combination, when the ScScS is combined with various type II diterpene synthase (under these experimental conditions, the concentration of manool produced by cells expressing the SmCPS and the SsScS was 300 to 500 mg/L (FIG. 4)). Under these conditions, the highest relative quantity of manool produced was with the TaTps1del59 combination.

| Type II diterpene synthase | Type I diterpene synthase | Relative quantity of manool produced |
|---|---|---|
| SmCPS2 | ScScS | 100 |
| CfCPS1del63 | ScScS | 125.3 |
| TaTps1del59 | ScScS | 139.4 |
| MvCps3del63 | ScScS | 14.9 |
| RoCPS1del67 | ScScS | 77.7 |

Example 6

Production of (+)-Manool Using Recombinant Cells, Purification and NMR Analysis.

One litre of *E. coli* culture was prepared in the conditions described in Example 5, using the SmCPS/SsScS enzyme combination, except that the decane organic phase was replaced by 50 g/L Amberlite XAD-4 for solid phase extraction. The culture medium was filtered to recover the resine. The resine was then washed with 3 column volumes of water, and eluted using 3 column volumes of MTBE. The product was then further purified by flash in chromatography on silica gel using a mobile phase composed of heptane: MTBE 8:2 (v/v). The structure of manool was confirmed by 1H- and 13C-NMR using a Bruker Avance 500 MHz spectrometer. The optical rotation was measured using a Perkin-Elmer 241 polarimeter and the value of $[\alpha]^D_{20}=+26.9°$ (0.3%, CHCl$_3$) confirmed the production of (+)-manool.

Example 7

In Vivo Manool Production in *E. coli* Cells Using a Sclareol Synthases from *Nicotiana glutinosa*.

Sclareol synthases from the plant *Nicotiana glutinosa* are described in WO 2014/022434 and are shown to produce sclareol from labdenediol diphosphate (LPP). Two of the sclareol synthase described in WO 2014/022434 were evaluated, NgSCS-del29 (corresponding to SEQ ID NO: 78 in WO 2014/0224) and NgSCS-del38 (corresponding to SEQ ID NO: 40 of WO 2014/022434) for the production of (+)-manool under conditions similar to Example 5.

A cDNA encoding for NgSCS-del29 was design with a codon usage optimal for *E. coli* expression and including the KpnI and XhoI sites at the 5'-end and 3'-end respectively. This DNA was synthesized by DNA 2.0 (Newark, Calif. 94560).

The pETDuet-CrtE-SmCPS2-SsScS plasmid (Example 2) was used as template for construction of a new expression plasmid. The pETDuet-CrtE-SmCPS2-SsScS plasmid was digested with the KpnI and XhoI restriction sites to replace the SsScS cDNA with the NgSCS-del29 cDNA, providing the new pETDuet-CrtE-SmCPS2-del29 plasmid.

KRX *E. coli* cells (Promega) were co-transformed with the plasmid pACYC-29258-4506 (Example 5) and the pETDuet-CrtE-SmCPS2-del29 plasmid. Transformed cells were selected and cultivated in conditions for production of diterpene as described in Example 5. The production of diterpenes was evaluated using GC-MS analysis and the diterpene compounds produced were quantified using an internal standard (alpha-longipinene). With the new combination of the diterpene synthases SmCPS2 and NgSCS-del29, manool was produced by transformed *E. coli* cells (FIG. 6). The combination of the diterpene synthases SmCPS2 and NgSCS-del38 did not produce manool under the experimental conditions used. Thus at least one of the *Nicotiana glutinosa* sclareol synthase tested can also be used to produce manool from CPP. However, the quantities produced using the *Nicotiana glutinosa* synthase were much lower than with the SsSCS synthase (see table below).

| Type II diterpene synthase | Type I diterpene synthase | Relative quantity of manool produced. |
|---|---|---|
| SmCPS2 | SsScS | 100 |
| SmCPS2 | NgSCS-del29 | 3.1 |

Example 8

The manool obtained in the above examples was converted into its esters according to the following experimental part (herein below as example into its acetate):

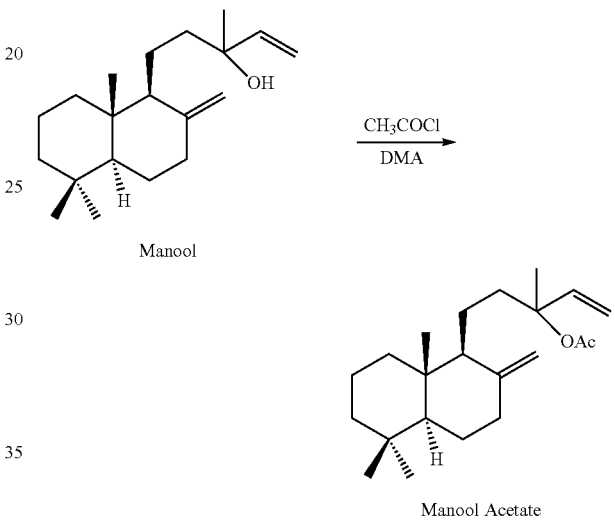

Following the literature (G. Ohloff, *Helv. Chim. Acta* 41, 845 (1958)), 32.0 g (0.11 mole) of pure crystalline (+)-Manool were treated by 20.0 g (0.25 mole) of acetyl chloride in 100 ml of dimethyl aniline for 5 days at room temperature. The mixture was additionally heated for 7 hours at 50° to reach 100% of conversion. After cooling, the reaction mixture was diluted with ether, washed successively with 10% H$_2$SO$_4$, aqueous NaHCO$_3$ and water to neutrality. After drying (Na$_2$SO$_4$) and concentration, the product was distilled (bulb-to-bulb, B.p.=160°, 0.1 mbar) to give 20.01 g (79.4%) of Manool Acetate which was used without further purification.

MS: M$^+$ 332 (0); m/e: 272 (27), 257 (83), 137 (62), 95 (90), 81 (100).

$^1$H-NMR (CDCl$_3$): 0.67, 0.80, 0.87, 1.54 and 2.01 (5s, 3H each), 4.49 (s, 1H), 4.80 (s, 1H), 5.11 (m, 1H), 5.13 (m, 1H), 5.95 (m, 1H).

$^{13}$C-NMR (CDCl$_3$): 14.5 (q), 17.4 (t), 19.4 (t), 21.7 (q), 22.2 (q), 23.5 (q), 24.2 (t), 33.5 (s), 33.6 (t), 38.3 (t), 39.0 (t), 39.3 (t), 39.8 (s), 42.2 (t), 55.6 (d), 57.2 (t), 83.4 (s), 106.4 (t), 113.0 (t), 142.0 (d), 148.6 (s), 169.9 (s).

Example 9

The manool acetate obtained in the above examples was converted into its trienes according to the following experimental part (herein below as example into its Sclarene and (Z+E)-Biformene):

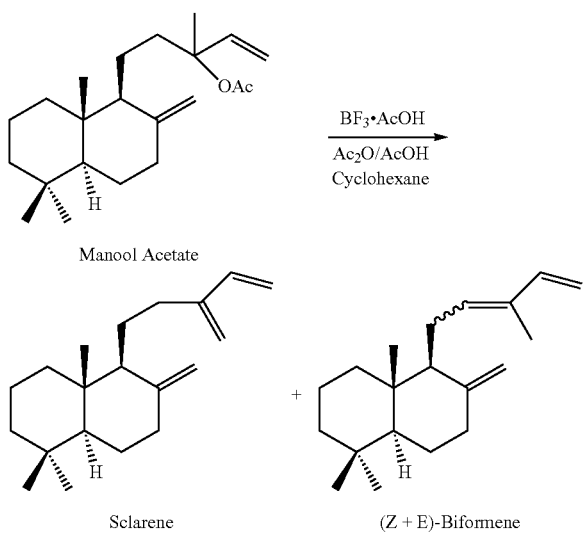

Manool Acetate

BF₃·AcOH
Ac₂O/AcOH
Cyclohexane

Sclarene   (Z + E)-Biformene

To a solution of 0.4 g of Manool Acetate in 4 ml of cyclohexane at room temperature was added 0.029 g (0.05 eq.) of BF₃.AcOH complex. After 15 minutes at room temperature, the reaction was quenched with aqueous NaHCO₃ and washed with water to neutrality. GC-MS analysis showed only hydrocarbons which were identified as Sclarene, (Z) and (E)-biformene. No Copalol Acetate was detected. Another trial with more catalyst (0.15 eq) gave the same result.

Sclarene: MS: M⁺ 272 (18); m/e: 257 (100), 149 (15), 105 (15).

(Z) and (E)-Biformene (identical spectra): MS: M⁺ 272 (29); m/e: 257 (100), 187 (27), 161 (33), 105 (37).

Example 10

The manool obtained in the above examples was converted into Copalyl esters according to the following experimental part (herein below as example into the acetate):

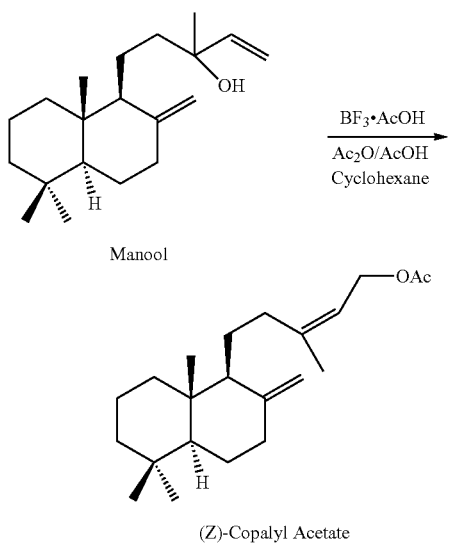

Manool

BF₃·AcOH
Ac₂O/AcOH
Cyclohexane (Z)-Copalyl Acetate
+

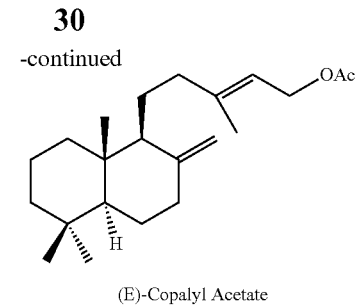

(E)-Copalyl Acetate

To a solution of 0.474 g (0.826 mmole, 0.27 eq.) of BF₃.AcOH in 100 ml of cyclohexane at room temperature was added 4.4 g of acetic anhydride and 12.1 g of acetic acid. At room temperature, 10.0 g (33 mmole) of pure crystalline Manool in 15 ml of cyclohexane were added (sl. exothermic) and the temperature was maintained at room temperature using a water bath. After 30 min. of stirring at room temperature, a GC control showed no starting material. The reaction mixture was quenched with 300 ml of aq. saturated NaHCO₃ and treated as usual. The crude mixture (9.9 g) was purified by flash chromatography (SiO₂, pentane/ether 95:5) and bulb-to-bulb distillation (Eb.=130°, 0.1 mbar) to give 4.34 g (37.1%) of a 27/73 mixture of (Z) and (E)-Copalyl Acetate.

(Z)-Copalyl Acetate:
MS: M⁺ 332 (0); m/e: 317 (2), 272 (35)=, 257 (100), 137 (48),95 (68), 81 (70).
¹H-NMR (CDCl₃): 0.67, 0.80, 0.87 1.76 and 2.04 (5s, 3H each), 4.86 (s, 1H), 5.35 (t: J=6 Hz, 1H).

(E)-Copalyl Acetate:
MS: M⁺ 332 (0); m/e: 317 (2), 272 (33)=, 257 (100), 137 (54),95 (67), 81 (74).
¹H-NMR (CDCl₃): 0.68, 0.80, 0.87 1.70 and 2.06 (5s, 3H each), 4.82 (s, 1H), 5.31 (t: J=6 Hz, 1H).
¹³C-NMR (CDCl₃): (Spectrum recorded on (Z/E) mixture, only significant signals are given): 61.4 (t), 106.2 (t), 117.9 (d), 143.1 (s), 148.6 (s), 171.1 (s).

Example 11

The copalyl acetate obtained in the above examples was converted into Copalol according to the following experimental part:

(Z + E)-Copalyl Acetate

KOH
EtOH/H₂O

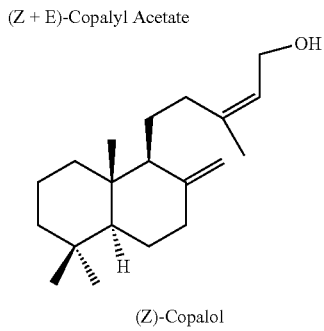

(Z)-Copalol
+

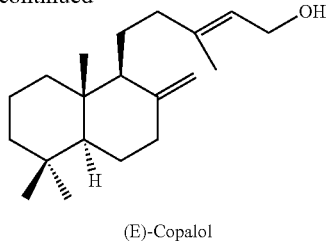

(E)-Copalol

Copalyl Acetate (4.17 g, 12.5 mmole), KOH pellets (3.35 g, 59.7 mmole), water (1.5 g) and EtOH (9.5 ml) were mixed together and stirred for 3 hours at 50°. After usual workup, 3.7 g of crude (Z+E)-Copalol were obtained and purified by flash chromatography (SiO$_2$, pentane/ether 7:2. After evaporation of the solvent, a bulb-to-bulb distillation (Eb=170°, 0.1 mbar) furnished 3.25 g (92%) of a 27/73 mixture of (Z) and (E)-Copalol.

(Z)-Copalol

MS: M$^+$ 290 (3); m/e: 275 (18), 272 (27), 257 (82), 137 (71), 95 (93), 81 (100), 69 (70).

$^1$H-NMR (CDCl$_3$): 0.67, 0.80, 0.87 and 1.74 (4s, 3H each); 4.06 (m, 2H), 4.55 (s, 1H), 4.86 (s, 1H), 5.42 (t: J=6 Hz, 1H).

(E)-Copalol

MS: M$^+$ 290 (3); m/e: 275 (27), 272 (22), 257 (75), 137 (75), 95 (91), 81 (100), 69 (68).

$^1$H-NMR (CDCl$_3$): 0.68, 0.80, 0.87 and 1.67 (4s, 3H each); 4.15 (m, 2H), 4.51 (s, 1H), 4.83 (s, 1H), 5.39 (t, J=6 Hz, 1H)

$^{13}$C-NMR (CDCl$_3$): (Spectrum recorded on (Z/E) mixture, only significant signals are given): 59.4 (t), 106.2 (t), 123.0 (d), 140.6 (s), 148.6 (s).

Example 12

In Vivo Manool Production in *Saccharomyces cerevisiae* Cells Using Different Combinations of CPP Synthases and Sclareol Synthases.

Different combinations of class I and class II diterpene synthases were evaluated for the production of manool in *S. cerevisiae* cells.

For the class II diterpene synthase, five CPP synthases were selected:
  SmCPS, NCBI accession No ABV57835.1, from *Salvia miltiorrhiza*.
  CfCPS1, NCBI accession No AHW04046.1, from *Coleus forskohlii*.
  TaTps1, NCBI accession No BAH56559.1, from *Triticum aestivum*.
  MvCps3, NCBI accession No AIE77092.1, from *Marrubium vulgare*.
  RoCPS1, NCBI accession No AHL67261.1, from *Rosmarinus officinalis*.

For the class I, two putative sclareol synthases from *Nicotiana glutinosa* and one from *Salvia sclarea* were selected:
  NgSCS-del38 (corresponding to SEQ ID NO: 40 of WO 2014/022434).
  NgSCS-del29 (corresponding to SEQ ID NO: 78 of WO 2014/022434).
  SsScS, NCBI accession No AET21246.1, from *Salvia sclarea*.

The codon usage of the DNA encoding for different CPP synthases was modified for optimal expression in *S. cerevisiae*. In addition, the DNA sequences were designed to express the recombinant CPP synthase with deletion of the predicted peptide signal (58, 63, 59, 63 and 67 amino acids for SmCPS, CfCPS1, TaTps1, MvCps3 and RoCPS1, respectively). The NgSCS-del38, NgSCS-del29 and SaSCS DNA sequences were also codon optimized for *S. cerevisiae* expression.

For expression of the different genes in *S. cerevisiae*, a set of plasmids were constructed in vivo using yeast endogenous homologous recombination as previously described in Kuijpers et al., *Microb Cell Fact.*, 2013, 12:47. Each plasmid is composed of six DNA fragments which were used for *S. cerevisiae* co-transformation. The fragments were:
  a) LEU2 yeast marker, constructed by PCR using the primers 5'AGGTGCAGTTCGCGTGCAAT-TATAACGTCGTGGCAACTGTTATCAGTCG TAC-CGCGCCATTCGACTACGTCGTAAGGCC-3' (SEQ ID NO: 44) and 5'TCGTGGTCAAGGCGTGCAAT-TCTCAACACGAGAGTGATTCTTCGGCGTT GTT-GCTGACCATCGACGGTCGAGGAGAACTT-3' (SEQ ID NO: 45) with the plasmid pESC-LEU (Agilent Technologies, California, USA) as template;
  b) AmpR *E. coli* marker, constructed by PCR using the primers 5'-TGGTCAGCAACAACGCCGAAGAAT-CACTCTCGTGTTGAGAATTGCACGCC TTGAC-CACGACACGTTAAGGGATTTTGGTCATGAG-3' (SEQ ID NO: 37) and 5'-AACGCGTACCCTAAG-TACGGCACCACAGTGACTATGCAGTCCG-CACTTTG CCAATGCCAAAAATGTGCGCG-GAACCCCTA-3' (SEQ ID NO: 38) with the plasmid pESC-URA as template;
  c) Yeast origin of replication, obtained by PCR using the primers 5'-TTGGCATTGGCAAAGTGCGGACTG-CATAGTCACTGTGGTGCCGTACTTAG GGTACGCGTTCCTGAACGAAGCATCTGTGCT-TCA-3' (SEQ ID NO: 39) and 5'-CCGAGATGC-CAAAGGATAGGTGCTATGTTGATGACTACGA-CACAGAACTG CGGGTGACATAATGATAGCATTGAAGGAT-GAGACT-3' (SEQ ID NO: 40) with pESC-URA as template;
  d) *E. coli* replication origin, obtained by PCR using the primers 5'-ATGTCACCCGCAGTTCTGTGTCG-TAGTCATCAACATAGCACCTATCCTTTG GCATCTCGGTGAGCAAAAGGCCAGCAAAAGG-3' (SEQ ID NO: 41) and 5'-CTCAGATGTACGGT-GATCGCCACCATGTGACGGAAGCTATCCT-GACAGTG TAGCAAGTGCTGAGCGTCAGACCCCGTAGAA-3' (SEQ ID NO: 42) with the plasmid pESC-URA as template;
  e) a fragment composed by the last 60 nucleotides of the fragment "d", 200 nucleotides downstream the stop codon of the yeast gene PGK1, the GGPP synthase coding sequence CrtE (from *Pantoea agglomerans*, NCBI accession M38424.1) codon optimized for its expression in *S. cerevisiae*, the bidirectional yeast promoter of GAL10/GAL1, one of the tested sclareol synthase coding sequences, 200 nucleotides downstream the stop codon of the yeast gene CYC1 and the sequence 5'-ATTCCTAGTGACGGCCT-TGGGAACTCGATACACGATGTTCAGTAGAC-CGC TCACACATGG-3'(SEQ ID NO: 43), this fragment was obtained by DNA synthesis (DNA 2.0, Menlo Park, Calif. 94025) and
  f) a fragment composed by the last 60 nucleotides of fragment "e", 200 nucleotides downstream the stop codon of the yeast gene CYC1, one of the tested CPP synthase coding sequences, the bidirectional yeast promoter of GAL10/GAL1 and 60 nucleotides corresponding to the beginning of the fragment "a", this fragment was obtained by DNA synthesis (DNA 2.0, Menlo Park, Calif. 94025).

In total 15 plasmids were constructed which cover all the possible combinations of class I and class II diterpene synthases listed above. The table below show all the plasmids.

| Plasmid name | Class II diterpene synthase | Class I diterpene synthase |
|---|---|---|
| Nm | SmCPS2 | SsScS |
| Cf | CfCPS1del63 | SsScS |
| Mv | MvCps3del63 | SsScS |
| Ro | RoCPS1del67 | SsScS |
| Ta | TaTps1del59 | SsScS |
| Nt_Sm | SmCPS2 | NgSCS-del38 |
| Nt_Cf | CfCPS1del63 | NgSCS-del38 |
| Nt_Mv | MvCps3del63 | NgSCS-del38 |
| Nt_Ro | RoCPS1del67 | NgSCS-del38 |
| Nt_Ta | TaTps1del59 | NgSCS-del38 |
| Nt2_Sm | SmCPS2 | NgSCS-del29 |
| Nt2_Cf | CfCPS1del63 | NgSCS-del29 |
| Nt2_Mv | MvCps3del63 | NgSCS-del29 |
| Nt2_Ro | RoCPS1del67 | NgSCS-del29 |
| Nt2_Ta | TaTps1del59 | NgSCS-del29 |

To increase the level of endogenous farnesyl-diphosphate (FPP) pool in S. cerevisiae cells, an extra copy of all the yeast endogenous genes involved in the mevalonate pathway, from ERG10 coding for acetyl-CoA C-acetyltransferase to ERG20 coding for FPP synthetase, were integrated in the genome of the S. cerevisiae strain CEN.PK2-1C (Euroscarf, Frankfurt, Germany) under the control of galactose-inducible promoters, similarly as described in Paddon et al., Nature, 2013, 496:528-532. Briefly, three cassettes were integrated in the LEU2, TRP1 and URA3 loci respectively. A first cassette containing the genes ERG20 and a truncated HMG1 (tHMG1) as described in Donald et al., Proc Natl Acad Sci USA, 1997, 109:E111-8, under the control of the bidirectional promoter GAL10/GAL1 and the genes ERG19 and ERG13 also under the control of GAL10/GAL1 promoter, the cassette was flanked by two 100 nucleotides regions corresponding to the up- and down-stream sections of LEU2. A second cassette where the genes IDI1 and tHMG1 were under the control of the GAL10/GAL1 promoter and the gene ERG13 under the control of the promoter region of GAL7, the cassette was flanked by two 100 nucleotides regions corresponding to the up- and down-stream sections of TRP1. A third cassette with the genes ERG10, ERG12, tHMG1 and ERGS, all under the control of GAL10/GAL1 promoters, the cassette was flanked by two 100 nucleotides regions corresponding to the up- and down-stream sections of URA3. All genes in the three cassettes included 200 nucleotides of their own terminator regions. Also, an extra copy of GAL4 under the control of a mutated version of its own promoter, as described in Griggs and Johnston, Proc Natl Acad Sci USA, 1991, 88:8597-8601, was integrated upstream the ERG9 promoter region. In addition, the endogenous promoter of ERG9 was replaced by the yeast promoter region of CTR3 generating the strain YST035. Finally, YST035 was mated with the strain CEN.PK2-1D (Euroscarf, Frankfurt, Germany) obtaining a diploid strain termed YST045.

YST045 was transformed with the above described fragments required for in vivo plasmid assembly. Yeast transformations were performed with the lithium acetate protocol as described in Gietz and Woods, Methods Enzymol., 2002, 350:87-96. Transformation mixtures were plated on SmLeu- media containing 6.7 g/L of Yeast Nitrogen Base without amino acids (BD Difco, New Jersey, USA), 1.6 g/L Dropout supplement without leucine (Sigma Aldrich, Missouri, USA), 20 g/L glucose and 20 g/L agar. Plates were incubated for 3-4 days at 30° C. Single cells were used to produce manool in cultures as described in Westfall et al., Proc Natl Acad Sci USA, 2012, 109:E111-118.

Under these culture conditions, manool was produced with some combinations of type II and type I diterpene synthases. The production of manool was evaluated using GC-MS analysis and quantified using an internal standard. The table below shows the quantities of manool produced relative to the SmCPS/SsScS combination (under these experimental conditions, the concentration of manool produced by cells expressing the SmCPS and the SsScS was 100 to 250 mg/L, the highest quantity of manool produced).

| Class II diterpene synthase | Class I diterpene synthase | Relative quantity of manool produced |
|---|---|---|
| SmCPS2 | SsScS | 100 |
| CfCPS1del63 | SsScS | 67 |
| MvCps3del63 | SsScS | 1 |
| RoCPS1del67 | SsScS | 29 |
| TaTps1del59 | SsScS | 16 |
| SmCPS2 | NgSCS-del38 | 0 |
| CfCPS1del63 | NgSCS-del38 | 0 |
| MvCps3del63 | NgSCS-del38 | 0 |
| RoCPS1del67 | NgSCS-del38 | 0 |
| TaTps1del59 | NgSCS-del38 | 0 |
| SmCPS2 | NgSCS-del29 | 0 |
| CfCPS1del63 | NgSCS-del29 | 0 |
| MvCps3del63 | NgSCS-del29 | 0 |
| RoCPS1del67 | NgSCS-del29 | 0 |
| TaTps1del59 | NgSCS-del29 | 0 |

What is claimed is:

1. A method of producing (+)-manool, the method comprising:
   a) contacting geranylgeranyl diphosphate (GGPP) with a copalyl diphosphate (CPP) synthase to form a copalyl diphosphate, wherein the CPP synthase comprises
      a) an amino acid sequence having at least 90% sequence identity to SEQ ID NO: 14 or SEQ ID NO: 15; or
      b) an amino acid sequence having at least 90% sequence identity to SEQ ID NO: 17 or SEQ ID NO: 18; or
      c) an amino acid sequence having at least 90% sequence identity to SEQ ID NO: 20 or SEQ ID NO: 21; and
   b) contacting the CPP with a sclareol synthase to form the (+)-manool; and
   c) optionally isolating the (+)-manool.

2. The method of claim 1, wherein the CPP synthase comprises
   a) a polypeptide comprising an amino acid sequence having at least 95% sequence identity to SEQ ID NO: 14 or SEQ ID NO: 15; or
   b) a polypeptide comprising an amino acid sequence having at least 95% sequence identity to SEQ ID NO: 17 or SEQ ID NO: 18; or
   c) a polypeptide comprising an amino acid sequence having at least 95% sequence identity to SEQ ID NO: 20 or SEQ ID NO: 21.

3. The method of claim 1, wherein step a) further comprises culturing a non-human host organism or cell capable of producing GGPP and transformed to express at least one polypeptide comprising
   a) an amino acid sequence having at least 90% sequence identity to SEQ ID NO: 14 or SEQ ID NO: 15; or
   b) an amino acid sequence having at least 90% sequence identity to SEQ ID NO: 17 or SEQ ID NO: 18; or c) an amino acid sequence having at least 90% sequence identity to SEQ ID NO: 20 or SEQ ID NO: 21;
and having a CPP synthase activity, under conditions conducive to a production of CPP.

4. The method of claim 1, wherein the method further comprises, prior to step a), transforming a non-human host organism or cell capable of producing GGPP with
a) at least one nucleic acid encoding a polypeptide comprising
   a) an amino acid sequence having at least 90% sequence identity to SEQ ID NO: 14 or SEQ ID NO: 15; or
   b) an amino acid sequence having at least 90% sequence identity to SEQ ID NO: 17 and SEQ ID NO: 18; or
   c) an amino acid sequence having at least 90% sequence identity to SEQ ID NO: 20 or SEQ ID NO: 21; and
   having a CPP synthase activity, so that said organism or cell expresses said polypeptide having a CPP synthase activity; and
b) at least one nucleic acid encoding a polypeptide having a sclareol synthase activity, so that said organism or cell expresses said polypeptide having a sclareol synthase activity.

5. The method as recited in claim 4, wherein the polypeptide having sclareol synthase activity comprises an amino acid sequence having at least 90% sequence identity to SEQ ID NO: 4, SEQ ID NO: 5, SEQ ID NO: 23, or SEQ ID NO: 25.

6. The method as recited in claim 1, further comprising processing the (+)-manool to a (+)-manool derivative using a chemical or biochemical synthesis or a combination of both.

7. The method as recited in claim 6, wherein the derivative is an alcohol, acetal, aldehyde, acid, ether, ketone, lactone, acetate or an ester.

8. The method as recited in claim 6, wherein the derivative is selected from the group consisting of copalol, copalal, manooloxy, Z-11, gamma-ambrol and ambrox.

9. A method for transforming a host cell or non-human organism, the method comprising transforming a host cell or non-human organism with a nucleic acid encoding a polypeptide having a (9S, 10S)-copalyl diphosphate synthase activity and a nucleic acid encoding a polypeptide having a sclareol synthase activity,
wherein the polypeptide having (9S, 10S)-copalyl diphosphate activity comprises
   a) an amino acid sequence having at least 90% sequence identity to SEQ ID NO: 14 or SEQ ID NO: 15; or
   b) an amino acid sequence having at least 90% sequence identity to SEQ ID NO: 20 and SEQ ID NO: 21; and
wherein the polypeptide having sclareol synthase activity comprises an amino acid sequence having at least 90% sequence identity to SEQ ID NO: 4, SEQ ID NO: 5, SEQ ID NO: 23, or SEQ ID NO: 25.

10. The method as recited in claim 4, wherein the non-human host organism or cell is a plant, a prokaryote, or a fungus.

11. The method as recited in claim 4, wherein the non-human host organism or cell is *E. coli* or *Saccharomyces cerevisiae*.

12. An expression vector comprising
a) a nucleic acid encoding a polypeptide having a (9S, 10S)-copalyl diphosphate synthase activity comprising
   a) an amino acid sequence having at least 90% sequence identity to SEQ ID NO: 14 or SEQ ID NO: 15; or
   b) an amino acid sequence having at least 98% sequence identity to SEQ ID NO: 20 or SEQ ID NO: 21; or
b) a nucleic acid encoding a polypeptide having a (9S, 10S)-copalyl diphosphate synthase activity comprising a nucleotide sequence having at least 90% sequence identity to a nucleic acid sequence as set forth in SEQ ID NO: 13, SEQ ID NO: 16, SEQ ID NO: 19, SEQ ID NO: 22, SEQ ID NO: 26, SEQ ID NO: 29, SEQ ID NO: 30, SEQ ID NO: 31, or SEQ ID NO: 32; and
c) a nucleic acid encoding a polypeptide having a sclareol synthase activity, wherein the polypeptide having sclareol synthase activity comprises an amino acid sequence having at least 90% sequence identity to SEQ ID NO: 4, SEQ ID NO: 5, SEQ ID NO: 23, or SEQ ID NO: 25; or
d) a nucleic acid encoding a polypeptide having a sclareol synthase activity comprising a nucleotide sequence having at least 90% sequence identity to SEQ ID NO: 6, SEQ ID NO: 24, SEQ ID NO: 27, SEQ ID NO: 33, or SEQ ID NO: 34.

13. A non-human host organism or cell comprising the expression vector as recited in claim 12.

14. The non-human host organism or cell of claim 13, wherein the non-human host organism or cell is a plant, a prokaryote, a fungus, *Escherichia coli*, or *Saccharomyces cerevisiae*.

15. The method as recited in claim 9, wherein the host cell or non-human organism is a plant, a prokaryote, or a fungus.

16. The method as recited in claim 9, wherein the host cell or non-human organism is *E. coli* or *Saccharomyces cerevisiae*.

* * * * *